US010329356B2

(12) United States Patent
Gelli

(10) Patent No.: US 10,329,356 B2
(45) Date of Patent: Jun. 25, 2019

(54) FUNGAL-SPECIFIC METALLOPROTEASES AND USES THEREOF

(71) Applicant: The Regents of the University of California, Oakland, CA (US)

(72) Inventor: Angela C. Gelli, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/349,928

(22) Filed: Nov. 11, 2016

(65) Prior Publication Data

US 2017/0198060 A1 Jul. 13, 2017

Related U.S. Application Data

(63) Continuation of application No. 14/342,857, filed as application No. PCT/US2012/054251 on Sep. 7, 2012, now Pat. No. 9,493,760.

(60) Provisional application No. 61/532,441, filed on Sep. 8, 2011.

(51) Int. Cl.
| | |
|---|---|
| *C07K 16/40* | (2006.01) |
| *C12N 9/58* | (2006.01) |
| *A61K 38/48* | (2006.01) |
| *A61K 9/00* | (2006.01) |
| *C12N 9/10* | (2006.01) |

(52) U.S. Cl.
CPC ............ *C07K 16/40* (2013.01); *A61K 9/0019* (2013.01); *A61K 38/4886* (2013.01); *C12N 9/1029* (2013.01); *C12N 9/58* (2013.01); *C12Y 203/01* (2013.01); *C12Y 304/24004* (2013.01)

(58) Field of Classification Search
CPC .......................... C12N 9/58; C12Y 304/24004
See application file for complete search history.

(56) References Cited

U.S. PATENT DOCUMENTS

| 9,493,760 B2 | 11/2016 | Gelli |
| 2003/0003143 A1 | 1/2003 | Papahadjopoulos et al. |
| 2005/0010037 A1 | 1/2005 | Wu et al. |
| 2011/0098333 A1 | 4/2011 | Kim |
| 2014/0302122 A1 | 10/2014 | Gelli |

FOREIGN PATENT DOCUMENTS

| EP | 2753358 | 7/2014 |
| WO | WO 1998/016240 | 4/1998 |
| WO | WO 2013/036827 | 3/2013 |

OTHER PUBLICATIONS

Loftus. 2003; End sequencing of clones from full length enriched, normalized, JEC21 cDNA library. GenBank Accession No. CF679424.*

U.S. Office Action dated Dec. 3, 2015 issued in U.S. Appl. No. 14/342,857.
U.S. Notice of Allowance dated Jul. 1, 2016 issued in U.S. Appl. No. 14/342,857.
PCT International Search Report and Written opinion dated Mar. 18, 2013 issued in PCT/US2012/054251.
PCT International Preliminary Report on Patentability dated Mar. 12, 2014 issued in PCT/US2012/054251.
European Extended Search Report dated Apr. 9, 2015 issued in EP 12829313.1.
European Office Action dated Mar. 21, 2016 issued in EP 12829313. 1.
European Office Action dated Feb. 13, 2017 issued in EP 12829313. 1.
Agenda, 8th International Conference on Cryptococcus and Cryptococcosis (8th ICCC), May 4, 2011, One Page.
Blasi, et al., "Solid lipid nanoparticles for targeted brain drug delivery," *Advanced Drug Delivery Reviews* 59:454-477, 2007.
Chang, et al., "Cryptococcal yeast cells invade the central nervous system via transcellular penetration of the blood-brain barrier" *Infection and Immunity* 72(9):4985-4995, 2004.
Chaudhuri, et al., "Surface Acid Proteinase (gp63) of Leishmania mexicana: A metalloenzyme capable of protecting liposome-encapsulated proteins from phagolysosomal degradation by macrophages" *The Journal of Biological Chemistry* 264(13):7483-7489, 1989.
Eigenheer, et al., "Extracellular glycosylphosphatidylinositol-anchored mannoproteins and proteases of Cryptococcus neoformans" *FEMS Yeast Research* 7(4):499-510, 2007.
Gelli, Angie "Extracellular proteases of C. neoformans and their role in CNS invasion of Cryptococci" *8th International Conference on Cryptococcus and Cryptococcosis* (8th ICCC), 5 Pages, 2011.
Guo, et al., "Protein tolerance to random amino acid change" *PNAS* 101(25):9205-9210, 2004.
Hill, et al., "Functional Analysis of Conserved Histidines in ADP-Glucose Pyrophosphorylase from *Escherichia coli*[1]" *Biochemical and Biophysical Research Communications* 244:573-577, 1998.
Kreuter, Jörg "Nanoparticulate systems for brain delivery of drugs," *Advanced Drug Delivery Reviews* 47:65-81, 2001.
Lazar, et al., "Transforming Growth Factor a: Mutation of Aspartic Acid 47 and Leucine 48 Results in Different Biological Activity" *Mol. Cell. Biol.* 8(3):1247-1252, 1988.
Lilly, et al., "An expanded family of fungalysin extracellular metallopeptidases of Coprinopsis cinerea," *Mycologial Research*, 112:389-398, 2008.

(Continued)

*Primary Examiner* — Karen Cochrane Carlson
(74) *Attorney, Agent, or Firm* — Kilpatrick Townsend & Stockton LLP

(57) ABSTRACT

The present invention relates to methods of reducing, delaying, preventing and/or inhibiting the progression of a *Cryptococcus* infection into the central nervous system (CNS) of a subject by inhibiting the activity of a M36 fungalysin metalloprotease (e.g., MPR1) secreted by the *Cryptococcus*. The invention further provides methods of increasing, promoting and/or enhancing delivery of a therapeutic agent across the blood-brain-barrier, comprising systemically administering the therapeutic agent in conjunction with a M36 fungalysin metalloprotease (e.g., MPR1), or an enzymatically active fragment thereof.

19 Claims, 10 Drawing Sheets

Specification includes a Sequence Listing.

(56) References Cited

OTHER PUBLICATIONS

Loftus, et al., "The Genome of the Basidiomycetous Yeast and Human Pathogen Cryptococcus neoformans" *Science* 307:1321-1324, 2005.

Markaryan, et al. "Purification and Characterization of an Elastinolytic Metalloprotease from *Aspergillus fumigatus* and Immunoelectron Microscopic Evidence of Secretion of This Enzyme by the Fungus Invading the Murine Lung," *Infection and Immunity* 62(6):2149-2157, 1994.

Meyer, et al., "The Yeast SPC22/23 Homolog Spc3p is Essential for Signal Peptidase Activity" *The Journal of Biological Chemistry* 272(20):13159-13164, 1997.

Monod, et al. "Isolation and Characterization of a Secreted Metalloprotease of *Aspergillus fumigatus*," *Infection and Immunity* 61(10):4099-4104, 1993.

Steen, et al. "*Cryptococcus neoformans* Gene Expression during experimental Cryptococcal Meningitis," *Eukaryotic Cell* 2(6):1336-1349, 2003.

Vu et al., "Cryptococcus neoformans Promotes Its Transmigration into the Central Nervous System by Inducing Molecular and Cellular Changes in Brain Endothelial Cells" *Infection and Immunity*, 81(9):3139-3147, 2013.

Vu et al., "Invasion of the Central Nervous System by Cryptococcus neoformans Requires a Secreted Fungal Metalloprotease" *mBio*, 5(3):e01101 (14 pages), doi:10.1128/mBio.01101-14, Downloaded from mbio.asm.org on Jul. 14, 2014—Published by mbio.asm.org, 2014.

Wacey, et al., "Disentangling the perturbational effects of amino acid substitutions in the DNA-binding domain of p53" *Hum Genet* 104:15-22, 1999.

NCBI CDD Conserved Protein Domain Accession No. pfam07504, Fungalysin/Thermolysin Propeptide (FTP) Motif, http://www.ncbi.nlm.nih.gov/Structure/cdd/cddsrv.cgi?uid=pfam07504, Nov. 26, 2015.

UniProtKB—Accession No. P43150 (GP63_LEIME), Leishmanolysin C1 protein from gp63-C1 gene, www.uniprot.org/uniprot/P43150, Nov. 27, 2015.

\* cited by examiner

*Fig. 1A-E*

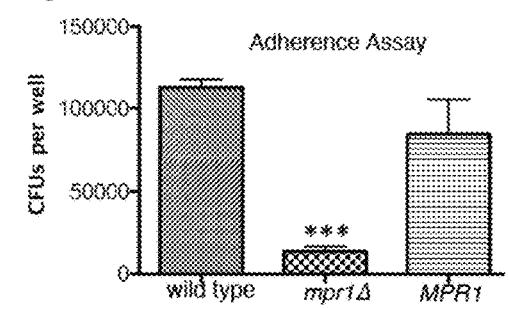
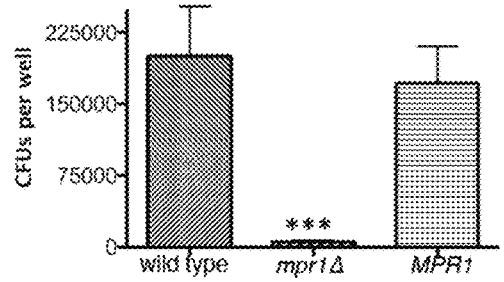
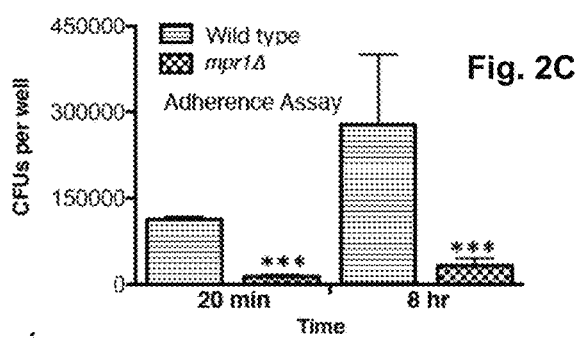
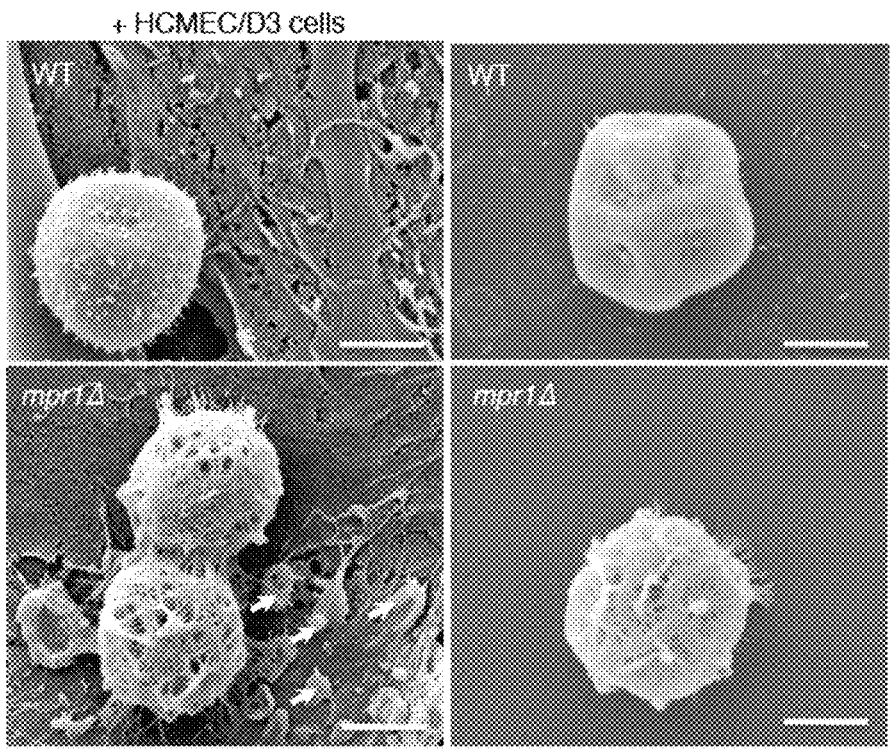
Fig. 2A-D

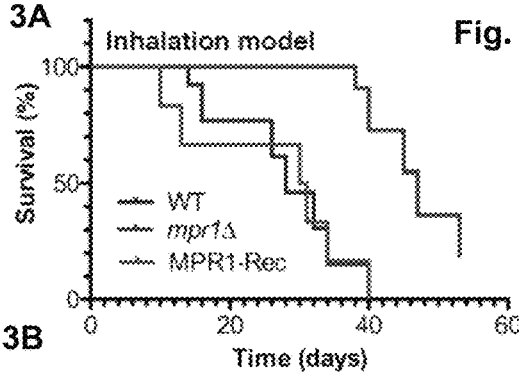
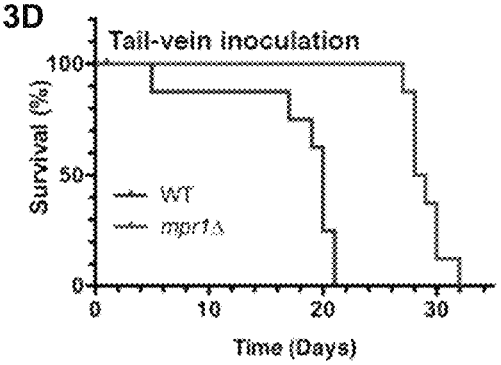
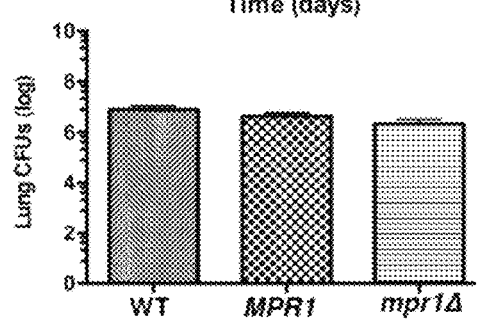
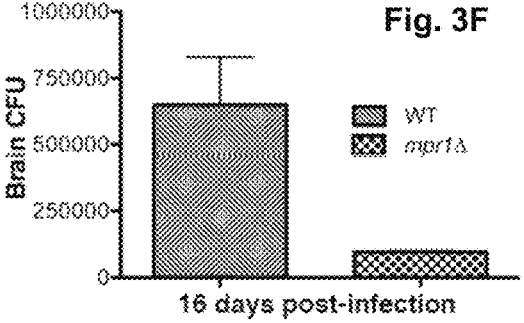
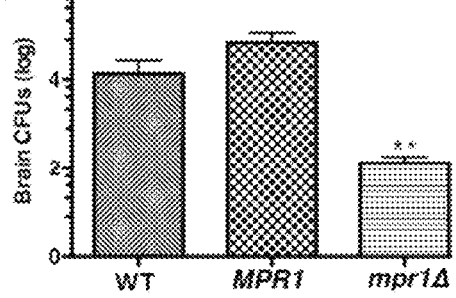
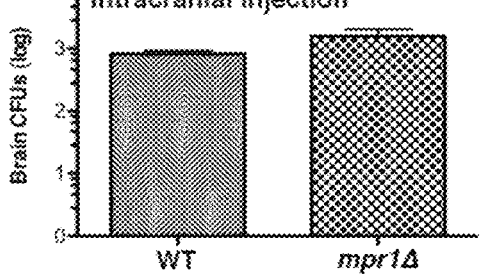
*Fig. 3A-G*

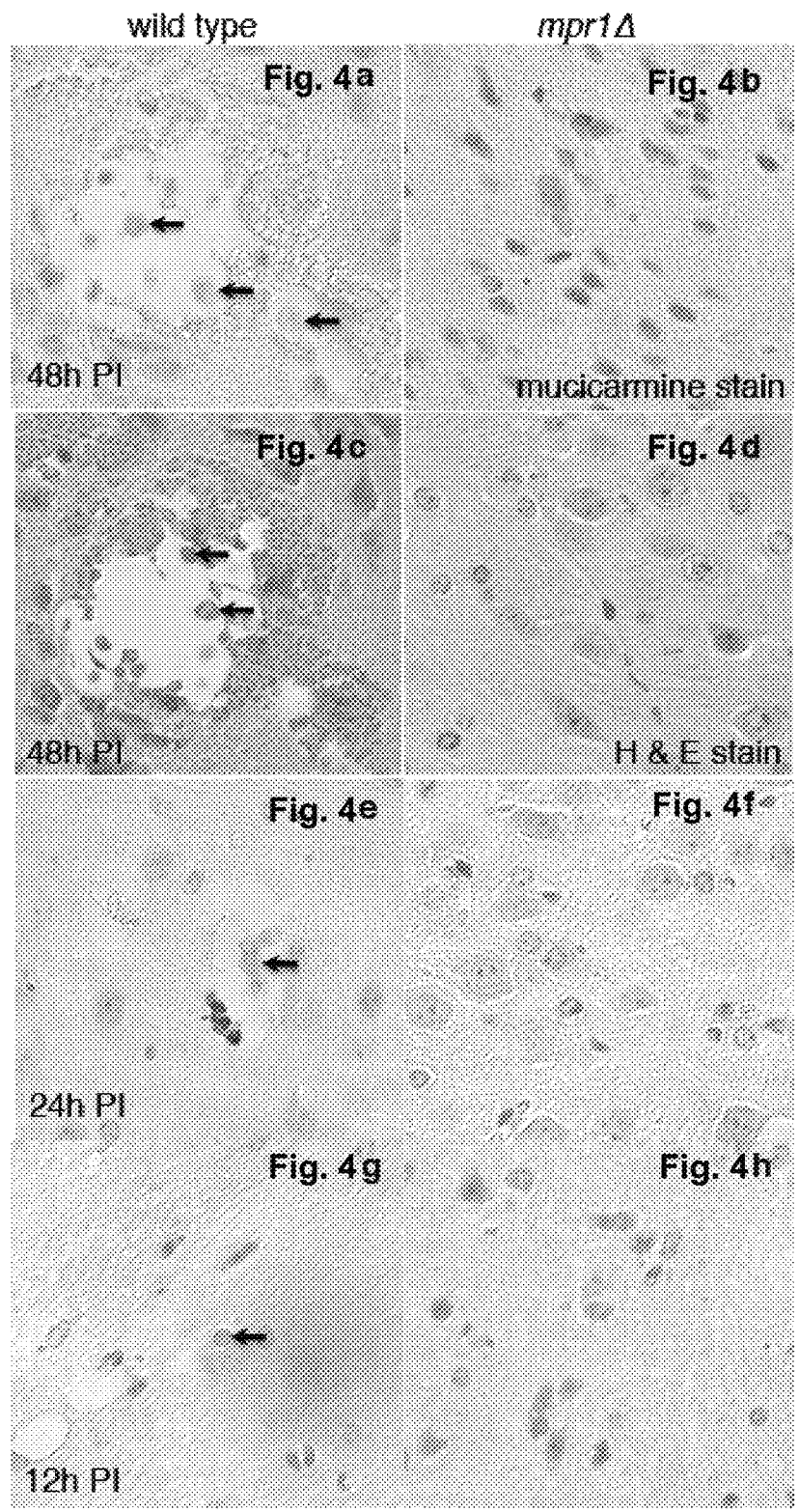
Fig. 4a-h

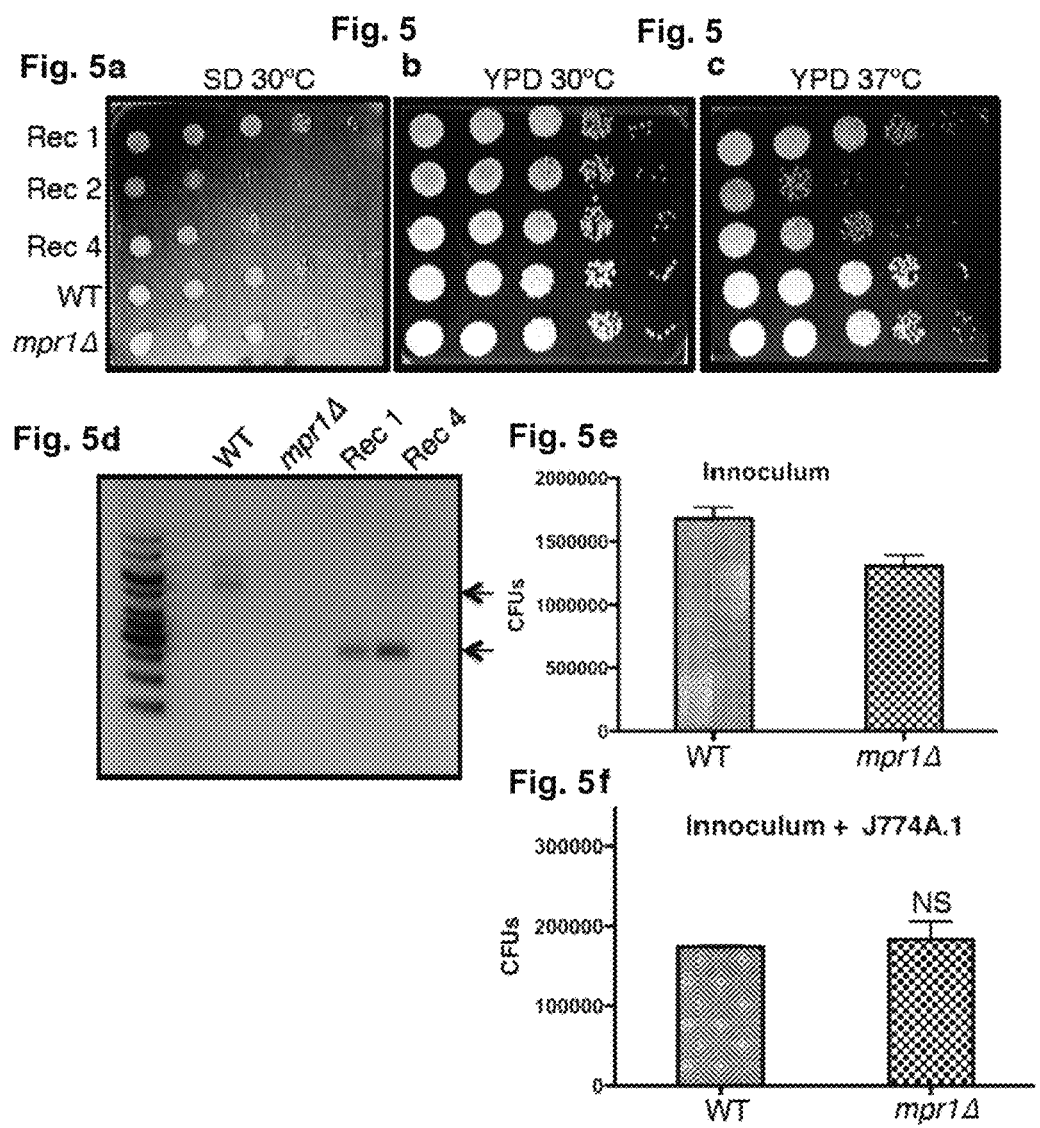
Fig. 5a-f

Signal Sequence

```
CNBJ1810      MKSSALIALLPLLATIVTARPHHHEHKHSASRTRKSLSFGPAHSHASFEVLDDAVHAIEP
CNJ01650      MKSSALIALLPLLATIVTARPHHHEHKHSASRTRKSLSFGPAHSHASFEVLDDAVHAIEP
CGB_I230C     MKSSALIALLPLLATLTAARPHHHEHKHSASRTRKSLSFGPVHSHASFEVLTEAAPVIES
CNAG_04735.2  MKSSALIALLPLLATLTAARPHHREDKHSASRTRKSLSFGPAHSHASFEVLDDAVHVFEP
              *******:*.************.*********.*******  :*.   .:*.
```

FTP Domain

```
CNBJ1810      RGLIGEPIDVNRVAQTFLGSQLGAQEGEGFYIREDSYIDARTGVTHIFARQLLNGLEVSD
CNJ01650      RGLIGEPIDVNRVAQTFLGSQLGAQEGEGFYIREDSYIDARTGVTHIFARQLLNGLEVSD
CGB_I230C     RQLKDEPMDVIRVAQTFLRSQLGTQEGEGFYIRDDSYIDSRTGVTHIFARQLLNGLEVSD
CNAG_04735.2  RGLIDEPIDVKRVAQTFLGSQLGAQEGEGFYIREDSYIDARTGVTHIFARQLLNGLEVSD
              * * .**:**.******.****.********:***********************:***
```

```
CNBJ1810      GDINLNIDRDGRIISWGNSFHPGSAPSLSDIHSSSSGETEKVCATLHQQLDEHKAHLAEL
CNJ01650      GDINLNIDRDGRIISWGNSFHPGSAPSLSDIHSSSSGETEKVCATLHQQLDEHKAHLAEL
CGB_I230C     GDINLNIDRDGRIMSFGNSFHPGSAPDLSAVHSSSSGETERVCATLRQQLDEYKAHLAEL
CNAG_04735.2  GDINLNIDRDGRIMSWGNSFHPGSVPSLSDIHSSSSGETEKVCTTLHQHLDEHKAHLAEL
              *************:*:********.*.***.:********:**:**:**:***:******
```

```
CNBJ1810      KGETGVWGLVKSAAQVVLGSSLPQGEVDHHEIKKVHKSMRHIENHLHAVCRQSAASTQSM
CNJ01650      KGETGVWGLVKSAAQVVLGSSLPQGEVDHHEIKKVHKSMRHIENHLHAVCRQSAASTQSM
CGB_I230C     KGETGVWGLVKSAAEVVLGSSMPQGEVDHHEIKKTIKSMSLIENHLQAVCHRPTASTQSM
CNAG_04735.2  KGETGIWGLVKSAAQVVLGSSLPLGEVDHHEIKETHKSMRHIENHLRAMCDQPAVSTQSM
              *****:********:******:* *********:. *** *****:*:.:.:*****
```

```
CNBJ1810      LSPVEALVSLLPRLSPIDDLEDISPLDLTCTPHHTLKPKPAFAEPPTEVISGAALSKAGV
CNJ01650      LSPVEALVSLLPRLSPIDDLEDISPLDLTCTPHHTLKPKPAFAEPPTEVISGAALSKAGV
CGB_I230C     LSPVDAVVSLLPRLSPNDDLEDISPLELTSTPHHTLKPKPAFAEPPTEVISGAALSKAGV
CNAG_04735.2  LSPVEALVSLLPRLSPIDDLEDISPFDLTSTPHHTLKPKPAFAEPPTEVISGAALSKAGV
              ****:*:********* ********:.**.*********************** *****
```

```
CNBJ1810      VSDVSARLMYTQVSEGAPRLVWKYEVEMKDSWYEAYVDVLSGELIRVVDWASDFDIDELR
CNJ01650      VSDVSARLMYTQVSEGAPRLVWKYEVEMKDSWYEAYVDVLSGELIRVVDWASDFDIDELR
CGB_I230C     VSDVPARLMYTQVSEGAPRLVWKCEVEMKDSWYEAYVDVFSGELIRVVDWASDYDIDELI
CNAG_04735.2  VSDVSARLMYTQVSEGAPRLVWKYEVEMKDSWYEAYVDVLSGELIRVVDWASDFDIDELR
              ****.****************** ***************.*************:******
```

```
CNBJ1810      EKIEMMKGGKQKPLPSPPKTIKPYSYQVFPWGINDPVSGNLSVVTEPWDTVASPLGWHTF
CNJ01650      EKIEMMKGGKQKPLPSPPKTIKPYSYQVFPWGINDPVSGNLSVVTEPWDTVASPLGWHTF
CGB_I230C     KKIEMTNGGKQKPLPGPPENAKPYSLVFPWGVNDPLCGNLSVETEPWDTVASPLGWHMF
CNAG_04735.2  DKIEMMKGGKQKPLPIPPKKIQPYSYQVFPWGINDPVSGNLSVVTEPWDTVASPLGWHSF
              .****  ********.**:. :****   *****:***: ****:.*************** *
```

*Fig. 6a*

Peptidase M36 Domain

```
CNBJ1810      PTSANPWDVTIPGQTTNHNYTVFNTTVGNNAYAHENWEGRNNFLLNSRPINDSHIFVYDY
CNJ01650      PTSANPWDVTIPGQTTNHNYTVFNTTVGNNAYAHENWEGRNNFLLNSRPINDSHIFVYDY
CGB_I230C     PNSANPWDVTIPGQHTNHTHTVFNTTAGNNAIAQENWEGRNNFLLNYRPMNDSHMFMHEY
CNAG_04735.2  PTSANPWDVTIPGETTNHNYTVFNTTAGNNVYAHENWEGRNNFLLNYRPTNDSHIFVYEY
              *.*********: *** :*******:***.* ********.**:** ****:**::*

CNBJ1810      GEPEGLAPKEYVDMVVTQLFYTANMYHDLLYRLGFDEISGNFQAYNFRLGGKGGDPVVCN
CNJ01650      GEPEGLAPKEYVDMVVTQLFYTANMYHDLLYRLGFDEISGNFQAYNFRLGGKGGDPVVCN
CGB_I230C     GEPEGLAPKEYVDMIITQLFYTANMYHDLLYRLGSNEVSGNFQAYNFGLGGKGGDPVVCN
CNAG_04735.2  GEPEGLAPKEYVDMVVTQLFYTANMYHDLLYRLGFDELSGNFQAYNFRLGGKGGDPVVCN
              **************::****************** :*:********* ***********
```

Zinc Binding Site

```
CNBJ1810      AQDGSGYNNANFLTPPDGQAPRMRMYIWDTATPYRDGDLEAGIVIHEYSHGLSTRLTGGP
CNJ01650      AQDGSGYNNANFLTPPDGQAPRMRMYIWDTATPYRDGDLEAGIVIHEYSHGLSTRLTGGP
CGB_I230C     AQDGSGYNNANFLTPPDGQAPRMRMYIWDTATPYRDGDLEAGIVIHEYSHGLSTRLTGGP
CNAG_04735.2  AQDGSGYNNANFLTPPDGQAPRMRMYIWDTATPYRDGDLEAGIVIHEYSHGLSTRLTGGP
              ************************************************************

CNBJ1810      ANSGCLGYGEAGGMGEGWGDAIATLVRQVEEHKNFENGTDVFSMGAWAANTDRGIRNYKY
CNJ01650      ANSGCLGYGEAGGMGEGWGDAIATLVRQVEEHKNFENGTDVFSMGAWAANTDRGIRNYKY
CGB_I230C     ANSGCLGYGEAGGMGEGWGDAIATLVRQVEEHKNFENGTDVFPMGSWAANTPKGIRNYLY
CNAG_04735.2  ANSGCLGYGEAGGMGEGWGDAIATLIRQVEEHKNFENGTDVFSMGAWAANSNRGIRNYKY
              *************************:***************.**:****.:.***** *

CNBJ1810      STNFTINPSTYKTLDKPGYWGVHAIGEVWAEFLFVLSQRLVEKYGFGTTLFPPTDTSKPN
CNJ01650      STNFTINPSTYKTLDKPGYWGVHAIGEVWAEFLFVLSQRLVEKYGFGTTLFPPTDTSKPN
CGB_I230C     TTDPTVNPSTYKTLDKPGYWGVHAIGEVWAEFLFVLSERFVETYGFGPTLFPPTNTSEPN
CNAG_04735.2  STNFTINPSTYKTLDKPGYWGVHAIGEVWAEFLFVLSQRLVEN-------------FA
              :*:.*:*******************************:*:**.*             *

CNBJ1810      DYYTRTSEESIDAGGRSLPLVPKHGNTLAIQLIVDAMKLQPCRPSFFDARNAIIQADQIL
CNJ01650      DYYTRTSEESIDAGGRSLPLVPKHGNTLAIQLIVDAMKLQPCRPSFFDARNAIIQADQIL
CGB_I230C     DYYTSTFEESVDAAGRPRPLVPKHGNTLALQLIVDGMKLQPCRPSFFDARDAIIQADQIL
CNAG_04735.2  GHHS-----------SMPVMRSFRPTKS--------------------------------
              ::::           .  *::  .  *  :

CNBJ1810      TGGENACLIWEAFAERGLGEDAAVVGQTPWGGGVRSDGFRVPKKVCGSKKA
CNJ01650      TGGENACLIWEAFAERGLGEDAAVVGQTPWGGGVRSDGFRVPKKVCGSKKA
CGB_I230C     TGGENACLIWEAFAERGLGQDATVVGQTPWGGGVRTDGHKVPKNICGSKKA
CNAG_04735.2  --------------------------------------------------
```

*Fig. 6b*

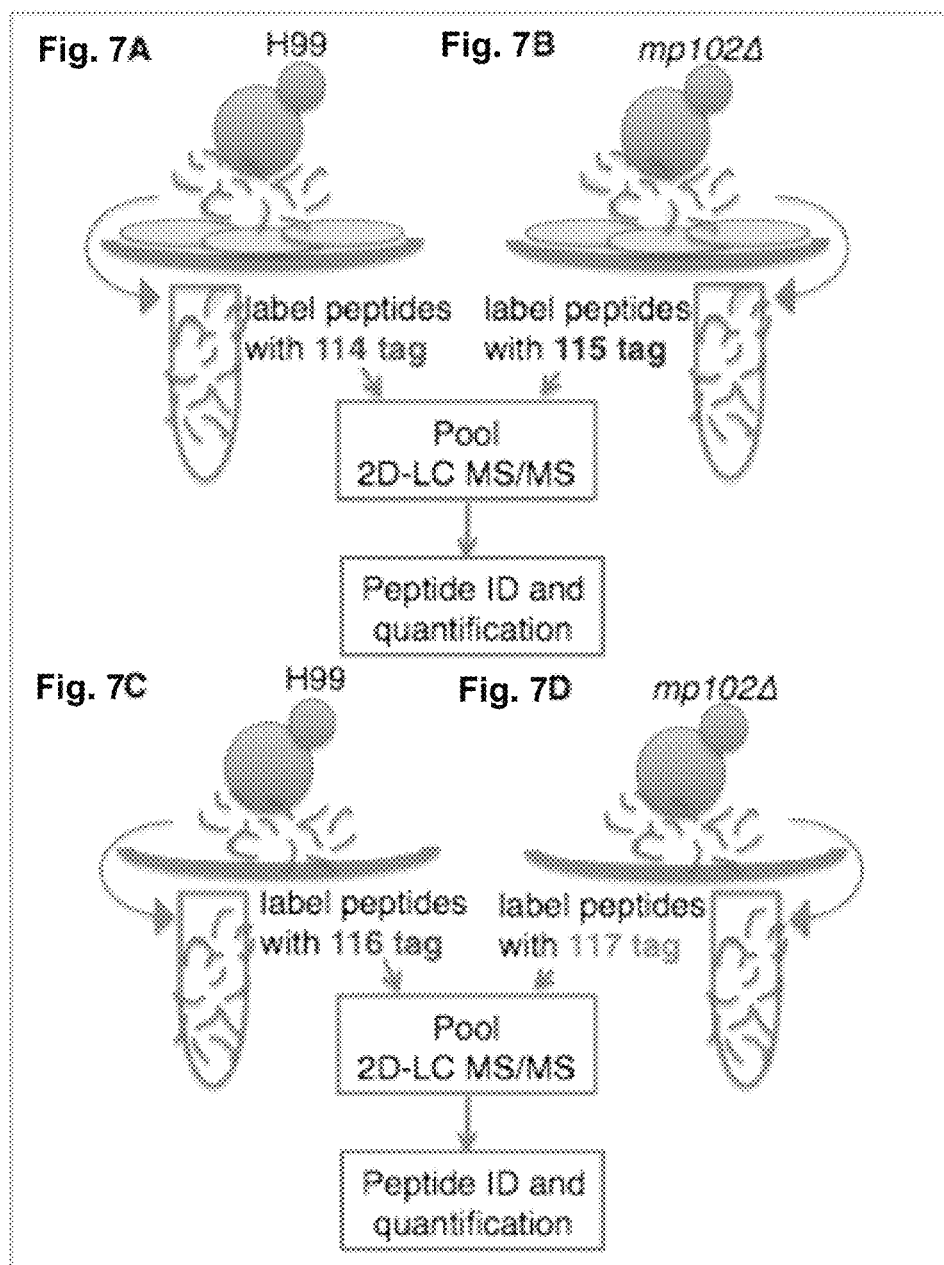
Fig. 7A-D

Fig. 8A
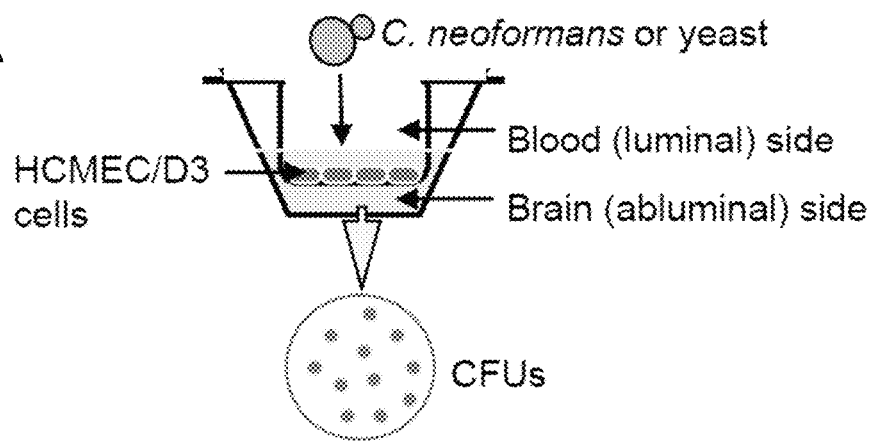
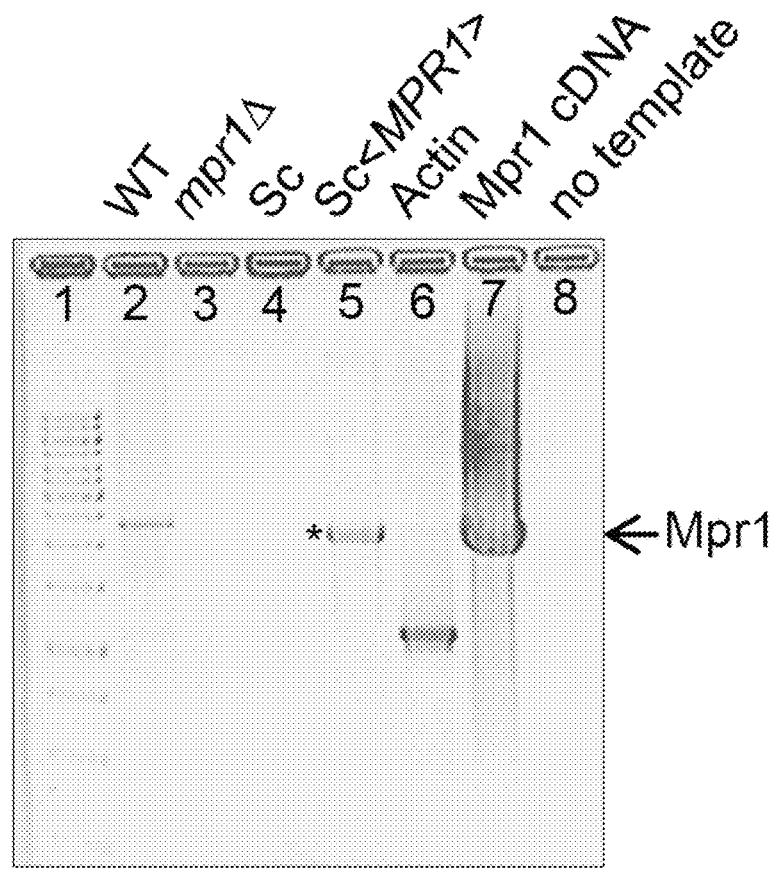
Fig. 8B
Fig. 8A-B

FUNGAL-SPECIFIC METALLOPROTEASES AND USES THEREOF

CROSS-REFERENCE TO RELATED APPLICATIONS

This application is a continuation of U.S. application Ser. No. 14/342,857, filed on Jun. 26, 2014 and issued as U.S. Pat. No. 9,493,760 on Nov. 15, 2016, which is a U.S. National Phase under 35 U.S.C. § 371 of International Application No. PCT/US2012/054251, filed on Sep. 7, 2012, which claims benefit under 35 U.S.C. § 119(e) of U.S. Provisional Application No. 61/532,441, filed on Sep. 8, 2011, all of which are hereby incorporated herein by reference in their entireties for all purposes.

STATEMENT OF GOVERNMENTAL SUPPORT

This invention was made with government support under Grant No. AI060555 awarded by the National Institutes of Health. The government has certain rights in the invention.

FIELD OF THE INVENTION

The present invention relates to methods of reducing, delaying, preventing and/or inhibiting the progression of a *Cryptococcus* infection into the central nervous system (CNS) of a subject by inhibiting the activity of a M36 fungalysin metalloprotease (e.g., MPR1) secreted by the *Cryptococcus*. The invention further provides methods of increasing, promoting and/or enhancing delivery of a therapeutic agent across the blood-brain-barrier, comprising systemically administering the therapeutic agent in conjunction with a M36 fungalysin metalloprotease (e.g., MPR1), or an enzymatically active fragment thereof.

BACKGROUND OF THE INVENTION

*Cryptococcus neoformans* is the leading cause of fungal meningitis, a life-threatening infection that is often difficult to treat due to the poor arsenal of antifungal drugs. *Cryptococcus neoformans* is a fungal pathogen that causes meningoencephalitis primarily in AIDS patients and results in over 1 million active cases of cryptococcosis and 700,000 deaths per year worldwide. See, e.g., World Health Organization. (2003) HIV/AIDS Epidemiological surveillance update for the W.H.O. African region. World Health Organization, Geneva, Switzerland; Mitchell, et al., (1995) *Clin. Microbiol. Rev.* 8:515-548; Sorvillo, et al., (1997) AIDS 11, 673-679; Bicanic, et al., (2004) *British Med. Bulletin,* 72, 99-118; Zuger, et al., (1986) *Ann Intern Med* 104:234-240; Casadevall and Perfect (1998) *Cryptococcus neoformans*. American Society for Microbiology, Washington, D.C.; and Ecevit, et al., (2006) *Clin Infect Dis* 42:1443-1447. The global burden of cryptococcal meningitis remains a serious health concern as studies from Africa, India, Thailand and Asia-Pacific have all reported increases in the incidence of cryptococcal meningitis as an AIDS-defining illness and a leading cause of AIDS mortality. See, e.g., Park, B. J. et al., (2009). *AIDS* 23:525-530. In sub-Saharan Africa *C. neoformans* causes higher mortality than tuberculosis in the AIDS population. See, e.g., Park, B. J. et al., (2009) *AIDS* 23:525-530 Several outbreaks of cryptococcal infections (by the sibling species, *C. gattii*) in the Pacific Northwest of the US and Canada over the last 7 years have claimed the lives of 25% of the individuals infected, most of whom were not immunocompromised. See, e.g., Kidd, S. E. et al., (2004) *PNAS* 101:17258-17263. The most recent outbreak has occurred in Oregon and new outbreaks are expected in Northern California. See, e.g., Byrnes III, E. J., et al., (2010). *Plos Pathogens* 6:1-16.

Unfortunately, most patients present with significant fungal burden in the brain and consequently, death from cryptococcal infection results from brain edema and raised intracranial pressure. See, e.g., Zuger, A., et al., (1986) *Ann Intern Med* 104, 234-240. It remains a life-threatening infection in part because of the poor arsenal of antifungal agents available especially in parts of Africa where the most common drug available to combat this infection is merely a fungistatic drug (fluconazole). See, e.g., Warkentien, T, et al., (2010) *Int JSTD AIDS* 10:679-684; Nussbaum, J. C., (2010) *Clin Infect Dis* 50:338-344. In these cases AIDS patients often require life-long maintenance therapy since in an immunosuppressed setting fungistatic drugs cannot clear cryptococcal infections. The batch of drugs currently available for the treatment of life-threatening fungal infections, like cryptococcal meningitis, is nowhere near what it should be. See, e.g., Warkentien, T., et al., (2010) *Int J STD AIDS* 10:679-684. Treatment for infected patients in North America usually involves amphotericin B in combination with flucytosine, however amphotericin B is quite toxic often resulting in renal damage and/or renal failure especially in older patients.

Virtually nothing is known about the role of secreted metalloproteases in the virulence and pathogenesis of *C. neoformans*. Remarkably it is still not clear why *C. neoformans* has this particular tropism for the CNS (central nervous system), nor have all the key cryptococcal proteins and signaling pathways facilitating its movement across the BBB (blood-brain barrier, also known as the brain endothelium) and into the CNS been identified. Based on increasing evidence about cryptococcal virulence factors, it is becoming apparent that a combination of virulence factors rather than a single one is most likely involved in the multistep process of cryptococcal dissemination and CNS invasion. See, e.g., Chalier, C. F., et al., (2005) *Am J Path* 166:421-432; Eigenheer, R. A., et al., (2007) *FEMS Yeast Res* 7:499-510; Jong, A., et al., (2007) *Eukaryot Cell* 6:1486-1496; Santangelo, R., et al., (2004) *Infect. & Immun.* 72:2229-2239; Steen, B. R., et al., (2003) *Eukaryot Cell* 2:1336-134; Olszewski, M. A., et al., (2004) *Am J of Path* 164:1761-1771. However, our understanding of the process in which cryptococci transfer from the primary sites of infection to the CNS is incomplete.

SUMMARY OF THE INVENTION

In one aspect, the invention provides methods of reducing, delaying, preventing and/or inhibiting the progression of a *Cryptococcus* infection into the central nervous system (CNS) of a subject in need thereof. In some embodiments, the method comprises inhibiting the activity of a M36 fungalysin metalloprotease (e.g., MPR1) secreted by the *Cryptococcus*, wherein the M36 fungalysin metalloprotease has at least 80% sequence identity, e.g., at least about 81%, 82%, 83%, 84%, 85%, 86%, 87%, 88%, 89%, 90%, 91%, 92%, 93%, 94%, 95%, 96%, 97%, 98% or 99% sequence identity, to an amino acid sequence of SEQ ID NOs:1, 3, 5 or 7.

In a related aspect, the invention provides methods of reducing, inhibiting and/or preventing the transmigration of *Cryptococcus* across the blood-brain-barrier in a subject in need thereof, comprising inhibiting the activity of a M36 fungalysin metalloprotease (e.g., MPR1) secreted by the

*Cryptococcus*, wherein the M36 fungalysin metalloprotease has at least 80% sequence identity, e.g., at least about 81%, 82%, 83%, 84%, 85%, 86%, 87%, 88%, 89%, 90%, 91%, 92%, 93%, 94%, 95%, 96%, 97%, 98% or 99% sequence identity, to an amino acid sequence of SEQ ID NOs: 1, 3, 5 or 7.

In some embodiments, the M36 fungalysin metalloprotease has an amino acid sequence of SEQ ID NOs: 1, 3, 5 or 7.

In some embodiments, the subject is suspected of being infected with *Cryptococcus*. In some embodiments, the subject is known to be infected with *Cryptococcus*. In some embodiments, the subject has tested positive for *Cryptococcus* infection in the cryptococcal antigen lateral flow assay (CrAg LFA). In some embodiments, the subject has pulmonary cryptococcosis. In some embodiments, the subject has no detectable *Cryptococcus* infection of the CNS. In some embodiments, the subject has no detectable *Cryptococcus* infection of the brain. In some embodiments, the subject is immunocompromised. In some embodiments, the subject is human.

In some embodiments, the *Cryptococcus* is selected from the group consisting of *Cryptococcus gattii*, *Cryptococcus neoformans*, *Cryptococcus neoformans* var. *grubii*, *Cryptococcus neoformans* var *grubii* H99, *Cryptococcus* sp. Y13-1, *Cryptococcus laurentii* and *Cryptococcus albidus*.

In some embodiments, the M36 fungalysin metalloprotease is inhibited from binding to its substrate. In some embodiments, the catalytic activity of the M36 fungalysin metalloprotease is inhibited.

In some embodiments, an antigen binding molecule that specifically binds to the M36 fungalysin metalloprotease is administered to the subject. In some embodiments, the antigen binding molecule is an antibody or fragment thereof. In some embodiments, the antigen binding molecule specifically binds to the peptidase_M36 domain of the M36 fungalysin metalloprotease. In some embodiments, the antigen binding molecule specifically binds to the M36 GluZincin superfamily domain of the M36 fungalysin metalloprotease. In some embodiments, the antigen binding molecule specifically binds to the zinc binding site of the M36 fungalysin metalloprotease. In some embodiments, the antigen binding molecule is administered intravenously.

In some embodiments, expression levels of the M36 fungalysin metalloprotease are reduced and/or inhibited. In some embodiments, an inhibitory nucleic acid that inhibits expression of the M36 fungalysin metalloprotease is administered to the subject. In some embodiments, the inhibitory nucleic acid hybridizes to and inhibits a nucleic acid sequence of SEQ ID NOs: 2, 4, 6 or 8, or a complement thereof.

In a further aspect, the invention provides methods of increasing, promoting and/or enhancing delivery of a therapeutic agent across the blood-brain-barrier, comprising systemically administering to a subject in need thereof the therapeutic agent in conjunction with a M36 fungalysin metalloprotease (e.g., MPR1) having at least 80% sequence identity, e.g., at least about 81%, 82%, 83%, 84%, 85%, 86%, 87%, 88%, 89%, 90%, 91%, 92%, 93%, 94%, 95%, 96%, 97%, 98% or 99% sequence identity, to an amino acid sequence of SEQ ID NOs: 1, 3, 5, and/or 7, or a fragment thereof that retains protease activity. In some embodiments, the M36 fungalysin metalloprotease has an amino acid sequence of SEQ ID NOs:1, 3, 5 or 7.

In some embodiments, the M36 fungalysin metalloprotease is the full length enzyme. In some embodiments, the M36 fungalysin metalloprotease is a fragment comprising the peptidase_M36 domain (e.g., comprises a fragment corresponding to residues 446-722 of SEQ ID NOs: 1, 3 and/or 5 and/or corresponding to residues 446-706 of SEQ ID NO:7). In some embodiments, the M36 fungalysin metalloprotease is a fragment comprising and no longer than the peptidase_M36 domain. In some embodiments, the M36 fungalysin metalloprotease is a fragment comprising and no longer than the M36 GluZincin superfamily domain. In some embodiments, the M36 fungalysin metalloprotease is a fragment, and the propeptide FTP domain is removed (e.g., wherein amino acid residues corresponding to positions 95-141 of SEQ ID NOs: 1, 3, 5 and/or 7 are removed). In some embodiments, the M36 fungalysin metalloprotease is a fragment, and the N-terminal signal peptide and propeptide FTP domain are removed (e.g., wherein amino acid residues corresponding to positions 1-20 and 95-141 of SEQ ID NOs: 1, 3, 5 and/or 7 are removed). In some embodiments, the M36 fungalysin metalloprotease is a fragment, and the N-terminal amino acid residues 1-300 are removed. In some embodiments, the M36 fungalysin metalloprotease is a fragment, and the N-terminal amino acid residues 1-375 are removed.

In some embodiments, the therapeutic agent is a cell, a small organic molecule, small inorganic molecule, a peptide, a polypeptide or a nucleic acid. In some embodiments, the therapeutic agent is effective in the treatment, mitigation or prevention of a cancer of the central nervous system, a cancer that has metastasized to the central nervous system, or a neurodegenerative disease.

In some embodiments, the M36 fungalysin metalloprotease, or fragment thereof, is attached to a nanoparticle or a liposome. In some embodiments, the M36 fungalysin metalloprotease, or fragment thereof, is attached to the therapeutic agent, e.g., via covalent or non-covalent attachment. In some embodiments, the M36 fungalysin metalloprotease, or fragment thereof, is conjugated to the therapeutic agent. In some embodiments, the therapeutic agent is administered in conjunction with the M36 fungalysin metalloprotease intravenously. In some embodiments, the M36 fungalysin metalloprotease, or fragment thereof, is attached to or expressed within a heterologous cell (e.g., a cell that is not a *Cryptococcus* cell). In some embodiments, the M36 fungalysin metalloprotease, or fragment thereof, is attached to or expressed within a mammalian cell. In some embodiments, the M36 fungalysin metalloprotease, or fragment thereof, is attached to or expressed within a mammalian stem cell (e.g., a neural stem cell, a mesenchymal stem cell).

In some embodiments, the therapeutic agent in conjunction with a M36 fungalysin metalloprotease is administered intravenously.

In a related aspect, the invention provides expression cassettes comprising a nucleic acid encoding a M36 fungalysin metalloprotease having at least 80% sequence identity, e.g., at least about 81%, 82%, 83%, 84%, 85%, 86%, 87%, 88%, 89%, 90%, 91%, 92%, 93%, 94%, 95%, 96%, 97%, 98% or 99% sequence identity, to an amino acid sequence of SEQ ID NO: 1, or a fragment thereof that retains protease activity, operably linked to a promoter that promotes expression in a mammalian cell. In some embodiments, the promoter is a mammalian promoter. In some embodiments, the promoter is a constitutive promoter. In some embodiments, the promoter is an inducible promoter. In some embodiments, the M36 fungalysin metalloprotease is the full length enzyme. In some embodiments, the M36 fungalysin metalloprotease is a fragment comprising the peptidase_M36 domain (e.g., comprises a fragment corresponding to residues 446-722 of SEQ ID NOs: 1, 3 and/or 5 and/or corresponding to residues 446-706 of SEQ ID NO:7). In some embodiments, the M36 fungalysin metalloprotease is a fragment comprising and no longer than the peptidase_M36 domain. In some embodiments, the M36 fungalysin metalloprotease is a fragment comprising and no longer than the M36 GluZincin superfamily domain. In some embodiments, the M36 fungalysin metalloprotease is a fragment, and the propeptide FTP domain is removed (e.g., wherein amino acid residues corresponding to positions 95-141 of SEQ ID NOs: 1, 3, 5 and/or 7 are removed). In some embodiments, the M36 fungalysin metalloprotease is a fragment, and the N-terminal signal peptide and propeptide FTP domain are removed (e.g., wherein amino acid residues corresponding to positions 1-20 and 95-141 of SEQ ID NOs: 1, 3, 5 and/or 7 are removed). In some embodiments, the M36 fungalysin metalloprotease is a fragment, and the N-terminal amino acid residues 1-300 are removed. In some embodiments, the M36 fungalysin metalloprotease is a fragment, and the N-terminal amino acid residues 1-375 are removed. In some embodiments, the nucleic acid encoding the M36 fungalysin metalloprotease or fragment thereof is operably lined to a nucleic acid encoding a signal peptide the promotes the secretion and/or cell surface expression of the M36 fungalysin metalloprotease or fragment thereof.

In a further aspect, the invention provides host cells comprising the expression cassettes described herein, e.g., host cells comprising expression cassettes comprising a nucleic acid encoding a M36 fungalysin metalloprotease having at least 80% sequence identity, e.g., at least about 81%, 82%, 83%, 84%, 85%, 86%, 87%, 88%, 89%, 90%, 91%, 92%, 93%, 94%, 95%, 96%, 97%, 98% or 99% sequence identity, to an amino acid sequence of SEQ ID NOs:1, 3, 5, and/or 7, or a fragment thereof that retains protease activity, operably linked to a promoter that promotes expression in a mammalian cell. In some embodiments, the host cell is not a *Cryptococcus* cell. In some embodiments, the host cell is a mammalian cell. In some embodiments, the host cell is a stem cell. In some embodiments, the stem cell is a neuronal stem cell or a mesenchymal stem cell. In some embodiments, the stem cell is an induced pluripotent stem cell. In some embodiments, the host cell can cross the blood-brain barrier of a mammalian subject. In some embodiments, the host cell secretes the M36 fungalysin metalloprotease or fragment thereof. In some embodiments, the M36 fungalysin metalloprotease or fragment thereof is retained on the surface of the cell. In some embodiments, the M36 fungalysin metalloprotease or fragment thereof is embedded in the membrane of the cell. In some embodiments, the M36 fungalysin metalloprotease is the full length enzyme. In some embodiments, the M36 fungalysin metalloprotease is a fragment comprising the peptidase_M36 domain (e.g., comprises a fragment corresponding to residues 446-722 of SEQ ID NOs: 1, 3 and/or 5 and/or corresponding to residues 446-706 of SEQ ID NO:7). In some embodiments, the M36 fungalysin metalloprotease is a fragment comprising and no longer than the peptidase_M36 domain. In some embodiments, the M36 fungalysin metalloprotease is a fragment comprising and no longer than the M36 GluZincin superfamily domain. In some embodiments, the M36 fungalysin metalloprotease is a fragment, and the propeptide FTP domain is removed (e.g., wherein amino acid residues corresponding to positions 95-141 of SEQ ID NOs:1, 3, 5 and/or 7 are removed). In some embodiments, the M36 fungalysin metalloprotease is a fragment, and the N-terminal signal peptide and propeptide FTP domain are removed (e.g., wherein amino acid residues corresponding to positions 1-20 and 95-141 of SEQ ID NOs: 1, 3, 5 and/or 7 are removed). In some embodiments, the M36 fungalysin metalloprotease is a fragment, and the N-terminal amino acid residues 1-300 are removed. In some embodiments, the M36 fungalysin metalloprotease is a fragment, and the N-terminal amino acid residues 1-375 are removed.

In another aspect, the invention provides compositions comprising a nanoparticle or a liposome attached to a M36 fungalysin metalloprotease, wherein the M36 fungalysin metalloprotease has at least 80% sequence identity, e.g., at least about 81%, 82%, 83%, 84%, 85%, 86%, 87%, 88%, 89%, 90%, 91%, 92%, 93%, 94%, 95%, 96%, 97%, 98% or 99% sequence identity, to an amino acid sequence of SEQ ID NOs: 1, 3, 5 and/or 7, or a fragment thereof that retains protease activity. In some embodiments, the M36 fungalysin metalloprotease is the full length enzyme. In some embodiments, the M36 fungalysin metalloprotease is a fragment comprising the peptidase_M36 domain (e.g., comprises a fragment corresponding to residues 446-722 of SEQ ID NOs: 1, 3 and/or 5 and/or corresponding to residues 446-706 of SEQ ID NO:7). In some embodiments, the M36 fungalysin metalloprotease is a fragment comprising and no longer than the peptidase_M36 domain. In some embodiments, the M36 fungalysin metalloprotease is a fragment comprising and no longer than the M36 GluZincin superfamily domain. In some embodiments, the M36 fungalysin metalloprotease is a fragment, and the propeptide FTP domain is removed (e.g., wherein amino acid residues corresponding to positions 95-141 of SEQ ID NOs:1, 3, 5 and/or 7 are removed). In some embodiments, the M36 fungalysin metalloprotease is a fragment, and the N-terminal signal peptide and propeptide FTP domain are removed (e.g., wherein amino acid residues corresponding to positions 1-20 and 95-141 of SEQ ID NOs: 1, 3, 5 and/or 7 are removed). In some embodiments, the M36 fungalysin metalloprotease is a fragment, and the N-terminal amino acid residues 1-300 are removed. In some embodiments, the M36 fungalysin metalloprotease is a fragment, and the N-terminal amino acid residues 1-375 are removed. In some embodiments, the M36 fungalysin metalloprotease or fragment thereof is conjugated or covalently bound to the nanoparticle or liposome. In some embodiments, the composition is formulated in a pharmaceutically acceptable carrier. In some embodiments, the nanoparticle is a silicon nanoparticle.

Definitions

The term "*Cryptococcus*" refers to a genus of fungus. Species grow in culture as yeasts. The perfect (sexual) forms or teleomorphs of *Cryptococcus* species are filamentous fungi in the genus *Filobasidiella*. The name *Cryptococcus* is used when referring to the imperfect forms (yeast states) of the fungi. *Cryptococcus neoformans* is medically important species known for causing a severe form of meningitis and meningoencephalitis in people with HIV/AIDS. *Cryptococcus gattii* (formerly *Cryptococcus neoformans* var *gattii*) is endemic to tropical parts of the continent of Africa and Australia, and is capable of causing disease (cryptococcosis) in non-immunocompromised people.

Structurally, "mpr1" or "MPR1" refer to nucleic acids and polypeptide polymorphic variants, alleles, mutants, and interspecies homologs that: (1) have an amino acid sequence that has greater than about 80% amino acid sequence identity, for example, 81%, 82%, 83%, 84%, 85%, 86%, 87%, 88%, 89%, 90%, 91%, 92%, 93%, 94%, 95%, 96%, 97%, 98% or 99% or greater amino acid sequence identity, preferably over a region of at least about 25, 50, 100, 200, 400, 500, 800, or more amino acid residues, or over the full-length, to an MPR1 amino acid sequence, e.g., an amino acid sequence of SEQ ID NOs. 1, 3, 5 or 7. (2) bind to antibodies, e.g., polyclonal or monoclonal antibodies, raised against an immunogen comprising an amino acid sequence of a MPR1 polypeptide (e.g., MPR1 polypeptides, or fragments thereof, described herein); or an amino acid sequence encoded by a mpr1 nucleic acid (e.g., mpr1 polynucleotides described herein), and conservatively modified variants thereof; (3) specifically hybridize under stringent hybridization conditions to an anti-sense strand corresponding to a nucleic acid sequence encoding a MPR1 protein, and conservatively modified variants thereof; (4) have a nucleic acid sequence that has greater than about 80%, preferably greater than about 81%, 82%, 83%, 84%, 85%, 86%, 87%, 88%, 89%, 90%, 91%, 92%, 93%, 94%, 95%, 96%, 97%, 98%, 99%, or higher nucleotide sequence identity, preferably over a region of at least about 25, 50, 100, 200, 500, 1000, 1500 or more nucleotides, or over the full-length, to a mpr1 nucleic acid, e.g., a nucleic acid sequence of SEQ ID NOs. 2, 4, 6 or 8. An alignment of MPR1 homologs from several species is provided in FIGS. 6a-b. Based on the knowledge of MPR1 homologs, those of skill can readily determine residue positions that are more tolerant to substitution. For example, amino acid residues conserved amongst species are less tolerant of substitution or deletion. Similarly, amino acid residues that are not conserved amongst species are more tolerant of substitution or deletion, while retaining the function of the MPR1 enzyme.

The MPR1 enzyme is a M36 fungalysin metalloprotease, comprising common structural motifs, including a peptidase_M36 domain (conserved domain reference number cd09596), a M36 GluZincin superfamily domain (conserved domain reference number cd09594), a FTP (fungalysin/thermolysin propeptide) (pfam07504), and a zinc binding site. The terms "peptidase_M36 domain" and "peptidase M36 protease family" (pfam02128), also known as fungalysin (elastinolytic metalloproteinase) family, refers to endopeptidases from pathogenic fungi. Fungalysin can hydrolyze extracellular matrix proteins such as elastin and keratin, with a preference for cleavage on the amino side of hydrophobic residues with bulky side-chains. This family is similar to the M4 (thermolysin) family due to the presence of the active site residues in HEXXH and EXXXD motifs, as well as its fold prediction. Some of these enzymes also contain a protease-associated (PA) domain insert. The eukaryotic M36 and bacterial M4 families of metalloproteases also share a conserved domain in their propeptides called FTP (fungalysin/thermolysin propeptide) (pfam07504).

The term "M36 GluZincin superfamily domain" and "peptidase gluzincin family (thermolysin-like proteinases, TLPs)" refers to peptidases M1, M2, M3, M4, M13, M32 and M36 (fungalysins). Gluzincin family (thermolysin-like peptidases or TLPs) includes several zinc-dependent metallopeptidases such as the M1, M2, M3, M4, M13, M32, M36 peptidases (MEROPS classification), and contain HEXXH and EXXXD motifs as part of their active site. Peptidases in this family bind a single catalytic zinc ion which is tetrahedrally co-ordinated by three amino acid ligands and a water molecule that forms the nucleophile on activation during catalysis. Peptidase M36 (fungalysin) family includes endopeptidases from pathogenic fungi, including *Cryptococcus*. Fungalysin hydrolyzes extracellular matrix proteins such as elastin and keratin. *Cryptococcus* can cause the pulmonary disease cryptococcosis by invading the lungs of immuno-compromised animals and secreting fungalysin that possibly breaks down proteinaceous structural barriers.

The phrase "sequence identity," in the context of two nucleic acids or polypeptides, refers to two or more sequences or subsequences that have a certain level of nucleotide or amino acid residue identity, when compared and aligned for maximum correspondence, as measured using one of the following sequence comparison algorithms or by visual inspection. Preferably, the aligned sequences share at least 90% sequence identity, for example, at least 95%, 96%, 97%, 98%, 99% or 100% sequence identity. The sequence identity can exist over a region of the sequences that is at least about 10, 20 or 50 residues in length, sometimes over a region of at least about 100 or 150 residues. In some embodiments, the sequences share a certain level of sequence identity over the entire length of the sequence of interest.

For sequence comparison, typically one sequence acts as a reference sequence (e.g., SEQ ID NOs: 1-8), to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel, et al. Editor, *Current Protocols in Molecular Biology, USA,* 1984-2012). Another example of algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (on the World Wide Web at ncbi.nhn.nih.gov/) (see Henikoff & Henikoff, Proc. Natl. Acad. Sci. USA 89:10915 (1989)).

With respect to the numbering of positions in a given amino acid polymer or nucleic acid polymer, the terms "corresponding to," "corresponds to," is in "reference to," or is "relative to" the numbering of a selected amino acid polymer or nucleic acid polymer refers to the position of any given polymer component (e.g., amino acid, nucleotide, also referred to generically as a "residue") as designated by reference to the same or to an equivalent position in the selected amino acid or nucleic acid polymer, rather than by the actual numerical position of the component in the given polymer. Thus, for example, the numbering of a given amino acid position in a given polypeptide sequence corresponds to the same or equivalent amino acid position in a selected polypeptide sequence used as a reference sequence.

An "equivalent position" (for example, an "equivalent amino acid position" or "equivalent nucleic acid position" or "equivalent residue position") is defined herein as a position (such as, an amino acid position or nucleic acid position or residue position) of a test polypeptide (or test polynucleotide) sequence which aligns with a corresponding position of a reference polypeptide (or reference polynucleotide) sequence, when optimally aligned using an alignment algorithm as described herein. The equivalent amino acid position of the test polypeptide need not have the same numerical position number as the corresponding position of the reference polypeptide; likewise, the equivalent nucleic acid position of the test polynucleotide need not have the same numerical position number as the corresponding position of the reference polynucleotide.

Two polypeptide sequences are "optimally aligned" or in "optimal alignment" when they are aligned using defined parameters, i.e., a defined amino acid substitution matrix, gap existence penalty (also termed gap open penalty), and gap extension penalty, so as to arrive at the highest similarity score possible for that pair of sequences. The BLOSUM62 matrix (Henikoff and Henikoff (1992) Proc. Natl. Acad. Sci. USA 89(22):10915-10919) is often used as a default scoring substitution matrix in polypeptide sequence alignment algorithms (such as BLASTP). The gap existence penalty is imposed for the introduction of a single amino acid gap in one of the aligned sequences, and the gap extension penalty is imposed for each residue position in the gap. Unless otherwise stated, alignment parameters employed herein are: BLOSUM62 scoring matrix, gap existence penalty=11, and gap extension penalty=1. The alignment score is defined by the amino acid positions of each sequence at which the alignment begins and ends (e.g. the alignment window), and optionally by the insertion of a gap or multiple gaps into one or both sequences, so as to arrive at the highest possible similarity score.

With respect to the determination of an amino acid position by optimal alignment with a reference sequence, the amino acid position in a test amino acid sequence corresponds to the position in the reference sequence with which the residue is paired in the alignment. The "position" is denoted by a number that sequentially identifies each amino acid in the reference sequence based on its position relative to the N-terminus. Owing to deletions, insertions, truncations, fusions, and the like that must be taken into account when determining an optimal alignment, in general the amino acid residue number in a test sequence is determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

"Conservatively modified variants" as used herein applies to amino acid sequences. One of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). The term nucleic acid is used interchangeably with gene, cDNA, and mRNA encoded by a gene.

The team "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

A "constitutive" promoter is a promoter that is active under most environmental and developmental conditions. An "inducible" promoter is a promoter that is active under environmental or developmental regulation.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The terms "decrease" or "reduce" or "inhibit" interchangeably refer to the detectable reduction of a measured response (e.g., MPR1 enzymatic activity, cryptococcal infection of the CNS and/or brain tissues). The decrease, reduction or inhibition can be partial, for example, at least 10%, 25%, 50%, 75%, or can be complete (i.e., 100%). The decrease, reduction or inhibition can be measured in comparison to a control. For example, decreased, reduced or inhibited responses can be compared before and after treatment. Decreased, reduced or inhibited responses can also be compared to an untreated control, or to a known value.

The term "substrate analog" refers to a compound (e.g., small molecules) that shares structural and/or functional similarity with an enzyme substrate, but unlike the enzyme substrate, the substrate analog inhibits the function of the enzyme upon binding. A substrate analog can have structural similarity to an enzyme substrate as measured on a 2-dimensional or 3-dimensional (electron densities, location of charged, uncharged and/or hydrophobic moieties) basis. A substrate analog can have functional similarity with an enzyme substrate inasmuch as the substrate analog binds to the enzyme. A substrate analog can be a competitive inhibitor.

A "compound that inhibits MPR1 activity" refers to any compound that inhibits MPR1 activity. The inhibition can be, for example, on the transcriptional, translational or enzymatic level. Accordingly, the compound can be in any chemical form, including nucleic acid or nucleotide, amino acid or polypeptide, monosaccharide or oligosaccharide, nucleotide sugar, small organic molecule, or small inorganic molecule.

The terms "systemic administration" and "systemically administered" refer to a method of administering an antigen binding molecule that binds to MPR1 to sites in the body, including the targeted site of pharmaceutical action, via the circulatory system. Systemic administration includes, but is not limited to, oral, intranasal, rectal and parenteral (i.e., other than through the alimentary tract, such as intramuscular, intravenous, intra-arterial, transdermal and subcutaneous) administration.

The term "co-administer" and "co-administering" and variants thereof refer to the simultaneous presence of two or more active agents in the blood of an individual. The active agents that are co-administered can be concurrently or sequentially delivered.

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

The phrase "in conjunction with" when used in reference to the use of the M36 fungalysin metalloproteases (e.g., MPR1), or enzymatically active fragments thereof, described herein in conjunction with one or more therapeutic agents described herein, the active agent(s) and the other drug(s) are administered so that there is at least some chronological overlap in their physiological activity on the organism. When they are not administered in conjunction with each other, there is no chronological overlap in physiological activity on the organism. In certain preferred embodiments, the "other drug(s)" are not administered at all (e.g., not co-administered) to the organism.

The phrase "consisting essentially of" and variants thereof refer to the genera or species of active agents expressly identified in a method or composition, as well as any excipients inactive for the intended purpose of the methods or compositions.

The terms "treating" and "treatment" and variants thereof refer to delaying the onset of, retarding or reversing the progress of, alleviating or preventing either the disease or condition to which the term applies, or one or more symptoms of such disease or condition. Treating and treatment encompass both therapeutic and prophylactic treatment regimens.

The terms "subject," "patient," or "individual" interchangeably refer to any mammal, for example: humans, non-human primates (e.g., chimpanzees, or macaques), domestic mammals (e.g., canine, feline), agricultural mammals (e.g., bovine, equine, ovine, porcine) and laboratory mammals (e.g., mouse, rat, rabbit, hamster, guinea pig).

As used herein, "mammalian cells" includes reference to cells derived from mammals including humans and non-human primates (e.g., chimpanzees, or macaques), domestic mammals (e.g., canine, feline), agricultural mammals (e.g., bovine, equine, ovine, porcine) and laboratory mammals (e.g., mouse, rat, rabbit, hamster, guinea pig). The cells may be cultured in vivo or in vitro.

An "antigen binding molecule," as used herein, is any molecule that can specifically or selectively bind to an antigen. A binding molecule may include an antibody or a fragment thereof. An anti-MPR1 binding molecule is a molecule that binds to the MPR1 antigen, such as an anti-MPR1 antibody or fragment thereof. Other anti-MPR1 binding molecules may also include multivalent molecules, multi-specific molecules (e.g., diabodies), fusion molecules, aptimers, avimers, or other naturally occurring or recombinantly created molecules. Illustrative antigen-binding molecules useful to the present methods include antibody-like molecules. An antibody-like molecule is a molecule that can exhibit functions by binding to a target molecule (See, e.g., Current Opinion in Biotechnology 2006, 17:653-658; Current Opinion in Biotechnology 2007, 18:1-10; Current Opinion in Structural Biology 1997, 7:463-469; Protein Science 2006, 15:14-27), and includes, for example, DARPins (WO 2002/020565), Affibody (WO 1995/001937), Avimer (WO 2004/044011; WO 2005/040229), and Adnectin (WO 2002/032925).

An "antibody" refers to a polypeptide of the immunoglobulin family or a polypeptide comprising fragments of an immunoglobulin that is capable of noncovalently, reversibly, and in a specific manner binding a corresponding antigen.

An exemplary antibody structural unit comprises a tetramer. Each tetramer is composed of two identical pairs of polypeptide chains, each pair having one "light" (about 25 kD) and one "heavy" chain (about 50-70 kD), connected through a disulfide bond. The recognized immunoglobulin genes include the κ, λ, α, γ, δ, ε, and μ constant region genes, as well as the myriad immunoglobulin variable region genes. Light chains are classified as either κ or λ. Heavy chains are classified as γ, μ, α, δ, or ε, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain (VL) and variable heavy chain (VH) refer to these regions of light and heavy chains, respectively. As used in this application, an "antibody" encompasses all variations of antibody and fragments thereof that possess a particular binding specifically, e.g., for tumor associated antigens. Thus, within the scope of this concept are full length antibodies, chimeric antibodies, humanized antibodies, human antibodies, unibodies, single domain antibodies or nanobodies, single chain antibodies (ScFv), Fab, Fab', and multimeric versions of these fragments (e.g., F(ab')$_2$) with the same binding specificity.

Typically, an immunoglobulin has a heavy and light chain. Each heavy and light chain contains a constant region and a variable region, (the regions are also known as "domains"). Light and heavy chain variable regions contain a "framework" region interrupted by three hypervariable regions, also called "complementarity-determining regions" or "CDRs". The extent of the framework region and CDRs have been defined. See, Kabat and Wu, SEQUENCES OF PROTEINS OF IMMUNOLOGICAL INTEREST, U.S. Government Printing Office, NIH Publication No. 91-3242 (1991); Kabat and Wu, J Immunol. (1991) 147(5): 1709-19; and Wu and Kabat, *Mol Immunol.* (1992) 29(9): 1141-6. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found.

References to "VH" refer to the variable region of an immunoglobulin heavy chain, including an Fv, scFv, dsFv or Fab. References to "VL" refer to the variable region of an immunoglobulin light chain, including of an Fv, scFv, dsFv or Fab.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

The term "linker peptide" includes reference to a peptide within an antibody binding fragment (e.g., Fv fragment) which serves to indirectly bond the variable domain of the heavy chain to the variable domain of the light chain.

The term "specific binding" is defined herein as the preferential binding of binding partners to another (e.g., a polypeptide and a ligand (analyte), two polypeptides, a polypeptide and nucleic acid molecule, or two nucleic acid molecules) at specific sites. The term "specifically binds" indicates that the binding preference (e.g., affinity) for the target molecule/sequence is at least 2-fold, more preferably at least 5-fold, and most preferably at least 10- or 20-fold over a non-specific target molecule (e.g., a randomly generated molecule lacking the specifically recognized site(s); or a control sample where the target molecule or antigen is absent).

With respect to antibodies of the invention, the term "immunologically specific" "specifically binds" refers to antibodies and non-antibody antigen binding molecules that bind to one or more epitopes of a protein of interest (e.g., MPR1), but which do not substantially recognize and bind other molecules in a sample containing a mixed population of antigenic biological molecules.

The term "selectively reactive" refers, with respect to an antigen, the preferential association of an antibody, in whole or part, with a cell or tissue bearing that antigen and not to cells or tissues lacking that antigen. It is, of course, recognized that a certain degree of non-specific interaction may occur between a molecule and a non-target cell or tissue. Nevertheless, selective reactivity, may be distinguished as mediated through specific recognition of the antigen. Although selectively reactive antibodies bind antigen, they may do so with low affinity. On the other hand, specific binding results in a much stronger association between the antibody and cells bearing the antigen than between the bound antibody and cells lacking the antigen. Specific binding typically results in greater than 2-fold, preferably greater than 5-fold, more preferably greater than 10- or 20-fold and most preferably greater than 100-fold increase in amount of bound antibody (per unit time) to a cell or tissue bearing MPR1 as compared to a cell or tissue lacking MPR1.

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See, e.g., Harlow & Lane, Using Antibodies, A Laboratory Manual (1998), for a description of immunoassay formats and conditions. Preferably, the immunologically reactive conditions employed in the methods of the present invention are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

A "therapeutic moiety" is the portion of a conjugate intended to act as a therapeutic agent.

The term "therapeutic agent" includes any number of small organic compounds, small inorganic compounds, polypeptides, peptides, and nucleic acids currently known or later developed to counteract or ameliorate diseases of the CNS. In various embodiments, the therapeutic agents act as anti-neurodegeneratives, anti-neoplastics, anti-inflammatories, cytokines, anti-infectives, enzyme activators or inhibitors, allosteric modifiers, antibiotics, inhibitor nucleic acids or other agents administered to induce a desired therapeutic effect in a patient. In some embodiments, the therapeutic agent can be a chemotherapeutic agent, an anti-neoplastic agent, a cytotoxin or a radionuclide, where the therapeutic effect intended is, for example, the killing of a cancer cell.

The terms "effective amount" or "amount effective to" or "therapeutically effective amount" includes reference to a dosage of a therapeutic agent sufficient to produce a desired result.

The term "contacting" includes reference to placement in direct physical association.

The terms "conjugating," "joining," "bonding" or "linking" refer to making two polypeptides into one contiguous polypeptide molecule. In the context of the present invention, the terms include reference to joining an Mpr1 enzyme or fragment thereof to an effector molecule (EM). The linkage can be either by chemical, affinity or recombinant means, which are known in the art. Chemical means refers to a reaction between the Mpr1 enzyme or fragment thereof and the effector molecule such that there is a covalent bond formed between the two molecules to form one molecule. Biodegradable linkers are also contemplated. See, e.g., Meng, et al., *Biomaterials*. (2009) 30(12):2180-98; Duncan, *Biochem Soc Trans*. (2007) 35(Pt 1):56-60; Kim, et al., *Biomaterials*. (2011) 32(22):5158-66; and Chen, et al., *Bioconjug Chem*. (2011) 22(4):617-24.

The term "in vivo" includes reference to inside the body of the organism from which the cell was obtained. "Ex vivo" and "in vitro" means outside the body of the organism from which the cell was obtained.

The phrase "malignant cell" or "malignancy" refers to tumors or tumor cells that are invasive and/or able to undergo metastasis, i.e., a cancerous cell.

BRIEF DESCRIPTION OF THE DRAWINGS

FIGS. 2A-D illustrate that a strain of *Cryptococcus neoformans* lacking the metalloprotease (MPR1) cannot adhere to the brain endothelium in an in vitro model due to changes in the extracellular environment of the host-fungal interface. (a) To collect cells of *C. neoformans* that adhered to endothelial cells, Millipore water was added to the top transwell insert resulting in the rupture of the endothelial cells (HBMEC/D3). The attached cryptococcal cells were recovered and plated to determine CFUs. The CFUs revealed how much of the initial inoculum of the mpr1Δ strain adhered to the endothelium as compared to wild type and the reconstituted strain (MPR1), thus we were able to determine if the mpr1Δ strain had an adherence defect. Shown are CFUs representing the number of cryptococci adhering to brain endothelial cells following a 2 h incubation of wild type, mpr1Δ mutant and MPR1 strains with the endothelial barrier in the in vitro model of the BBB (blood-brain barrier). The mpr1Δ mutant strain did not adhere to brain endothelial cells (P=0.002) (b) The CFUs representing cryptococci that transmigrated to abluminal (i.e., brain) side of the barrier following a prolonged incubation with the brain endothelium revealed that the mpr1Δ mutant strain did not transmigrate. (c) Number of cryptococci that adhered to brain endothelial cells following a 20 min or an 8 h incubation of wild type and mpr1Δ mutant strains with the endothelium (P<0.0001). (d) Scanning electron micrographs of cryptococcal cells from wild type and mpr1Δ mutant strains in the presence and absence of HCMEC/D3 cells revealed that Mpr1 is altering the extracellular environment as seen by a more porous surface of cryptococci and increased blebbing on the surface of the endothelium.

FIGS. 3A-G illustrate that mammalian hosts infected with a strain of *Cryptococcus neoformans* lacking MPR1 show significant improvement in survival due to lack of fungal burden in the brain. (a) Shown is percent survival of mice inoculated via the nares mimicking the natural route of infection with wild type, mpr1Δ, and MPR1-reconstituted strains. Mpr1Δ-infected mice showed a significant improvement in survival (P=0.001) (b) CFUs representing the fungal burden at the time of death in lungs and brains (c) of mice inoculated with wild type, mpr1Δ and MPR1-reconstituted strains revealed significantly less fungal burden in brains from mice infected with mpr1Δ strain (P=0.009) but similar fungal burden in lungs. (d) Percent survival of mice inoculated via a more direct route to the brain (tail vein) with wild type and mpr1Δ mutant strains revealed a dramatic improvement in survival of mice infected with mpr1Δ strain. (e) CFUs representing the fungal burden in brains of mice following 12 h, 24 h, 48 h and (f) 16 days post-infection with wild type and mpr1Δ mutant strains revealed significantly less fungal burden in brains of mice infected with mpr1Δ strain. The lack of brain pathology in these same mice suggested that the brain CFUs observed at 12 h post-infection (e) reflected mpr1Δ cells lingering in the vessels unable to penetrate the brain endothelium. (g) The number of cryptococci that survived within brain parenchyma of mice following inoculation by direct intracranial injection of wild type and mpr1Δ mutant strains revealed no significant difference between strains.

FIGS. 4A-H illustrate that mammalian hosts infected with the mpr1Δ null mutant strain of *Cryptococcus neoformans* lack the brain pathology that is commonly associated with fungal disease of the CNS. Mice were inoculated by tail vein injection and brains were examined at 12 h, 24 h and 48 h post-infection by taking 20 consecutive, longitudinal brain sections and staining with mucicarmine (specific for cryptococci) or hematoxylin and eosin (H&E). Histological analysis of brain slices from brains of mice inoculated by tail vein with the wild type strain (a, c, e, g) revealed a significant number of lesions filled with cryptococci at various stages of cell division (arrows point to cryptococci within lesions) consistent with fungal disease of the central nervous system. However, brain sections from mice infected with the mpr1Δ mutant strain (b, d, f, h) at 48 h post-infection (a, d), 24 h post-infection (f) and 12 h post-infection (h) revealed a complete absence of cryptococci-filled lesions indicating no brain pathology.

FIGS. 5A-F illustrate that wild-type (WT), mutant (mpr1Δ) and reconstituted (Rec1) strain #1 have comparable growth in minimal media (synthetic dextrose-SD) at 30° C. and comparable growth in rich media (yeast extract peptone dextrose-YPD) at both 30° C. and 37° C. (a, b, c). *Cryptococcus neoformans* var. *grubii* serotype A clinical strain H99 was used as the wild-type strain. The mpr1Δ null mutant strain and MPR1-reconstituted strains were made in the H99 background strain (a gift from J. Lodge) and the mutant was obtained from the *C. neoformans* orf deletion library (ATCC). Three reconstituted strains were selected for analysis and strain #1 was selected for all subsequent studies based on its comparable growth with both wild type and mpr1Δ strains. (d) Genomic DNA from WT and mpr1Δ strains was digested with AAT II and Age I while DNA from Rec1 was digested with two sets of enzymes AAT II and Age I (Rec1a) or AAT II and Pml I (Rec1b). Digested DNA was fractionated on agarose gel, transferred to nylon membrane, and incubated with a digoxigenin-labelled probe (Primers F-ACTTCCAGGCTTACAATTTCAG, Primers R-AG-ATTTGGTCGGCCT GAATGATCG) spanning a region of MPR1 that was deleted from the mpr1Δ strain. A single band was observed for the WT and Rec1 strains while no bands were detected for the mpr1Δ strain. The presence of one band for the Rec1 strain indicated that only one integration of a wild-type copy of MPR1 took place during the biolistic transformation process. (e, f) Wild type and mpr1Δ cells were incubated with the macrophage cell line J774A.1 for 1 h in the presence of interferon gamma (IFN-γ), lipopolysaccharide (LPS) and mAb18B7, washed to remove non-specific binding of yeast cells, and incubated with macrophage for a total of 24 h. Macrophages were lysed with water and plated for CFU enumeration. Innoculum was defined as the number of adherent cells after 1 h of incubation with J774A.1. Inoculum dose was determined by carrying a parallel set of experiments where instead of letting the experiment continue for 24 h after the 1 h washing step, the macrophages were lysed for CFU enumeration of adherent yeast cells.

FIGS. 6A-B illustrate an amino acid sequence alignment of MPR1 metalloprotease expressed by *Cryptococcus* strains CNBJ1810 (SEQ ID NO:1), CNJ01650 (SEQ ID NO:3), CGB_I230C (SEQ ID NO:5), and CNAG_0735.2 (SEQ ID NO:7), as well as a consensus amino acid sequence (bottom row). Conserved amino acid residues are less tolerant to substitution or deletion, and non-conserved amino acid residues are more tolerant to substitution or deletion.

FIGS. 7A-D illustrate iTRAQ proteomic analysis workflow for identifying substrates of MPR1 (identified as mp102Δ). A and B; in the presence of endothelial cells; C and D; cryptococcal cells alone.

FIGS. 8A-C illustrate the expression of the metalloprotease gene (Mpr1) into a wild type strain of yeast (*Saccharomyces cerevisiae*) enabled the transformed yeast to cross the brain endothelium. (a) An in vitro model of the blood-brain barrier was used to examine the ability of non-pathogenic yeast to cross the brain endothelium by performing transcytosis assays. HCMEC/D3 cells were grown as a monolayer on transwell inserts submerged in media specific for endothelial cells such that the luminal and abluminal sides represented the blood and brain sides, respectively. Strains were added to the luminal side and collected from the abluminal side 24 h later for CFU determination. (b) A wild type strain of *S. cerevisiae* was engineered to express the cDNA of Mpr1 from *Cryptococcus neoformans* var. *grubii* (H99). RT-PCR revealed the expression of the CnMpr1 cDNA in yeast (lane 5). Lane 4 revealed that *S. cerevisiae* does not normally express Mpr1. Lane 3, demonstrated that the Cnmpr1Δ null mutant does not express Mpr1 transcript as expected. Lane 6, 7, and 8 represent positive controls. (c) Transcytosis assays revealed that a yeast strain alone did not cross the brain endothelium (indicated at Sc) but the yeast strain expressing cDNA of Mpr1 from *C. neoformans* (indicated as Sc<MPR1>) had gained the ability to cross the brain endothelium.

DETAILED DESCRIPTION

1. Introduction

Figure 1A:
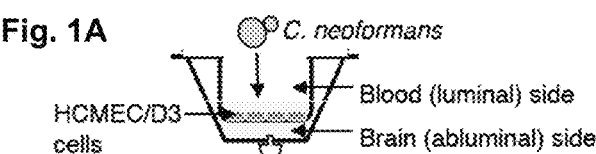
FIGS. 1A-E illustrate that a newly identified metalloprotease fails to breach the brain endothelium in an in vitro model of the blood-brain barrier (BBB). (a) A schematic representation of the in vitro model of the BBB. HCMEC/D3 cells were grown as a monolayer on transwell inserts submerged in media specific for endothelial cells such that the luminal and abluminal sides represented the blood and brain sides, respectively. Cryptococci were added to the luminal side and collected from the abluminal side for CFU determination. (b) Strains of *C. neoformans* lacking the genes encoding various proteases were tested for their ability to transmigrate the brain endothelium in the in vitro model of the BBB. The strain D102 (mpr1Δ mutant strain) was defective in crossing the endothelial barrier (P=0.009). (c) CFUs representing cryptococci of wild type and mpr1Δ mutant strains able to proliferate in HCMEC/D3 growth media in the absence of endothelial cells. Both strains tolerate the growth conditions for HCMEC/D3 to a similar degree. (d) Mpr1 is an extracellular protein. We constructed an MPR1-dsRED fusion protein and expressed it in the mpr1Δ background strain to access its localization. Fluorescence microscopy of an MPR1-dsRED fusion protein under the control of an ACTIN promoter expressed in the mpr1Δ mutant strain, revealed a surface localization. (e) A schematic diagram of the predicted structure of MPR1 illustrates the N-terminal signal, the predicted prodomain, the peptidase M36 domain with the conserved metal-binding site.

Immunocompromised populations worldwide are at risk for developing a life-threatening infection of the brain caused by *Cryptococcus neoformans*, a pathogenic fungus. See, e.g., World Health Organization. (2003) HIV/AIDS Epidemiological surveillance update for the W.H.O. African region. World Health Organization, Geneva, Switzerland; Mitchell, et al., (1995) *Clin. Microbiol. Rev.* 8:515-548; Sorvillo, et al., (1997) *AIDS* 11, 673-679; Bicanic, et al., (2004) *British Med. Bulletin*, 72, 99-118; Zuger, et al., (1986) *Ann Intern Med* 104:234-240; Casadevall and Perfect (1998) *Cryptococcus neoformans*. American Society for Microbiology, Washington, D.C.; and Ecevit, et al., (2006) *Clin Infect Dis* 42:1443-1447. Why *C. neoformans* has this remarkable tropism for the central nervous system (CNS) is not clear. Recent research on cerebral pathogenesis of *C. neoformans* revealed a predominantly transcellular migration of cryptococci across the brain endothelium. See, e.g., Chang, et al., (2004) *Infect Immun* 72:4985-4995; Vu, et al., (2009) *Eukaryotic Cell* 8:1803-1807; and Shi, et al., (2010) *J. Clinical Invest* 120:1683-1693. The identity of key fungal virulence factors that function specifically to invade the CNS remains unresolved. The present invention is based, in part, on the discovery of a metalloprotease (MPR1) through our examination of the extracellular proteome of *C. neoformans* (Eigenheer, et al., (2007) *FEMS Yeast Research* 7:499-510) and the finding that MPR1 is required for establishing fungal disease in the CNS. A strain of *C. neoformans* lacking the gene encoding MPR1 (mpr1Δ) failed to breach the endothelium in an in vitro model of the blood-brain barrier (BBB). Also, infection of a mammalian host with the mpr1Δ null mutant strain greatly improved survival due to a significantly reduced fungal burden in the brain. The brain pathology commonly associated with cryptococcal disease was not detected in brains from hosts infected with the mpr1Δ strain. The central role of MPR1 in the pathogenesis of CNS cryptococcosis provides a target for preventing, reducing, delaying and/or inhibiting *Cryptococcus neoformans* infection of the CNS.

2. Methods of Preventing, Reducing, Delaying and/or Inhibiting *Cryptococcus neoformans* Infection of the CNS a. Subjects Who May Benefit Subjects who may benefit from methods of inhibiting the activity of the fungal-specific MPR1 metalloprotease may already have or be suspected of having a *Cryptococcus* infection, or may be at risk of developing a *Cryptococcus* infection.

In subjects who may already have or be suspected of having a *Cryptococcus* infection, administration of an agent that inhibits the activity of the fungal-specific MPR1 metalloprotease can ameliorate progression of infection, reduce further infection of the CNS and/or the brain tissues, and/or prevent penetration and crossing of the blood-brain-barrier by *Cryptococcus* organisms. The subject may or may not be exhibiting symptoms of *Cryptococcus* infection (e.g., a cough that lasts weeks or months, sharp chest pains, unexplained shortness of breath, severe headache, confusion, fever, night sweats, and/or unintended weight loss). In some embodiments, the subject has no detectable *Cryptococcus* infection of the CNS and/or in the brain tissues. In various embodiments, the subject may have, be suspected of having and/or exhibiting symptoms of pulmonary cryptococcosis or cryptococcal endocarditis. In various embodiments, the subject may have, be suspected of having and/or exhibiting symptoms of cryptococcal meningitis.

Subjects at risk of developing a *Cryptococcus* infection include those with compromised immunity, e.g., resulting from HIV infection, cancer chemotherapy, immunosuppressant therapy, and/or metabolic immunosuppression. Subjects at risk of developing a *Cryptococcus* infection also include those in an environment or geographical location that increases the risk of contracting a Cryptococcal infection, e.g., in Africa, India, Thailand and other Asian-Pacific countries, and the North American Pacific Northwest, including Canada and the U.S (e.g., Washington, Oregon, Northern California).

In some embodiments, the subject has tested positive in a serum assay for detecting for *Cryptococcus* infection. For example, the subject may have tested positive for *Cryptococcus* infection in the cryptococcal antigen lateral flow assay (CrAg LFA). See, e.g., Lindsley, et al., *Clin Infect Dis*. (2011) 53(4):321-5.

In various embodiments, the subject is infected with, suspected of being infected with, or at risk of being infected with a *Cryptococcus* species selected from the group consisting of *Cryptococcus gattii, Cryptococcus neoformans, Cryptococcus neoformans* var. *grubii, Cryptococcus neoformans* var *grubii* H99, *Cryptococcus* sp. Y13-1, *Cryptococcus laurentii* and *Cryptococcus albidus*.

b. Inhibiting the Metalloprotease Activity of MPR1

MPR1 activity can be inhibited at either or both the protein level or the transcriptional level. In various embodiments, an agent that inhibits the enzymatic or catalytic activity or substrate binding activity of a fungal-specific MPR1 protein is administered. In some embodiments, an agent that inhibits the expression, e.g., the transcription and or translation of a fungal-specific MPR1 protein is administered.

i. *Cryptococcus* MPR1 Metalloproteases to be Inhibited

Generally, the metalloprotease activity of a MPR1 or *Cryptococcus* M36 fungalysin metalloprotease, e.g., having at least 80% sequence identity, e.g., at least about 85%, 90%, 91%, 92%, 93%, 94%, 95%, 96%, 97%, 98% or 99% sequence identity, to an amino acid sequence of SEQ ID NOs: 1, 3, 5 or 7, is inhibited or reduced, thereby preventing, reducing, delaying or inhibiting transmigration of *Cryptococcus* across the blood-brain-barrier and into the CNS. In some embodiments, the M36 fungalysin metalloprotease has an amino acid sequence of SEQ ID NOs: 1, 3, 5 or 7.

In various embodiments, the MPR1 metalloprotease or *Cryptococcus* M36 fungalysin metalloprotease to be reduced or inhibited is from a *Cryptococcus* species or strain selected from *Cryptococcus gattii, Cryptococcus neoformans, Cryptococcus neoformans* var. *grubii, Cryptococcus neoformans* var *grubii* H99, *Cryptococcus* sp. Y13-1, *Cryptococcus laurentii* and *Cryptococcus albidus*.

ii. Inhibiting MPR1 Enzymatic Activity

In one embodiment, the methods involve reducing, inhibiting or preventing penetration and crossing of the blood-brain-barrier by *Cryptococcus* and cryptococcal infection of the CNS and/or brain tissues by inhibiting a fungal-specific MPR1 metalloprotease. Preferably, the inhibitory agent specifically or preferentially inhibits the metalloprotease activity of a *Cryptococcus*-specific MPR1 in comparison to inhibiting the metalloprotease activity of metalloproteases endogenous to the subject.

Examples of agents capable of inhibiting enzyme activity include substrate analogs, suicide substrates, alkylating agents, and inhibitory nucleic acids (reviewed in Ferscht, Structure and Mechanism in Protein Science: A Guide to Enzyme Catalysis and Protein Folding, 3rd Edition, 1999, W.H. Freeman & Co.). The methods of decreasing, inhibiting or preventing MPR1 activity can involve administering to a subject, including a mammal such as a human, a compound that is an analog of a substrate for a fungal-specific or *Cryptococcus*-specific MPR1, including small organic compound or peptidomimetic substrate analogs.

The preferred MPR1 inhibitors have no other adverse effects on cellular metabolism, so that other cellular functions proceed while the specific reaction of MPR1 metalloprotease activity is inhibited. The blocking agents are preferably relatively small molecules, thereby avoiding immunogenicity and allowing passage through the cell membrane. Ideally, they have a molecular weight of between about 100-2000 daltons, but may have molecular weights up to 5000 or more, depending upon the desired application. In most preferred embodiments, the inhibitors have molecular weights of between about 200-600 daltons.

The inhibitors of the present invention preferably have strong affinity for the target enzyme, so that at least about 60-70% inhibition of MPR1 activity is achieved, more preferably about 75%-85% and most preferably 90%-95% or more. In some embodiments, the inhibitors will completely inhibit MPR1 activity. The affinity of the enzyme for the inhibitor is preferably sufficiently strong that the dissociation constant, or $K_i$, of the enzyme-inhibitor complex is less than about $10^{-5}$ M, typically between about $10^{-6}$ and $10^{-8}$M.

Enzyme inhibition generally involves the interaction of a substance with an enzyme so as to decrease the rate of the reaction catalyzed by that enzyme. Inhibitors can be classified according a number of criteria. For example, they may be reversible or irreversible. An irreversible inhibitor dissociates very slowly, if at all, from its target enzyme because it becomes very tightly bound to the enzyme, either covalently or noncovalently. Reversible inhibition, in contrast, involves an enzyme-inhibitor complex which may dissociate.

Inhibitors can also be classified according to whether they are competitive, noncompetitive or uncompetitive inhibitors. In competitive inhibition for kinetically simple systems involving a single substrate, the enzyme can bind either the substrate or the inhibitor, but not both. Typically, competitive inhibitors resemble the substrate or the product(s) and bind the active site of the enzyme, thus blocking the substrate from binding the active site. A competitive inhibitor diminishes the rate of catalysis by effectively reducing the affinity of the substrate for the enzyme. Typically, an enzyme may be competitively inhibited by its own product because of equilibrium considerations. Since the enzyme is a catalyst, it is in principle capable of accelerating a reaction in the forward or reverse direction.

Noncompetitive inhibitors allow the enzyme to bind the substrate at the same time it binds the inhibitor. A noncompetitive inhibitor acts by decreasing the turnover number of an enzyme rather than diminishing the proportion of free enzyme. Another possible category of inhibition is mixed or uncompetitive inhibition, in which the inhibitor affects the binding site and also alters the turnover number of the enzyme. Enzyme inhibition of kinetically complex systems involving more than one substrate, as can be the case for MPR1 enzymes, are described in Segel, Enzyme Kinetics, (Wiley, N.Y. 1975).

MPR1 metalloprotease activity and its inhibition or enhancement is typically assayed according to standard methods for determining enzyme activity. For a general discussion of enzyme assays, see, Rossomando, "Measurement of Enzyme Activity" in Guide to Protein Purification, Vol. 182, Methods in Enzymology (Deutscher ed., 1990). Assays for the measurement of MPR1 metalloprotease activity are described herein, and for example, in Naumann, et al., (2011) *J Biol Chem*, August 30 (PMID:21878653); Monod, et al., (1993) *Infect. & Immun.* 61:4099-4104; and Markaryan, A., et al., (1994) *Infect. & Immun.* 62:2149-2157.

An assay for measuring MPR1 metalloprotease activity typically contains a buffered solution adjusted to physiological pH. General proteolytic activity of MPR1 can be measured employing a casein assay (azocasein). The substrate (e.g., azocasein) is dissolved in a buffered solution of about neutral pH and added to the enzyme (Mpr1) sample. The hydrolysis of the azo dye into the supernatant is detected by absorbance at 440 nm and the proteolytic activity of MPR1 is expressed in arbitrary units. When testing for the ability of a test compound to decrease or inhibit MPR1 metalloprotease activity, the metalloprotease activity of an MPR1 enzyme exposed to the test compound is compared to the metalloprotease activity of an MPR1 enzyme in a control unexposed to the test compound.

1. Anti-MPR1 Antigen Binding Molecule Inhibitors

Antigen binding molecules that bind to and reduce or inhibit the metalloprotease activity of a MPR1 or *Cryptococcus* M36 fungalysin metalloprotease can be non-antibody binding molecules, or antibodies and fragments thereof. The antigen binding molecules can bind to any region of the enzyme that inhibits or reduces its metalloprotease activity, e.g., by interfering directly with catalytic activity or substrate binding. In various embodiments, the antigen binding molecule binds to the peptidase_M36 domain of the M36 fungalysin metalloprotease. In some embodiments, the antigen binding molecule binds to the M36 GluZincin superfamily domain of the M36 fungalysin metalloprotease. In some embodiments, the antigen binding molecule binds to the zinc binding site of the M36 fungalysin metalloprotease.

a. Non-Antibody Antigen Binding Molecules

In various embodiments, the antigen binding molecule is a non-antibody binding protein. Protein molecules have been developed that target and bind to targets in a manner similar to antibodies. Certain of these "antibody mimics" use non-immunoglobulin protein scaffolds as alternative protein frameworks for the variable regions of antibodies.

For example, Ladner et al. (U.S. Pat. No. 5,260,203) describe single polypeptide chain binding molecules with binding specificity similar to that of the aggregated, but molecularly separate, light and heavy chain variable region of antibodies. The single-chain binding molecule contains the antigen binding sites of both the heavy and light variable regions of an antibody connected by a peptide linker and will fold into a structure similar to that of the two peptide antibody. The single-chain binding molecule displays several advantages over conventional antibodies, including, smaller size, greater stability and are more easily modified.

Ku et al. (Proc. Natl. Acad. Sci. U.S.A. 92(14):6552-6556 (1995)) discloses an alternative to antibodies based on cytochrome b562. Ku et al. (1995) generated a library in which two of the loops of cytochrome b562 were randomized and selected for binding against bovine serum albumin. The individual mutants were found to bind selectively with BSA similarly with anti-BSA antibodies.

Lipovsek el al. (U.S. Pat. Nos. 6,818,418 and 7,115,396) discloses an antibody mimic featuring a fibronectin or fibronectin-like protein scaffold and at least one variable loop. Known as Adnectins, these fibronectin-based antibody mimics exhibit many of the same characteristics of natural or engineered antibodies, including high affinity and specificity for any targeted ligand. Any technique for evolving new or improved binding proteins can be used with these antibody mimics.

The structure of these fibronectin-based antibody mimics is similar to the structure of the variable region of the IgG heavy chain. Therefore, these mimics display antigen binding properties similar in nature and affinity to those of native antibodies. Further, these fibronectin-based antibody mimics exhibit certain benefits over antibodies and antibody fragments. For example, these antibody mimics do not rely on disulfide bonds for native fold stability, and are, therefore, stable under conditions which would normally break down antibodies. In addition, since the structure of these fibronectin-based antibody mimics is similar to that of the IgG heavy chain, the process for loop randomization and shuffling can be employed in vitro that is similar to the process of affinity maturation of antibodies in vivo.

Beste et al. (Proc. Natl. Acad. Sci. U.S.A. 96(5): 1898-1903 (1999)) discloses an antibody mimic based on a lipocalin scaffold (Anticalin®). Lipocalins are composed of a β-barrel with four hypervariable loops at the terminus of the protein. Beste (1999), subjected the loops to random mutagenesis and selected for binding with, for example, fluorescein. Three variants exhibited specific binding with fluorescein, with one variant showing binding similar to that of an anti-fluorescein antibody. Further analysis revealed that all of the randomized positions are variable, indicating that Anticalin® would be suitable to be used as an alternative to antibodies. Anticalins® are small, single chain peptides, typically between 160 and 180 residues, which provide several advantages over antibodies, including decreased cost of production, increased stability in storage and decreased immunological reaction.

Hamilton et al. (U.S. Pat. No. 5,770,380) discloses a synthetic antibody mimic using the rigid, non-peptide organic scaffold of calixarene, attached with multiple variable peptide loops used as binding sites. The peptide loops all project from the same side geometrically from the calixarene, with respect to each other. Because of this geometric confirmation, all of the loops are available for binding, increasing the binding affinity to a ligand. However, in comparison to other antibody mimics, the calixarene-based antibody mimic does not consist exclusively of a peptide, and therefore it is less vulnerable to attack by protease enzymes. Neither does the scaffold consist purely of a peptide, DNA or RNA, meaning this antibody mimic is relatively stable in extreme environmental conditions and has a long life span. Further, since the calixarene-based antibody mimic is relatively small, it is less likely to produce an immunogenic response.

Murali et al. (Cell. Mol. Biol. 49(2):209-216 (2003)) discusses a methodology for reducing antibodies into smaller peptidomimetics, they term "antibody like binding peptidomimetics" (ABiP) which can also be useful as an alternative to antibodies.

Silverman el al. (Nat. Biotechnol. (2005), 23: 1556-1561) discloses fusion proteins that are single-chain polypeptides comprising multiple domains termed "avimers." Developed from human extracellular receptor domains by in vitro exon shuffling and phage display the avimers are a class of binding proteins somewhat similar to antibodies in their affinities and specificities for various target molecules. The resulting multidomain proteins can comprise multiple independent binding domains that can exhibit improved affinity (in some cases sub-nanomolar) and specificity compared with single-epitope binding proteins. Additional details concerning methods of construction and use of avimers are disclosed, for example, in U.S. Patent App. Pub. Nos. 20040175756, 20050048512, 20050053973, 20050089932 and 20050221384.

In addition to non-immunoglobulin protein frameworks, antibody properties have also been mimicked in compounds comprising RNA molecules and unnatural oligomers (e.g., protease inhibitors, benzodiazepines, purine derivatives and beta-turn mimics) all of which are suitable for use with the present invention.

b. Anti-MPR1 Antibodies

In various embodiments, the antigen binding molecule is an antibody or antibody fragment that binds to MPR1 and inhibits the metalloprotease activity of MPR1. Such anti-MPR1 antibodies are useful for preventing, delaying, inhibiting and treating the progression of a *Cryptococcus* infection and infection of the CNS and/or brain tissues of a subject by *Cryptococcus*.

An antibody suitable for treating, mitigating, delaying and/or preventing *Cryptococcus* infection in a subject is specific for at least one portion of the MPR1 polypeptide, e.g., the catalytic domain. For example, one of skill in the art can use peptides derived from the catalytic domain of a fungal-specific MPR1 to generate appropriate antibodies suitable for use with the invention. Illustrative, non-limiting amino sequences suitable for use in selecting peptides for use as antigens are published as GenBank accession numbers XP_567342.1 (*Cryptococcus neoformans* var. *neoformans*), XP_003196170.1 (*Cryptococcus gattii*), as well as SEQ ID NOs. 1, 3, 5 and 7.

Anti-MPR1 antibodies for use in the present methods include without limitation, polyclonal antibodies, monoclonal antibodies, chimeric antibodies, humanized antibodies, human antibodies, and fragments thereof.

The preparation of polyclonal antibodies is well-known to those skilled in the art. See, for example, Green et al., Production of Polyclonal Antisera, in IMMUNOCHEMICAL PROTOCOLS (Manson, ed), pages 1-5 (Humana Press 1992), Coligan et al, Production of Polyclonal Antisera in Rabbits, Rats. Mice and Hamsters, in CURRENT PROTOCOLS IN IMMUNOLOGY, section 2 4 1 (1992), which are hereby incorporated by reference.

The preparation of monoclonal antibodies likewise is conventional. See, for example, Kohler & Milstem, Nature 256 495 (1975). Coligan et al., sections 2.5.1-2.6.7, Harlow et al, ANTIBODIES A LABORATORY MANUAL, page 726 (Cold Spring Harbor Pub 1988, and Harlow, USING ANTIBODIES A LABORATORY MANUAL, Cold Spring Harbor Laboratory Press, 1998), which are hereby incorporated by reference Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e g., Coligan et al. sections 2.7.1-2.7.12 and sections 2.9.1-2.9.3, Barnes et al., Purification of Immunoglobulin G (IgG), in METHODS IN MOLECULAR BIOLOGY, VOL 10, pages 79-104 (Humana Press 1992).

Methods of in vitro and in vivo multiplication of monoclonal antibodies is well-known to those skilled in the art Multiplication in vitro can be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo can be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Anti-MPR1 antibodies can be altered or produced for therapeutic applications. For example, antibodies of the present invention can also be derived from subhuman primate antibody. General techniques for raising therapeutically useful antibodies in baboons can be found, for example, in Goldenberg et al., International Patent Publication WO 91/11465 (1991) and Losman et al., Int. J. Cancer 46:310 (1990), which are hereby incorporated by reference.

Alternatively, therapeutically useful anti-MPR1 antibodies can be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi, et al., Proc. Nat'l Acad. Sci. USA 86:3833 (1989), which is hereby incorporated in its entirety by reference. Techniques for producing humanized monoclonal antibodies are described, for example, by Jones et al., Nature 321:522 (1986); Riechmann et al., Nature 332:323 (1988); Verhoeyen et al., Science 239:1534 (1988); Carter et al. Proc. Nat'l Acad. Sci. USA 89:4285 (1992); Sandhu, Crit.

Rev. Biotech. 12:437 (1992); and Singer et al., J. Immunol. 150:2844 (1993), which are hereby incorporated by reference.

Anti-MPR1 antibodies for use in the present methods also can be derived from human antibody fragments isolated from a combinatorial immunoglobulin library. See, for example, Barbas, et al., METHODS: A COMPANION TO METHODS IN ENZYMOLOGY, VOL. 2, page 119 (1991); Winter et al., Ann. Rev. Immunol. 12:433 (1994), which are hereby incorporated herein by reference. Cloning and expression vectors that are useful for producing a human immunoglobulin phage library can be obtained, for example, from STRATAGENE Cloning Systems (now Agilent Technologies).

In addition, anti-MPR1 antibodies for the mitigation, delay, treatment and/or prevention of *Cryptococcus* infection of the CNS and/or brain tissues can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994); Lonberg et al. Nature 368:856 (1994); and Taylor et al., Int. Immunol. 6:579 (1994), which are hereby incorporated by reference.

In various embodiments, the antibodies are human IgG immunoglobulin. As appropriate or desired, the IgG can be of an isotype to promote antibody-dependent cell-mediated cytotoxicity (ADCC) and/or complement-dependent cellular cytotoxicity (CDCC), e.g., human IgG1 or human IgG3.

Antibody fragments for use in the present methods can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a fragment denoted $F(ab')_2$—This fragment can be further cleaved using a thiol reducing agent, and optionally a blocking group for the sulfhydryl groups resulting from cleavage of disulfide linkages, to produce Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein. These patents are hereby incorporated in their entireties by reference. See also, Nisonhoff, et al., Arch. Biochem. Biophys. 89:230 (1960); Porter, Biochem. J. 73:119 (1959): Edelman et al., METHODS IN ENZYMOLOGY, VOL. 1, page 422 (Academic Press 1967); and Coligan et al. at sections 2.8.1-2.8.10 and 2.10.1-2.10.4.

Other methods of cleaving antibodies, such as separation of heavy chains to form monovalent light-heavy chain fragments, further cleavage of fragments, or other enzymatic, chemical, or genetic techniques can also be used, so long as the fragments bind to the antigen that is recognized by the intact antibody.

For example, Fv fragments comprise an association of VH and VL chains. This association can be noncovalent, as described in Inbar et al., Proc. Nat'l Acad. Sci. USA 69:2659 (1972). Alternatively, the variable chains can be linked by an intermolecular disulfide bond or cross-linked by chemicals such as glutaraldehyde. See. e.g. Sandhu, *Crit Rev Biotechnol.* 1992; 12(5-6):437-62. In some embodiments, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFv are described, for example, by Whitlow et al, METHODS: A COMPANION TO METHODS IN ENZYMOLOGY, VOL. 2, page 97 (1991); Bird et al, Science 242:423-426 (1988); Ladner, et al, U.S. Pat. No. 4,946,778; Pack, et al, BioTechnology 11:1271 77 (1993); and Sandhu, supra.

Another form of an antibody fragment suitable for use with the methods of the present invention is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al, METHODS: A COMPANION TO METHODS IN ENZYMOLOGY, VOL. 2, page 106 (1991), iv. Small Organic Compounds.

In some embodiments, the anti-MPR1 antibody is a single-domain antibody (sdAb) or a nanobody. A single-domain antibody or a nanobody is a fully functional antibody that lacks light chains; they are heavy-chain antibodies containing a single variable domain (VHH) and two constant domains (CH2 and CH3). Like a whole antibody, single domain antibodies or nanobodies are able to bind selectively to a specific antigen. With a molecular weight of only 12-15 kDa, single-domain antibodies are much smaller than common antibodies (150-160 kDa) composed of two heavy protein chains and two light chains, and even smaller than Fab fragments (~50 kDa, one light chain and half a heavy chain) and single-chain variable fragments (~25 kDa, two variable domains, one from a light and one from a heavy chain). Nanobodies are more potent and more stable than conventional four-chain antibodies which leads to (1) lower dosage forms, less frequent dosage leading to less side effects; and (2) improved stability leading to a broader choice of administration routes, comprising oral or subcutaneous routes and slow-release formulations in addition to the intravenous route. Slow-release formulation with stable anti-MPR1 nanobodies, find use for the mitigation, delay, treatment and prevention of *Cryptococcus* infection of the CNS and/or brain, avoiding the need of repeated injections and the side effects associated with it. Because of their small size, nanobodies have the ability to cross membranes and penetrate into physiological compartments, tissues and organs not accessible to other, larger polypeptides and proteins.

Preferably, the antibodies are humanized for use in treating or preventing *Cryptococcus* infections in humans.

iii. Inhibiting MPR1 Expression

Decreasing or inhibiting MPR1 gene expression can be achieved using any method in the art, including through the use of inhibitory nucleic acids (e.g., small interfering RNA (siRNA), micro RNA (miRNA), antisense RNA, ribozymes, etc.). Inhibitory nucleic acids can be single-stranded nucleic acids that can specifically bind to a complementary nucleic acid sequence. By binding to the appropriate target sequence, an RNA-RNA, a DNA-DNA, or an RNA-DNA duplex or triplex is formed. Such inhibitory nucleic acids can be in either the "sense" or "antisense" orientation. See, for example, Tafech, et al., Curr Med Chem (2006) 13:863-81; Mahato, et al., Expert Opin Drug Deliv (2005) 2:3-28; Scanlon, Curr Pharm Biotechnol (2004) 5:415-20; and Scherer and Rossi, Nat Biotechnol (2003) 21:1457-65.

In one embodiment, the inhibitory nucleic acid can specifically bind to a target nucleic acid sequence or subsequence that encodes a *Cryptococcus* MPR1. Administration of such inhibitory nucleic acids can decrease or inhibit the metalloprotease activity of MPR1 and consequently, cryptococcal infection of the CNS and/or brain tissues. Nucleotide sequences encoding a *Cryptococcus* MPR1 are known for several *Cryptococcus* MPR1 species, including e.g., nucleic acid sequences of SEQ ID NOs. 2, 4, 6 and 8, and nucleic acid sequences encoding the MPR1 metalloproteases of GenBank references XP_567342.1 (*Cryptococcus neoformans* var. *neoformans*), XP_003196170.1 (*Cryptococcus gattii*), as well as SEQ ID NOs. 1, 3, 5 and 7. From these nucleotide sequences, one can derive a suitable inhibitory nucleic acid.

1. Antisense Oligonucleotides

In some embodiments, the inhibitory nucleic acid is an antisense molecule. Antisense oligonucleotides are relatively short nucleic acids that are complementary (or antisense) to the coding strand (sense strand) of the mRNA encoding a fungal specific MPR1. Although antisense oligonucleotides are typically RNA based, they can also be DNA based. Additionally, antisense oligonucleotides are often modified to increase their stability.

Without being bound by theory, the binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell or tissue allows the degradation of the mRNA encoding a *Cryptococcus* MPR1. Accordingly, antisense oligonucleotides decrease the expression and/or activity of MPR1.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO 88/09810) or the blood-brain barrier (see, e.g., PCT Publication No. WO 89/10134), hybridization-triggered cleavage agents (See, e.g., Krol et al., 1988, BioTechniques 6:958-976) or intercalating agents. (See, e.g., Zon, 1988, Pharm. Res. 5:539-549). To this end, the oligonucleotide can be conjugated to another molecule.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxytriethyl) uracil, 5-carboxymethylaminomethyl-2-thiouridine, 5-carboxymethyl aminomet-hyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methyl aminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an-anomeric oligonucleotide. An anomeric oligonucleotide forms specific double-stranded hybrids with complementary RNA in which, contrary to the usual-units, the strands run parallel to each other (Gautier et al., 1987, Nucl. Acids Res. 15:6625-6641). The oligonucleotide is a 2'-O-methylribonucleotide (Inoue et al., 1987, Nucl. Acids Res. 15:6131-6148), or a chimeric RNA-DNA analogue (Inoue et al., 1987, FEBS Lett. 215:327-330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448-7451), etc.

The selection of an appropriate oligonucleotide can be readily performed by one of skill in the art. Given the nucleic acid sequence encoding a fungal-specific MPR1, one of skill in the art can design antisense oligonucleotides that bind to a target nucleic acid sequence and test these oligonucleotides in an in vitro or in vivo system to confirm that they bind to and mediate the degradation of the mRNA encoding the fungal specific MPR1. To design an antisense oligonucleotide that specifically binds to and mediates the degradation of a fungal-specific MPR1 encoding nucleic acid, it is preferred that the sequence recognized by the oligonucleotide is unique or substantially unique to the fungal specific MPR1 to be inhibited. For example, sequences that are frequently repeated across an encoding sequence may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for a fungal specific MPR1.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense sufficient to suppress translation on endogenous mRNAs in certain instances. Therefore another approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al, 1982, Nature 296:39-42), etc. Any type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

2. Small Interfering RNA (siRNA or RNAi)

In some embodiments, the inhibitory nucleic acid is a small interfering RNA (siRNA or RNAi) molecule. RNAi constructs comprise double stranded RNA that can specifically block expression of a target gene. "RNA interference" or "RNAi" is a term initially applied to a phenomenon where double-stranded RNA (dsRNA) blocks gene expression in a specific and post-transcriptional manner. RNAi provides a useful method of inhibiting gene expression in vitro or in vivo. RNAi constructs can include small interfering RNAs (siRNAs), hairpin RNAs, and other RNA species which can be cleaved in vivo to form siRNAs. RNAi constructs herein also include expression vectors ("RNAi expression vectors") capable of giving rise to transcripts which form dsRNAs or hairpin RNAs in cells, and/or transcripts which can produce siRNAs in vivo.

RNAi expression vectors express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences. The choice of promoter and other regulatory elements generally varies according to the intended host cell.

The RNAi constructs contain a nucleotide sequence that hybridizes under physiologic conditions of the cell to the nucleotide sequence of at least a portion of the mRNA transcript for the gene to be inhibited (i.e., a fungal-specific MPR1-encoding nucleic acid sequence). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity can be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, for example, 95%, 96%, 97%, 98%, 99%, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of an nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997)

Antisense Nucleic Acid Drug Dev 7:55-61). Merely to illustrate, the backbone of an RNAi construct can be modified with phosphorothioates, phosphoramidate, phosphodithioates, chimeric methylphosphonate-phosphodie-sters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) Proc Natl Acad Sci USA, 98:9742-9747; Elbashir, et al. (2001) EMBO J, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain preferred embodiments, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In other embodiments, the RNAi construct is in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon are preferred.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO 01/77350 describes an exemplary vector for bi-directional transcription of a transgene to yield both sense and antisense RNA transcripts of the same transgene in a eukaryotic cell. Accordingly, in certain embodiments, the present invention provides a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in WO 01/68836 and WO 01/75164.

Exemplary RNAi constructs that specifically recognize a particular gene, or a particular family of genes can be selected using methodology outlined in detail above with respect to the selection of antisense oligonucleotide. Similarly, methods of delivery RNAi constructs include the methods for delivery antisense oligonucleotides outlined in detail above.

3. Ribozymes

In some embodiments, the inhibitory nucleic acid is a ribozyme. Ribozymes molecules designed to catalytically cleave an mRNA transcripts can also be used to prevent translation of mRNA (See, e.g., PCT International Publication WO 90/11364; Sarver et al., 1990, Science 247:1222-1225 and U.S. Pat. No. 5,093,246). While ribozymes that cleave mRNA at site-specific recognition sequences can be used to destroy particular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585-591.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al., 1984, Science, 224:574-578; Zaug and Cech, 1986, Science, 231:470-475; Zaug, et al., 1986, Nature, 324:429-433; WO 88/04300; Been and Cech, 1986, Cell, 47:207-216). The Cech-type ribozymes have an eight base pair active site that hybridizes to a target RNA sequence whereafter cleavage of the target RNA takes place. The invention encompasses those Cech-type ribozymes that target eight base-pair active site sequences.

As in the antisense approach, the ribozymes can be composed of modified oligonucleotides (e.g., for improved stability, targeting, etc.) and can be delivered to cells in vitro or in vivo. A preferred method of delivery involves using a DNA construct "encoding" the ribozyme under the control of a strong constitutive pol III or pol II promoter, so that transfected cells will produce sufficient quantities of the ribozyme to destroy targeted messages and inhibit translation. Because ribozymes unlike antisense molecules, are catalytic, a lower intracellular concentration is required for efficiency.

DNA enzymes incorporate some of the mechanistic features of both antisense and ribozyme technologies. DNA enzymes are designed so that they recognize a particular target nucleic acid sequence, much like an antisense oligonucleotide, however much like a ribozyme they are catalytic and specifically cleave the target nucleic acid.

There are currently two basic types of DNA enzymes, and both of these were identified by Santoro and Joyce (see, for example, U.S. Pat. No. 6,110,462). The 10-23 DNA enzyme comprises a loop structure which connect two arms. The two arms provide specificity by recognizing the particular target nucleic acid sequence while the loop structure provides catalytic function under physiological conditions.

Briefly, to design an ideal DNA enzyme that specifically recognizes and cleaves a target nucleic acid, one of skill in the art must first identify the unique target sequence. This can be done using the same approach as outlined for antisense oligonucleotides. Preferably, the unique or substantially sequence is a G/C rich of approximately 18 to 22 nucleotides. High G/C content helps insure a stronger interaction between the DNA enzyme and the target sequence.

When synthesizing the DNA enzyme, the specific antisense recognition sequence that will target the enzyme to the message is divided so that it comprises the two arms of the DNA enzyme, and the DNA enzyme loop is placed between the two specific arms.

Methods of making and administering DNA enzymes can be found, for example, in U.S. Pat. No. 6,110,462. Similarly, methods of delivery DNA ribozymes in vitro or in vivo include methods of delivery RNA ribozyme, as outlined in detail above. Additionally, one of skill in the art will recognize that, like antisense oligonucleotide, DNA enzymes can be optionally modified to improve stability and improve resistance to degradation.

c. Screening for Inhibitors of MPR1

One can identify lead compounds that are suitable for further testing to identify those that are therapeutically effective inhibitory agents by screening a variety of compounds and mixtures of compounds for their ability to decrease or inhibit fungal-specific MPR1 metalloprotease activity and/or prevent or inhibit *Cryptococcus* infection of the CNS and/or brain tissue in vivo and/or prevent, reduce or inhibit the ability of *Cryptococcus* to cross the blood-brain-barrier in in vivo and in vitro assays, as described herein.

The use of screening assays to discover naturally occurring compounds with desired activities is well known and has been widely used for many years. For instance, many compounds with antibiotic activity were originally identified using this approach. Examples of such compounds include monolactams and aminoglycoside antibiotics. Compounds which inhibit various enzyme activities have also been found by this technique, for example, mevinolin, lovastatin, and mevacor, which are inhibitors of hydroxymethylglutamyl Coenzyme A reductase, an enzyme involved in cholesterol synthesis. Antibiotics that inhibit glycosyltransferase activities, such as tunicamycin and streptovirudin have also been identified in this manner.

Thus, another important aspect of the present invention is directed to methods for screening samples for inhibition or reduction of fungal-specific MPR1 activity. A "sample" as used herein can be any mixture of compounds suitable for testing in a MPR1 metalloprotease assay. A typical sample comprises a mixture of synthetically produced compounds or alternatively a naturally occurring mixture, such as a cell culture broth. Suitable cells include any cultured cells such as mammalian, insect, microbial or plant cells. Microbial cell cultures are composed of any microscopic organism such as bacteria, protozoa, yeast, fungi and the like.

In the typical screening assay, a sample, for example a fungal broth, is added to a standard fungal-specific MPR1 assay. If inhibition or enhancement of activity as compared to control assays is found, the mixture is usually fractionated to identify components of the sample providing the inhibiting or enhancing activity. The sample is fractionated using standard methods such as ion exchange chromatography, affinity chromatography, electrophoresis, ultrafiltration, HPLC and the like. See, e.g., Scopes, Protein Purification, Principles and Practice, 3rd Edition, 1994, Springer-Verlag. Each isolated fraction is then tested for inhibiting or enhancing activity. If desired, the fractions are then further subfractionated and tested. This subfractionation and testing procedure can be repeated as many times as desired.

By combining various standard purification methods, a substantially pure compound suitable for in vivo therapeutic testing can be obtained. A substantially pure modulating agent as defined herein is an activity inhibiting or enhancing compound which migrates largely as a single band under standard electrophoretic conditions or largely as a single peak when monitored on a chromatographic column. More specifically, compositions of substantially pure modulating agents will comprise less than ten percent miscellaneous compounds.

In preferred embodiments, the assays are designed to screen large chemical libraries by automating the assay steps and providing compounds from any convenient source to assays, which are typically run in parallel (e.g., in microtiter formats on microtiter plates in robotic assays).

As noted, the invention provides in vitro assays for fungal-specific MPR1 metalloprotease activity in a high throughput format. For each of the assay formats described, "no inhibitor" control reactions which do not include an inhibitory agent provide a background level of MPR1 metalloprotease activity. In the high throughput assays of the invention, it is possible to screen up to several thousand different modulators in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many different plates per day; assay screens for up to about 6,000-20,000, and even up to about 100,000-1,000,000 different compounds is possible using the integrated systems of the invention. The steps of labeling, addition of reagents, fluid changes, and detection are compatible with full automation, for instance using programmable robotic systems or "integrated systems" commercially available, for example, through BioTX Automation, Conroe, Tex.; Qiagen, Valencia, Calif.; Beckman Coulter, Fullerton, Calif.; and Caliper Life Sciences, Hopkinton, Mass.

In some assays it will be desirable to have positive controls to ensure that the components of the assays are working properly. For example, a known inhibitor of MPR1 metalloprotease activity can be incubated with one sample of the assay, and the resulting increase or decrease in signal determined according to the methods herein.

Essentially any chemical compound can be screened as a potential inhibitor of fungal-specific MPR1 metalloprotease activity in the assays of the invention. Most preferred are generally compounds that can be dissolved in aqueous or organic (especially DMSO-based) solutions and compounds which fall within Lipinski's "Rule of 5" criteria. The assays are designed to screen large chemical libraries by automating the assay steps and providing compounds from any convenient source to assays, which are typically run in parallel (e.g., in microtiter formats on multiwell plates in robotic assays). It will be appreciated that there are many suppliers of chemical compounds, including Sigma-Aldrich (St. Louis, Mo.); Fluka Chemika-Biochemica Analytika (Buchs Switzerland), as well as numerous providers of small organic molecule libraries ready for screening, including Chembridge Corp. (San Diego, Calif.), Discovery Partners International (San Diego, Calif.), Triad Therapeutics (San Diego, Calif.), Nanosyn (Menlo Park, Calif.), Affymax (Palo Alto, Calif.), ComGenex (South San Francisco, Calif.), Tripos, Inc. (St. Louis, Mo.), Reaction Biology Corp. (Malvern, Pa.), Biomol Intl. (Plymouth Meeting, Pa.), TimTec (Newark, Del.), and AnalytiCon (Potsdam, Germany), among others.

In one preferred embodiment, inhibitors of fungal-specific MPR1 metalloprotease activity are identified by screening a combinatorial library containing a large number of potential therapeutic compounds (potential inhibitor compounds). Such "combinatorial chemical or peptide libraries" can be screened in one or more assays, as described herein, to identify those library members particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with .beta.-D-glucose scaffolding (Hirschmann et al., J. Amer. Chem. Soc. 114: 9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see, Ausubel and Sambrook, all supra), peptide nucleic acid libraries (see, e.g., U.S. Pat. No. 5,539,083), antibody libraries (see, e.g., Vaughn et al., Nature Biotechnology, 14(3): 309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.).

Lead compounds that have been identified for their capability to reduce or inhibit the metalloprotease activity of a fungal-specific MPR1 in vitro are then evaluated for their ability to prevent, reduce or inhibit the ability of *Cryptococcus* to cross the blood-brain-barrier in in vivo and in vitro assays, as described herein, and/or to prevent or inhibit *Cryptococcus* infection of the CNS and/or brain tissue in vivo. The ability of a particular compound to prevent, reduce or inhibit manifestations of disease in an animal model can be measured using any known technique. For example, test and control samples in in vitro assays and test and control animals in in vivo assays can be comparatively tested for disease signs, i.e., *Cryptococcus* infection and penetration of the blood-brain-barrier.

d. Formulation and Administration

In therapeutic applications, the MPR1 inhibitors can be administered to an individual already suffering from or at risk for contracting a *Cryptococcus* infection. Compositions that contain MPR1 inhibitors are administered to a patient in an amount sufficient to suppress the undesirable infection and to eliminate or at least partially arrest symptoms and/or complications. An amount adequate to accomplish this is defined as a "therapeutically effective dose." Amounts effective for this use will depend on, e.g., the inhibitor composition, the manner of administration, the stage and severity of the disease being treated, the weight and general state of health of the patient, and the judgment of the prescribing physician. Inhibitors of MPR1 activity can be administered chronically or acutely to treat or prevent a *Cryptococcus* infection. In certain instances, it will be appropriate to administer an inhibitor of MPR1 activity prophylactically, for instance in subjects at risk of or suspected of being infected with *Cryptococcus*.

Alternatively, DNA or RNA that inhibits expression of one or more sequences encoding a MPR1 metalloprotease, such as an antisense nucleic acid, a small-interfering nucleic acid (i.e., siRNA), a micro RNA (miRNA), or a nucleic acid that encodes a peptide that blocks expression or activity of a MPR1 can be introduced into patients to achieve inhibition. U.S. Pat. No. 5,580,859 describes the use of injection of naked nucleic acids into cells to obtain expression of the genes which the nucleic acids encode.

Therapeutically effective amounts of MPR1 inhibitor or enhancer compositions of the present invention generally range for the initial administration (that is for therapeutic or prophylactic administration) from about 0.1 g to about 10 mg of MPR1 inhibitor for a 70 kg patient, usually from about 1.0 g to about 1 mg, for example, between about 10 g to about 0.1 mg (100 µg). Typically, lower doses are initially administered and incrementally increased until a desired efficacious dose is reached. These doses can be followed by repeated administrations over weeks to months depending upon the patient's response and condition by evaluating symptoms associated with *Cryptococcus* infection (e.g., a cough that lasts weeks or months, sharp chest pains, unexplained shortness of breath, severe headache, confusion, fever, night sweats, and/or unintended weight loss).

For prophylactic use, administration should be given to subjects at risk for or suspected of having a *Cryptococcus* infection. Therapeutic administration may begin at the first sign of disease or the detection or shortly after diagnosis of infection. This is often followed by repeated administration until at least symptoms are substantially abated and for a period thereafter.

The MPR1 inhibitors for therapeutic or prophylactic treatment are intended for parenteral, topical, oral, intrathecal, intracranial, or local administration. Preferably, the compositions are formulated for oral administration. In certain embodiments, the pharmaceutical compositions are administered parenterally, e.g., intravenously, intranasally, inhalationally, subcutaneously, intradermally, or intramuscularly. In some embodiments, the MPR1 inhibitors are administered directly to the brain or CNS, e.g., intrathecally or intracranially. Compositions of the invention are also suitable for oral administration. Thus, the invention provides compositions for parenteral administration which comprise a solution of the MPR1 inhibiting agent dissolved or suspended in an acceptable carrier, preferably an aqueous carrier. A variety of aqueous carriers may be used, e.g., water, buffered water, 0.9% saline, 0.3% glycine or another suitable amino acid, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of MPR1 inhibiting agents of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The MPR1 inhibitors of the invention may also be administered via liposomes, which can be designed to target the conjugates to a particular tissue, for example lung, heart or CNS tissues, including brain tissue, as well as increase the half-life of the peptide composition. Liposomes include emulsions, foams, micelles, insoluble monolayers, liquid crystals, phospholipid dispersions, lamellar layers and the like. In these preparations, the peptide, nucleic acid or organic compound to be delivered is incorporated as part of a liposome, alone or in conjunction with a molecule which binds to, e.g., a receptor prevalent among the desired cells, or with other therapeutic compositions. Thus, liposomes filled with a desired peptide, nucleic acid, small molecule or conjugate of the invention can be directed to the site of, for example, immune cells, leukocytes, lymphocytes, myeloid cells or endothelial cells, where the liposomes then deliver the selected MPR1 inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid liability and stability of the liposomes in the blood stream. A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028.

The targeting of liposomes using a variety of targeting agents is well known in the art (see, e.g., U.S. Pat. Nos. 4,957,773 and 4,603,044). For targeting to desired cells, a ligand to be incorporated into the liposome can include, e.g., antibodies or fragments thereof specific for cell surface determinants of the target cells. A liposome suspension containing a MPR1 inhibitor may be administered intravenously, locally, topically, etc. in a dose which varies according to, inter alia, the manner of administration, the conjugate being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more conjugates of the invention, and more preferably at a concentration of 25%-75%.

For aerosol administration, the inhibitors are preferably supplied in a suitable form along with a surfactant and propellant. Typical percentages of MPR1 inhibitors are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included, as desired, as with, e.g., lecithin for intranasal delivery.

An effective anti-infective treatment is indicated by a decrease in observed symptoms (e.g., a cough that lasts weeks or months, sharp chest pains, unexplained shortness of breath, severe headache, confusion, fever, night sweats, and/or unintended weight loss), and/or *Cryptococcus* burden, as measured according to a clinician or reported by the patient. Alternatively, methods for detecting levels of specific MPR1 activities can be used. Standard assays for detecting MPR1 activity are described herein. Again, an effective anti-infective treatment is indicated by a substantial reduction in activity of MPR1. As used herein, a "substantial reduction" in MPR1 activity refers to a reduction of at least about 30% in the test sample compared to an untreated control. Preferably, the reduction is at least about 50%, more preferably at least about 75%, and most preferably MPR1 activity levels are reduced by at least about 90% in a sample from a treated mammal compared to an untreated control. In some embodiments, the MPR1 activity is completely inhibited.

3. Methods of Delivering Therapeutic into the Central Nervous System

The MPR1 enzyme, and fragments thereof, as described herein, also finds use to facilitate, increase and/or enhance delivery of therapeutic agents across the blood-brain-barrier and into the CNS tissues.

a. Subjects Who May Benefit

Subjects who are currently receiving therapeutic agents intended to be delivered across the blood-brain-barrier, e.g., to the central nervous system (CNS) and/or brain tissues can benefit from methods of using the MPR1 enzyme, and fragments thereof, to facilitate and/or enhance delivery of the therapeutic agent. Subjects may have or be diagnosed as having a disease that affects the CNS, for example, a neurodegenerative disease. Illustrative neurodegenerative diseases include without limitation, multiple sclerosis, Alzheimer's disease, Parkinson's disease, and Huntington's disease. In some embodiments, the subject may have or be diagnosed as having a cancer of a CNS tissue. Illustrative nervous and sensory system cancers that can be treated or prevented by delivering therapeutic agents across the blood-brain-barrier include without limitation neuroblastoma, brain tumors, meningioma, ependymoma, medulloblastoma, peripheral neuroectodermal tumors, glioblastoma, astrocytoma, oligodendroglioma and retinoblastoma. In various embodiments, the subject may have or be diagnosed as having an infection and/or inflammation within the brain and/or CNS. Illustrative infections and/or inflammations within the CNS include without limitation meningitis and encephalitis. In various embodiments, the subject may have or be diagnosed as having epilepsy or migraines.

b. MPR1 and Enzymatically Active Fragments Thereof

For methods of increasing, promoting and/or enhancing delivery of a therapeutic agent across the blood-brain-barrier, a therapeutic agent is systemically administered in conjunction with a M36 fungalysin metalloprotease (e.g., MPR1) having at least 80% sequence identity, e.g., at least about 85%, 90%, 91%, 92%, 93%, 94%, 95%, 96%, 97%, 98% or 99% sequence identity, to an amino acid sequence of SEQ ID NO: 1, or a fragment thereof, that retains protease activity. In some embodiments, the M36 fungalysin metalloprotease has an amino acid sequence of SEQ ID NOs: 1, 3, 5 or 7.

In some embodiments, the M36 fungalysin metalloprotease is the full length enzyme. In some embodiments, the M36 fungalysin metalloprotease is a fragment comprising the peptidase_M36 domain (e.g., comprises a fragment corresponding to residues 446-722 of SEQ ID NOs: 1, 3 and/or 5 and/or corresponding to residues 446-706 of SEQ ID NO:7). In some embodiments, the M36 fungalysin metalloprotease is a fragment comprising and no longer than the peptidase_M36 domain. In some embodiments, the M36 fungalysin metalloprotease is a fragment comprising and no longer than the M36 GluZincin superfamily domain. In some embodiments, the M36 fungalysin metalloprotease is a fragment, and the propeptide FTP domain is removed (e.g., wherein amino acid residues corresponding to positions 95-141 of SEQ ID NOs: 1, 3, 5 and/or 7 are removed). In some embodiments, the M36 fungalysin metalloprotease is a fragment, and the N-terminal signal peptide and propeptide FTP domain are removed (e.g., wherein amino acid residues corresponding to positions 1-20 and 95-141 of SEQ ID NOs: 1, 3, 5 and/or 7 are removed). In some embodiments, the M36 fungalysin metalloprotease is a fragment, and the N-terminal amino acid residues 1-300 are removed. In some embodiments, the M36 fungalysin metalloprotease is a fragment, and the N-terminal amino acid residues 1-375 are removed.

c. Therapeutic Agents

As appropriate, the therapeutic agent can be a cell, a small organic molecule, small inorganic molecule, a peptide, a polypeptide or a nucleic acid. In some embodiments, the therapeutic agent is effective in the treatment, mitigation or prevention of a cancer of the central nervous system or a neurodegenerative disease. Generally, the M36 fungalysin metalloprotease (e.g., MPR1), or an enzymatically active fragment thereof is administered in conjunction with a therapeutic agent already known in the art as useful for treating, mitigating or preventing the disease affecting the CNS, e.g., known to be useful for treating, mitigating or preventing a neurodegenerative disease (e.g., multiple sclerosis, Alzheimer's disease, Parkinson's disease, and Huntington's disease) or a cancer of the central nervous system (e.g., neuroblastoma, brain tumors, meningioma, ependymoma, medulloblastoma, peripheral neuroectodermal tumors, glioblastoma, astrocytoma, oligodendroglioma and retinoblastoma).

Therapeutic agents useful for the treatment, mitigation and/or prevention of Alzheimer's disease include without limitation cholinesterase inhibitors (e.g., e.g., tacrine, ipidacrine, galantamine, donepezil, icopezil, zanapezil, rivastigmine, huperzine A, phenserine, physostigmine, neostigmine, pyridostigmine, ambenonium, demarcarium, edrophonium, ladostigil, ungeremine, and the like), glutamate pathway modifiers (e.g., memantine), tropisetron, disulfiram, honokiol and nimetazepam. Further therapeutic agents useful for the treatment, mitigation and/or prevention of Alzheimer's disease are reviewed, e.g., in Mangialasche, et al., *Lancet Neurol* (2010) 9: 702-16. Alzheimer's may also be treated or prevented by administration of antibodies, or fragments thereof, that bind to Abeta. Therapeutic agents useful for the treatment, mitigation and/or prevention of Parkinson's disease include without limitation dopamine agonists (e.g., levodopa, Carbidopa/Levodopa (Sinemet®); pramipexole (Mirapex), ropinirole (Requip), and apomorphine (Apokyn)); monoamine oxidase B (MAO B) inhibitors (e.g., selegiline (Eldepryl) and rasagiline (Azilect)); Catechol O-methyltransferase (COMT) inhibitors (e.g., Tolcapone (Tasmar) and Entacapone (Comtan)); Anticholinergics (e.g., benztropine (Cogentin), trihexyphenidyl and Rivastigmine); Glutamate (NMDA) blocking drugs (e.g., amantadine (Symmetrel); and anti-synuclein antibodies, or fragments thereof). Illustrative therapeutic agents useful to mitigate the symptoms of Huntington's disease, include without limitation Tetrabenazine (Xenazine); Antipsychotic drugs (e.g., haloperidol (Haldol) and clozapine (Clozaril)); antiseizure drugs (e.g., clonazepam (Klonopin); and anti-anxiety drugs (e.g., diazepam (Valium)). Illustrative therapeutic agents useful for the treatment, mitigation and/or prevention of multiple sclerosis include without limitation, e.g., Beta interferons (e.g., Avonex, Betaseron, Extavia and Rebif); Glatiramer (Copaxone); Fingolimod (Gilenya); Natalizumab (Tysabri); and Mitoxantrone (Novantrone).

In various embodiments, the therapeutic agent is a chemotherapeutic agent useful to treat, mitigate or prevent a cancer of the central nervous system or cancer that has metastasized into the CNS and/or brain tissues. Examples of chemotherapeutic agents that can be administered in conjunction with a M36 fungalysin metalloprotease (e.g., MPR1), or an enzymatically active fragment thereof, include without limitation alkylating agent(s) (e.g., nitrogen mustards, nitrogen ureas, ethylenimines, methylmelamines, alkyl sulfonates, carmustine, triazenes), platinum-coordination complexes (e.g., cisplatin, carboplatin, and oxaliplatin), anti-metabolite(s) (e.g., folic acid analogs (e.g., methotrexate), pyrimidine analogs (e.g., capecitabine, 5-fluorouracil, 5 fluorodeoxyuridine, 5-fluorodeoxyuridine monophosphate, cytosine arabinoside, 5 azacytidine, gemcitabine), purine analogs (e.g., mercaptopurine, thioguanine, azathioprine, pentostatin, erythrohydroxynonyladenine, fludarabine, cladribine)), plant alkaloid(s) and/or terpenoid(s), vinca alkaloid(s) (e.g., vincristine, vinblastine, vinorelbine, and vindesine), podophyllotoxin(s) (e.g., etoposide and teniposide), camptothecin(s) (e.g., irinotecan and topotecan), anthracycline(s), aromatase inhibitor(s), taxane(s) (e.g., paclitaxel, taxol and docetaxel), topoisomerase inhibitor(s) (e.g., (Type I inhibitors: camptothecins, including irinotecan and topotecan; Type II Inhibitors: amsacrine, etoposide, etoposide phosphate, and teniposide), antibiotic(s) (e.g., dactinomycin, daunorubicin, doxorubincin, idarubicin, epirubicin, bleomycins, mitomycin), hormone(s), differentiating agent(s), kinase inhibitor(s) (e.g., Bevacizumab, BIBW 2992, Cetuximab, Imatinib, Trastuzumab, Gefitinib, Ranibizumab, Pegaptanib, Sorafenib, Dasatinib, Sunitinib, Erlotinib, Nilotinib, Lapatinib, Panitumumab, Vandetanib, E7080, Pazopanib, Mubritinib and Fostamatinib) and anti-neoplastic agent(s) (e.g., (dactinomycin, doxorubicin, epirubicin, fludarabine and bleomycin). In some embodiments, the therapeutic agent is an antibody directed against a cancer-associated antigen.

Examples of therapeutic antibodies that can be administered in conjunction with a M36 fungalysin metalloprotease (e.g., MPR1), or an enzymatically active fragment thereof, include but are not limited to HERCEPTIN™ (Trastuzumab) (Genentech, CA) which is a humanized anti-HER2 monoclonal antibody; REOPRO™ (abciximab) (Centocor) which is an anti-glycoprotein IIb/IIIa receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope); IgG antibody (ImClone System); IMC-C225 which is a chimeric anti-EGFR IgG antibody; VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); ICM3 which is a humanized anti-ICAM3 antibody (ICOS Pharm); IDEC-114 which is a primate anti-CD80 antibody (IDEC Pharm/Mitsubishi); ZEVALIN™ which is a radiolabelled murine anti-CD20 antibody (IDEC/Schering AG); IDEC-131 which is a humanized anti-CD40L antibody (IDEC/Eisai); IDEC-151 which is a primatized anti-CD4 antibody (IDEC); IDEC-152 which is a primatized anti-CD23 antibody (IDEC/Seikagaku); SMART anti-CD3 which is a humanized anti-CD3 IgG (Protein Design Lab); 5G1.1 which is a humanized anti-complement factor 5 (C5) antibody (Alexion Pharm); D2E7 which is a humanized anti-TNF-α antibody (CATIBASF); CDP870 which is a humanized anti-TNF-α Fab fragment (Celltech); IDEC-151 which is a primatized anti-CD4 IgG1 antibody (IDEC Pharm/SmithKline Beecham); MDX-CD4 which is a human anti-CD4 IgG antibody (Medarex/Eisai/Genmab); CDP571 which is a humanized anti-TNF-α IgG4 antibody (Celltech); LDP-02 which is a humanized anti-α4,7 antibody (LeukoSite/Genentech); OrthoClone OKT4A which is a humanized anti-CD4 IgG antibody (Ortho Biotech); ANTOVA™ which is a humanized anti-CD40L IgG antibody (Biogen); ANTEGREN™ which is a humanized anti-VLA-4 IgG antibody (Elan); and CAT-152 which is a human anti-TGF-β2 antibody (Cambridge Ab Tech).

Therapeutic agents useful for the treatment, mitigation and/or prevention of meningitis or encephalitis depend in the etiology of the meningitis or encephalitis and can include antiviral agents (e.g., agents that inhibit or reduce the replication of Herpes virus, e.g., Acyclovir (Zovirax), Ganciclovir (Cytovene)), antibiotics, antifungal agents, anticancer or antineoplastic agents and/or anti-inflammatory agents (e.g., a non-steroidal anti-inflammatory agent (NSAID), e.g., aspirin, acetaminophen, diclofenac potassium, diclofenac sodium, diclofenac sodium with misoprostol, diflunisal, etodolac, fenoprofen calcium, flurbiprofen, ibuprofen, indomethacin, ketoprofen, meclofenamate sodium, mefenamic acid, meloxicam, nabumetone, naproxen sodium, piroxicam, tolmetin sodium, magnesium salicylate, choline salicylate, salsalate, sodium salicylate, alkyl salicylate or disalicylate, or a selective inhibitor of COX-2 (e.g., celecoxib, valdecoxib, lumiracoxib, etoricoxib, or rofecoxib).

d. Host Cells

In various embodiments, the M36 fungalysin metalloprotease (e.g., MPR1), or an enzymatically active fragment thereof, is expressed in or attached to a heterologous host cell (e.g., a cell other than a *Cryptococcus* host cell) to facilitate the delivery of the host cell across the blood-brain-barrier and into the CNS and/or brain of a subject. In various embodiments, the host cell is a mammalian cell. In some embodiments, the host cell is a stem cell, for example, a neuronal stem cell or a mesenchymal stem cell. The host cell is transformed with a nucleic acid encoding the M36 fungalysin metalloprotease (e.g., MPR1), or an enzymatically active fragment thereof.

A variety of methods are known in the art for expressing a gene in eukaryotes (Ausubel, et al. Editor, *Current Protocols in Molecular Biology, USA,* 1984-2012). These methods often achieve expression of a gene above basal.

Transfection of Cells with an Expression Cassette.

Cells can be transfected with an expression cassette containing the gene of interest and a promoter. The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function. The promoter typically can also include elements that are responsive to transactivation, e.g., hypoxia responsive elements, Gal4 responsive elements, lac repressor responsive elements, and the like. The promoter can be constitutive or inducible, heterologous or homologous.

In addition to the promoter, the expression vector typically contains a transcription unit or expression cassette that contains all the additional elements required for the expression of the nucleic acid in host cells. A typical expression cassette thus contains a promoter operably linked, e.g., to the nucleic acid sequence encoding a M36 fungalysin metalloprotease (e.g., MPR1), or fragment thereof, and signals required for efficient polyadenylation of the transcript, ribosome binding sites, and translation termination. The nucleic acid sequence may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens.* Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a M36 fungalysin metalloprotease (e.g., MPR1) encoding sequence under the direction of the polyhedrin promoter or other strong baculovirus promoters.

The elements that are typically included in expression vectors also include a replicon that functions in *E. coli,* a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect host cell lines that express large quantities of protein, which are then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds, 1983). In some embodiments, a viral vector comprising a polynucleotide encoding a M36 fungalysin metalloprotease (e.g., MPR1), or fragment thereof, is used to transfect the host cell.

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well-known methods for introducing cloned genomic DNA, cDNA, synthetic DNA or other foreign genetic material into a host cell (see, e.g., Green and Sambrook, Molecular Cloning: A Laboratory Manual (Fourth Edition), Cold Spring Harbor Laboratory Press, 2012). It is only necessary that the particular genetic engineering procedure used be capable of successfully introducing at least one gene into the host cell capable of expressing the protein of choice. Techniques for transfecting stem cells are described, e.g., by Lakshmipathy, et al., *Stem Cells.* (2004) 22(4):531-43; Moore, et al., *Stem Cell Research & Therapy* (2010) 1:23 and find use. Reagents for transfection of stem cells and other cells are commercially available, e.g., from Life Technologies (lifetechnologies.com or invitrogen.com), Global-Stem (globalstem.com), AmsBio (amsbio.com), Miltenyi Biotec (miltenyibiotec.com), Dharmacon (dharmacon.com), Roche Applied Sciences (roche-applied-science.com), and MaxCyte (maxcyte.com).

After the expression vector is introduced into the cells, the transfected cells are cultured under conditions favoring expression of the M36 fungalysin metalloprotease (e.g., MPR1) protein, which is recovered from the culture using standard techniques identified below.

e. Formulation and Administration
i. Formulation

Compositions comprising the M36 fungalysin metalloprotease (e.g., MPR1), or an enzymatically active fragment thereof, in conjunction with a therapeutic agent are particularly useful for parenteral administration, e.g., intravenous or intrapulmonary administration or administration into a body cavity or lumen of an organ. The compositions for administration will commonly comprise a solution of the polypeptide comprising the polypeptide dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of polypeptide in these formulations can vary widely, and will be selected primarily based on fluid volumes, viscosities, body weight and the like in accordance with the particular mode of administration selected and the patient's needs.

Liquid form pharmaceutical preparations can include solutions, suspensions, and emulsions, for example, water or water/propylene glycol solutions. Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents. For parenteral injection, liquid preparations can be formulated in solution in aqueous polyethylene glycol solution. Transdermal administration can be performed using suitable carriers. If desired, apparatuses designed to facilitate transdermal delivery can be employed. Suitable carriers and apparatuses are well known in the art, as exemplified by U.S. Pat. Nos. 6,635,274, 6,623,457, 6,562,004, and 6,274,166.

In various embodiments, the therapeutic agent is encapsulated in a liposome. Liposomes include emulsions, foams, micelles, insoluble monolayers, liquid crystals, phospholipid dispersions, lamellar layers and the like. In these preparations the composition of the invention to be delivered is incorporated as part of a liposome, alone or in conjunction with a molecule which binds to a desired target, such as antibody, or with other therapeutic or immunogenic compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., Ann. Rev. Biophys. Bioeng. 9:467 (1980), U.S. Pat. Nos. 4,235,871; 4,501,728; 4,837,028 and 5,019,369. M36 fungalysin metalloprotease (e.g., MPR1), and enzymatically active fragments thereof, can be integrated into, attached or conjugated directly to the liposome using methods known in the art. Anti-CD22 antibodies conjugated to liposome-encapsulated doxorubicin has been tested in in vivo animal models. See, e.g., O'Donnell, et al., Invest New Drugs. (2010) 28(3):260-7; O'Donnell, et al., Cancer Immunol Immunother. (2009) 58(12):2051-8 and Tuscano, et al., Clin Cancer Res. (2010) 16(10):2760-8. Those of skill in the art will readily appreciate that the anti-CD22 targeting moiety can be replaced with a M36 fungalysin metalloprotease (e.g., MPR1), and enzymatically active fragments thereof, and the doxorubicin can be exchanged with another therapeutic agent(s) of interest.

In some embodiments, the M36 fungalysin metalloprotease (e.g., MPR1), and enzymatically active fragments thereof, are attached or conjugated to a liposome or a nanoparticle that encapsulates the therapeutic agent. Nanoparticles for encapsulation and delivery of a therapeutic agent are known in the art and can find use. Illustrative nanoparticles include without limitation, e.g., semiconductor quantum dots (QDs), silicon (Si) nanoparticles (Park, et al., *Nature Materials* (2009) 8:331-336; Tu, et al., *JACS*, (2010) 132:2016-2023; Zhang, et al., JACS, (2007) 129: 10668; Singh M P et al., ACS Nano, (2012) In press, (DOI: 10.1021/nn301536n); Rosso-Vasic, et al., *J. Mater. Chem.* (2009) 19:5926-5933; Bhattacharjee S., et al., Nanotoxicology, (2011) DOI 10.3109/17435390.2011.633714, 1-14; Chandra, et al., Nanoscale (2011) 3:1533-1540), polylactide-co-glycolide nanoparticles for controlled delivery of anticancer agents (Dinarvand, et al., *Int J Nanomedicine.* 2011; 6:877-95); polyethyleneimine (PEI)-As(2)O(3)/Mn (0.5)Zn(0.5)Fe(2)O(4) magnetic nanoliposomes (Wang, et al., *Int J Nanomedicine.* 2011; 6:871-5); redox-responsive poly(ethylene glycol)-b-poly(lactic acid) (MPEG-SS-PLA) nanoparticles (Song, et al., *Colloids SurfB Biointerfaces.* 2011, PMID 21719259); Thiolated Pluronic (Plu-SH) nanoparticles (Abdullah-Al-Nahain, et al., *Macromol Biosci.* 2011, PMID 21717576); and mesoporous silica nanoparticles (MSNs) (Wu, et al., *Chem Commun* (Camb). 2011, PMID 21716992). In one embodiment, the M36 fungalysin metalloprotease (e.g., MPR1), and enzymatically active fragments thereof are conjugated to biocompatible nanomicelles comprised of cholic acid, lysine and polyethylene glycol (PEG) covalently conjugated together, e.g., described in Xiao, et al., *Biomaterials* (2009) 30:6006-6016; and Luo, et al., *Bioconjug Chem* (2010) 21:1216-1224. Further nanomicelles that find use are described, e.g., in PCT Patent Publ. WO 2010/039496.

In one embodiment, the M36 fungalysin metalloprotease (e.g., MPR1), and enzymatically active fragments thereof, are attached or conjugated to biocompatible nanomicelles comprised of cholic acid, lysine and polyethylene glycol (PEG) covalently conjugated together, e.g., as described in Xiao, et al., *Biomaterials* (2009) 30:6006-6016; and Luo, et al., *Bioconjug Chem* (2010) 21:1216-1224. Recently, a biocompatible nanomicelle drug delivery system comprised of a unique amphiphilic polymers called telodendrimers was developed [Xiao, et al., *Biomaterials* (2009) 30:6006-6016; Luo, et al., *Bioconjug Chem* (2010) 21:1216-1224]. Telodendrimers consist of cholic acid, lysine and polyethylene glycol (PEG) covalently conjugated together, which impart the ability to self-assemble into a water-soluble spheroid with a hydrophobic core capable of sequestering many types of drugs. Cholic acid, a primary component of bile acid, possesses a facial amphiphilic structure: a rigid steroid scaffold with four hydrophilic groups on one surface, and hydrophobic methyl groups on the other surface of the scaffold. Lysine is a natural amino acid. PEG is biocompatible and has been used to improve the pharmacokinetics of therapeutic drugs. This nanocarrier system has many attractive characteristics for drug delivery, such as high drug loading capacity, narrow polydispersity, well-defined structure, easy chemical modification, superior physical, chemical stability and biocompatibility.

In some embodiments, the M36 fungalysin metalloprotease (e.g., MPR1), or an enzymatically active fragment thereof, in conjunction with a therapeutic agent is formulated as a nanoparticle. Nanoparticle conjugates are known in the art and described, e.g., in Musacchio, et al., Front Biosci. (2011) 16:1388-412; Cuong, et al., Curr Cancer Drug Targets. (2011) 11(2):147-55; Jain, BMC Med. (2010) 8:83; Sunderland, et al., Drug Development Research (2006) 67(1):70-93; Gu, et al., Nanotoday (2007) 2(3):14-21; Alexis, et al., ChemMedChem. (2008) 3(12):1839-43; Fay, et al., Immunotherapy. (2011) 3(3):381-394; Minko, et al., Methods Mol Biol. (2010) 624:281-94; and PCT Publ. Nos. WO 2011/046842; WO 2010/040062; WO 2010/047765; and WO 2010/120385, the disclosures of which are hereby incorporated herein by reference in their entirety for all purposes. Known nanoparticle cores find use in encapsulating a therapeutic agent (e.g., a chemotherapeutic agent or an anti-neoplastic agent) for delivering to a lung cancer cell and/or to a prostate cancer cell. A M36 fungalysin metalloprotease (e.g., MPR1), or an enzymatically active fragment thereof, can be integrated into, attached or conjugated directly to the nanoparticle core using methods known in the art. In some embodiments, the encapsulating nanoparticle is a cylindrical PRINT nanoparticle, e.g., as described in Gratton, et al., Proc Natl Acad Sci USA. (2008) 105(33): 11613-8. The nanoparticle can be biodegradable or non-biodegradable, as appropriate or desired. Poly(lactic acid-co-glycolic acid) (PLGA), biodegradable poly(L lactic acid) (PLLA) and PEG-based hydrogels find use as a matrix material in particle drug delivery systems because they are biocompatible, bioabsorbable, and have already shown promise in medical applications.

Peptide nanoparticles and methods for their preparation are known in the art and described, e.g., in U.S. Patent Publication No. 2006/0251726, U.S. Patent Publication No. 2004/0126900, U.S. Patent Publication No. 2005/0112089, U.S. Patent Publication No. 2010/0172943, U.S. Patent Publication No. 2010/0055189, U.S. Patent Publication No. 2009/0306335, U.S. Patent Publication No. 2009/0156480, and U.S. Patent Publication No. 2008/0213377, each of which is hereby incorporated herein by reference in its entirety for all purposes. Further nanoparticle formulations that find use are described, e.g., in Emerich and Thanos, *Curr Opin Mol Ther* (2008) 10(2):132-9; Kogan, et al., *Nanomedicine* (2007) 2(3):287-306; Zhang, et al., *Bioconjug Chem* (2008) 19(1):145-152; Scarberry, et al., *J Am Chem Soc* (2008) 130(31): 10258-10262; Fraysse-Ailhas, et al., *Eur Cells Materials* (2007) 14(Suppl. 3): 115; Corrias F, Lai F., *Recent Pat Drug Deliv Formul.* 2011 Aug. 12, PMID:21834772; Wang, et al., *Biomaterials*. (2011) 32(32): 8281-90; and Kaur, et al., *Artif Cells Blood Substit Immobil Biotechnol.* 2011 Aug. 2., PMID:21806501.

Also contemplated are solid form pharmaceutical formulations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical formulation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention.

In one embodiment, a pharmaceutical formulation is administered to a patient at a therapeutically effective dose to prevent, treat, mitigate or control a disease or malignant condition, such as a cancer of the CNS and/or a neurodegenerative disease. The pharmaceutical composition or medicament is administered to a patient in an amount sufficient to elicit an effective therapeutic or diagnostic response in the patient. An effective therapeutic or diagnostic response is a response that at least partially arrests or slows the symptoms or complications of the disease or malignant condition. An amount adequate to accomplish this is defined as "therapeutically effective dose."

ii. Routes of Administration

The M36 fungalysin metalloprotease (e.g., MPR1), or an enzymatically active fragment thereof, in conjunction with a therapeutic agent can be formulated into pharmaceutical formulations for administration to a patient, e.g., to increase, enhance or facilitate delivery of the therapeutic agent across the blood-brain-barrier. Administration of the pharmaceutical formulations can be by a variety of methods. Methods can include systemic administration, wherein the polypeptide or composition of polypeptides is delivered to sites in the body, including the targeted site of pharmaceutical action, via the circulatory system. Systemic administration includes, but is not limited to, oral and parenteral (i.e., other than through the alimentary tract, e.g., intramuscular, intravenous, intrapulmonary, intranasally, inhalationally, intra-arterial, transdermal and subcutaneous) administration.

iii. Dosing

The M36 fungalysin metalloprotease (e.g., MPR1), or an enzymatically active fragment thereof, in conjunction with a therapeutic agent can be administered for prophylactic and/or therapeutic treatments. In therapeutic applications, compositions comprising the M36 fungalysin metalloprotease (e.g., MPR1), or an enzymatically active fragment thereof, in conjunction with a therapeutic agent are administered to a patient suffering from or at risk of developing disease of the CNS (e.g., a neurodegenerative disorder or a cancer of the CNS) in an amount sufficient to cure or at least partially arrest the disease and its complications. An amount adequate to accomplish this is defined as a "therapeutically effective dose." Amounts effective for this use will depend upon the severity of the disease and the general state of the patient's health, and clinical studies are often done to determine the best dose for a given cancer type. An effective amount of the compound is that which provides either subjective relief of a symptom(s) or an objectively identifiable improvement as noted by the clinician or other qualified observer.

In prophylactic applications, compositions M36 fungalysin metalloprotease (e.g., MPR1), or an enzymatically active fragment thereof, in conjunction with a therapeutic agent are administered to a patient not already in a disease state to prevent or delay the onset or recurrence of disease. Such an amount is defined to be a "prophylactically effective dose." In this use, the precise amounts again depend upon the patient's state of health.

Determination of an effective amount is well within the capability of those skilled in the art, especially in light of the detailed disclosure provided herein. Generally, an efficacious or effective amount of a combination of one or more polypeptides of the present invention is determined by first administering a low dose or small amount of a polypeptide or composition and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the present invention are described, for example, in Brunton, et al., Goodman and Gilman's The Pharmacological Basis of Therapeutics, Twelfth Edition, 2010, McGraw-Hill Professional; in a Physicians' Desk Reference (PDR), 65th Edition, 2011; in Remington: The Science and Practice of Pharmacy, 21st Ed., 2006, supra; and in Martindale: The Complete Drug Reference, Sweetman, 2005, London: Pharmaceutical Press., and in Martindale, Martindale: The Extra Pharmacopoeia, 31st Edition., 1996, Amer Pharmaceutical Assn, each of which are hereby incorporated herein by reference. In various embodiments, where a known compound is administered in conjunction with a M36 fungalysin metalloprotease (e.g., MPR1), or an enzymatically active fragment thereof, the dose is equivalent to or less than the recommended published dose, e.g., as can be found in the published literature or in the references cited above.

Exemplary doses of the pharmaceutical formulations described herein, include milligram or microgram amounts of the M36 fungalysin metalloprotease (e.g., MPR1), or an enzymatically active fragment thereof, in conjunction with a therapeutic agent per kilogram of subject or sample weight (e.g., about 1 microgram per-kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of the M36 fungalysin metalloprotease (e.g., MPR1), or an enzymatically active fragment thereof, in conjunction with a therapeutic agent depend upon the potency of the composition with respect to the desired effect to be achieved. When the M36 fungalysin metalloprotease (e.g., MPR1), or an enzymatically active fragment thereof, in conjunction with a therapeutic agent are to be administered to a mammal, a physician, veterinarian, or researcher may, for example, prescribe a relatively low dose at first, subsequently increasing the dose until an appropriate response is obtained. In addition, it is understood that the specific dose level for any particular mammal subject will depend upon a variety of factors including the activity of the specific composition employed, the age, body weight, general health, gender, and diet of the subject, the time of administration, the route of administration, the rate of excretion, any drug combination, and the degree of expression or activity to be modulated.

The appropriate dosage of the polypeptides of the present invention will vary according to several factors, including the chosen route of administration, the formulation of the composition, patient response, the severity of the condition, the subject's weight, and the judgment of the prescribing physician. The dosage can be increased or decreased over time, as required by an individual patient. Usually, a patient initially is given a low dose, which is then increased to an efficacious dosage tolerable to the patient.

The dosage of M36 fungalysin metalloprotease (e.g., MPR1), or an enzymatically active fragment thereof, in conjunction with a therapeutic agent administered is dependent on the species of warm-blooded animal (mammal), the body weight, age, individual condition, surface area of the area to be treated and on the form of administration. The size of the dose also will be determined by the existence, nature, and extent of any adverse effects that accompany the administration of a particular compound in a particular subject. A unit dosage for administration to a mammal of about 50 to 70 kg may contain between about 5 and 500 mg of the active ingredient. Typically, a dosage of the M36 fungalysin metalloprotease (e.g., MPR1), or an enzymatically active fragment thereof, in conjunction with a therapeutic agent, is a dosage that is sufficient to achieve the desired effect.

Optimum dosages, toxicity, and therapeutic efficacy of compositions can further vary depending on the relative potency of individual compositions and can be determined by standard pharmaceutical procedures in cell cultures or experimental animals, for example, by determining the LD50 (the dose lethal to 50% of the population) and the ED50 (the dose therapeutically effective in 50% of the population). The dose ratio between toxic and therapeutic effects is the therapeutic index and can be expressed as the ratio, LD50/ED50. Compositions that exhibit large therapeutic indices are preferred. While compositions that exhibit toxic side effects can be used, care should be taken to design a delivery system that targets such compositions to the site of affected tissue to minimize potential damage to normal cells and, thereby, reduce side effects.

The data obtained from, for example, animal studies (e.g., rodents and monkeys) can be used to formulate a dosage range for use in humans. The dosage of polypeptides of the present invention lies preferably within a range of circulating concentrations that include the ED50 with little or no toxicity. The dosage can vary within this range depending upon the dosage form employed and the route of administration. For any composition for use in the methods of the invention, the therapeutically effective dose can be estimated initially from cell culture assays. A dose can be formulated in animal models to achieve a circulating plasma concentration range that includes the IC50 (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC).

In general, the dose equivalent of a polypeptide or composition, is from about 1.0 ng/kg to 100 mg/kg for a typical subject. In various embodiments, a typical polypeptide composition of the present invention for intravenous administration can be in the range of about 1 ng/kg to 100 mg/kg per patient per day, for example, about 1.0 µg/kg to 10 mg/kg per patient per day. In various embodiments, dosages from about 10 µg/kg to 1.0 mg/kg per patient per day may be used. Actual methods for preparing administrable compositions will be known or apparent to those skilled in the art and are described in more detail in such publications as Remington: The Science and Practice of Pharmacy, 21st Ed., 2006, Lippincott Williams & Wilkins.

In one embodiment of the present invention, a pharmaceutical formulation of the present invention is administered, e.g., in a daily dose in the range from about 1 ng of compound per kg of subject weight (1 ng/kg) to about 100 mg/kg. In another embodiment, the dose is a dose in the range of about 1.0 µg/kg to about 50 mg/kg. In yet another embodiment, the dose is about 10 µg/kg to about 25 mg/kg. In another embodiment, the dose is about 25 µg/kg to about 15 mg/kg.

Exemplary doses of the pharmaceutical formulations can include 100-500 mg daily doses as needed, depending on the therapeutic agent to be delivered. Pharmaceutical formulations can be administered at a concentration of about 25 mg/mL to about 50 mg/mL. Exemplary doses of the pharmaceutical formulations can include about 5-20 mg/kg, for example, about 10 mg/kg daily doses.

In embodiments involving the administration of the M36 fungalysin metalloprotease (e.g., MPR1), or an enzymatically active fragment thereof, attached or conjugated to a nanoparticle encapsulating a therapeutic agent (e.g., a chemotherapeutic agent or an agent to mitigate symptoms of a neurodegenerative disease), the decorated and loaded nanoparticle can be administered at a dose in the range of about 5 mg/kg to about 200 mg/kg, for example, at a dose in the range of about 10 mg/kg to about 100 mg/kg, for example at a dose of about 5, 10, 15, 25, 50, 75, 100, 150 or 200 mg/kg. Because the decorated nanoparticles are targeted to the CNS by the attached or conjugated M36 fungalysin metalloprotease (e.g., MPR1), or an enzymatically active fragment thereof, doses of encapsulated chemotherapeutic agent can be higher within the nanoparticle than if the chemotherapeutic agents were administered alone (i.e., not encapsulated in the nanoparticle). In some embodiments, the doses of nanoparticle-encapsulated chemotherapeutic agent are 1-fold, 2-fold, 3-fold, 4-fold, or more, in comparison to doses of the same chemotherapeutic agent administered without encapsulation in the nanoparticle. Doses of unencapsulated chemotherapeutic agents are known in the art. See, e.g., Brunton, et al., Goodman and Gilman's The Pharmacological Basis of Therapeutics, Twelfth Edition, 2010, McGraw-Hill Professional and Physicians' Desk Reference (PDR), 65th Edition, 2011.

Following successful treatment, it may be desirable to have the subject undergo maintenance therapy to prevent the recurrence of the disease or malignant condition treated.

iv. Scheduling

Dosing schedules can be calculated from measurements of polypeptides in the body of a subject. In general, dosage is from 1 ng to 1,000 mg per kg of body weight and may be given once or more daily, semiweekly, weekly, biweekly, semimonthly, monthly, bimonthly or yearly, as needed or appropriate. Persons of ordinary skill in the art can easily determine optimum dosages, dosing methodologies and repetition rates. One of skill in the art will be able to determine optimal dosing for administration of a polypeptide or polypeptide composition of the present invention to a human being following established protocols known in the art and the disclosure herein.

Single or multiple administrations of the pharmaceutical formulations may be administered depending on the dosage and frequency as required and tolerated by the patient. In any event, the composition should provide a sufficient quantity of the polypeptides of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

The daily dose can be administered once per day or divided into subdoses and administered in multiple doses, e.g., twice, three times, or four times per day. However, as will be appreciated by a skilled artisan, compositions described herein may be administered in different amounts and at different times. The skilled artisan will also appreciate that certain factors may influence the dosage and timing required to effectively treat a subject, including but not limited to the severity of the disease or malignant condition, previous treatments, the general health and/or age of the subject, and other diseases present. Moreover, treatment of a subject with a therapeutically effective amount of a composition can include a single treatment or, preferably, can include a series of treatments.

In various embodiments, a pharmaceutical formulation thereof for intravenous administration would be about 0.01 to 100 mg/kg per patient per day. Dosages from 0.1 up to about 1000 mg/kg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as Remington: The Science and Practice of Pharmacy, 21st Ed., 2006, Lippincott Williams & Wilkins.

To achieve the desired therapeutic effect, pharmaceutical formulations may be administered for multiple days at the therapeutically effective daily dose. Thus, therapeutically effective administration of compositions to treat a disease or malignant condition described herein in a subject may require periodic (e.g., daily) administration that continues for a period ranging from three days to two weeks or longer. Typically, compositions will be administered for at least three consecutive days, often for at least five consecutive days, more often for at least ten, and sometimes for 20, 30, 40 or more consecutive days, or longer, as needed. While consecutive daily doses are a preferred route to achieve a therapeutically effective dose, a therapeutically beneficial effect can be achieved even if the compounds or compositions are not administered daily, so long as the administration is repeated frequently enough to maintain a therapeutically effective concentration of the composition in the subject. For example, one can administer a composition every other day, every third day, or, if higher dose ranges are employed and tolerated by the subject, once a week.

EXAMPLES

The following examples are offered to illustrate, but not to limit the claimed invention.

Example 1

Invasion of the Central Nervous System by *Cryptococcus neoformans* Requires a Secreted Fungal Metalloprotease Methods Transcytosis Screen for Mutants Defective at Crossing the In Vitro Blood-Brain-Barrier (BBB) Model The in vitro model of the BBB was established here as previously described (Vu, et al., *Eukaryotic Cell* 8:1803-1807). Briefly, the in vitro BBB model consists of a transwell apparatus separating the luminal (blood) and abluminal (brain) side of the BBB. HCMEC/D3 cells were grown in the top transwell chamber on collagen-coated microporous membrane (8 µm). Fungal cells ($1\times10^5$ cells) were added to the top chamber and collected subsequently from the bottom chamber for CFU determination.

Adhesion/Cell Association Assay of *C. neoformans* with HCMEC/D3 Cells

HCMEC/D3 were grown to confluence on collagen-coated transwells as discussed above. An innoculum of $1\times10^6$ *C. neoformans* cells in 50 µl PBS volume was added to the endothelial barrier at the start of the experiment. After the indicated amount of incubation time, the endothelial barrier was washed 3 times with 1×PBS and were either lysed with water to determine the number of yeast cells that adhered to and associated with the barrier or incubated overnight to assess the number of yeast cells that transmigrated the barrier after the initial adhesion step. This last transcytosis step was done to show that a transcytosis defect follows an initial adhesion defect.

Scanning Electron Microscopy (SEM)

HCMEC/D3 cells were grown on transwell filters (8 µm; BD Biosciences) under the same conditions used for the transcytosis assays. Approximately $2\times10^6$ cells of a wild-type strain of *C. neoformans* (H99) were added to the top chamber for 1 h. The transwell filters were then washed with 1×PBS to remove nonspecific adhering yeast cells, fixed in Karnovsky's fixative, and sent to an on-campus SEM facility for sample processing (Electron Microscopy Lab, UC Davis). For SEM preparation of *C. neoformans* in the absence of an endothelial barrier, the fungal cells were grown overnight in YPD, washed in PBS, spun down, and fixed in Karnovsky's fixative.

Macrophage Intracellular Survival Assay

J774A.1 (ATCC TIB-67, from Dr. Renee Tsolis) is a macrophage-like cell line from a BALB/c haplotype H-2d, reticulum sarcoma used in the assay. Macrophages were grown at 37° C. with 10% $CO_2$ in DMEM (Gibco #11995) supplemented with 10% heat-inactivated fetal bovine serum (Invitrogen #16140-071), 1% non-essential amino acids (Gibco #21340), 50 µg/ml penicillin-streptomycin (Gibco #15070-063), and 10% NCTC-109 medium (Gibco #11140). J774A.1 was grown in 25 $cm^2$ or 75 $cm^2$ flasks (Thermo Sci Nunc #, 136196 or 156499) and used between passages 4-15.

For the assay, $2.5\times10^5$ J774A.1 cells were counted using a hemacytometer (Hausser Scientific #1475) and grown in 96-well culture plates (BD Falcon 353072) overnight. *C. neoformans* was cultured overnight in YPD+2% glucose at 30° C. with agitation. Cultures were then synchronized and normalized based on absorbance value measured at OD600 and allowed to grow overnight. Using a hemacytometer, $1\times10^6$ *C. neoformans* cells were added to macrophages supplemented with 100 U/ml mouse IFN-gamma (Thermo Sci Pierce Protein Research products #RM200120), 0.3 µg/ml LPS (Sigma #L4391), and 1 µg/ml mAb18B7 (a gift from Arturo Casadevall) for 1 hour. Cells were washed 3 times with 1×PBS and either incubated overnight with fresh DMEM+supplemental media or lysed with 100 of ice cold 0.05% SDS for CFU determination. The following day, the media was removed from wells and macrophages were lysed using 100 µl of ice cold 0.05% SDS. Lysed macrophages were serially diluted and plated on YPD+P/S plate for 48 hours at 30° C. for yeast intracellular survival analysis.

Inhalation Model (Survival Study and CFU Analysis)

Experimental Parameters.

$1\times10^7$ yeast cells in 50 ml volume were used to innoculate mice. Mice (A/J strain, Jackson Laboratories, 000646) were 5 weeks old, inbred, and housed with 3-4 animals per cage. The number of animals used per groups (WT, reconstituted, and mutant) was 7.

Preparation of Yeast Innoculum.

Frozen stocks of the 3 yeast strains used in the study (WT, mp102Δ, and Rec1) were streaked on YPD plates and incubated overnight at 30° C. Colonies were then grown in liquid YPD overnight at 30° C. until log phase (approx. 16 hours). Cultures were re-grown a second time (to log phase) by adding 100 µL of liquid culture into fresh YPD to ensure yeast colonies are robust. 10 ml of each cultured strain were cleaned with sterile 1×PBS (4000 rpm, 4 minutes, @ 25° C.) and re-suspended in YPD. The concentration of the original culture was determined by hemacytometer count (Brite-Line) and was diluted in 1× sterile PBS to a final concentration of $2\times10^8$ cells/ml (equates to $1\times10^7$ cells/50 ml volume).

Inoculation (Survival Assay).

Upon arrival to our animal facilities, 4 week old mice were given 1 week to acclimate, and given food and water ad libitum. Experiments were conducted in a separate surgical room. Mice were placed under 5% isoflurane anesthesia (2.5% maintenance dose), inoculated with $1\times10^7$ cells in 50 µl volume through the nares. The animals were suspended by their top incisors to hold their head back, ensuring that the inoculum was inhaled smoothly with minimal obstruction. Upon applying the inoculum, mice were suspended for another 30 seconds to ensure all of the inoculum was inhaled. Changes in the health status of the animals were monitored and bodyweight recorded daily until they showed signs of sickness due to the infection. Mice were sacrificed when a loss of 15% of body peak body weight was observed or when a loss of 1 g of body weight was observed for 3 consecutive days. Other signs of sickness monitored included lethargy, lack of activity and grooming (indicated by ruffled fur). Mice were sacrifice by an overdose of pentobarbital (Fatal Plus, MWI Veterinary Supply) at 150 mg/kg bodyweight. Survival data was collected and analyzed on Prism 5.0 software.

Tissue Homogenization (CFU Analysis).

Lung and brain were collected for homogenization as soon as possible after the animals were sacrificed. Lungs were cut into several pieces and mashed dry with a mortar and pestle for 1 min and suspended in 5 ml of 1×PBS. Brains were mashed dry for 30 seconds and suspended in 1×PBS. Original homogenized tissue was designated as 1×. Lung tissue was serially diluted with 1×PBS into 100×, 1000×, and 10000× dilutions; brain tissue was diluted to 10×, 100×, and 1000× dilutions. 100 ml of each respective dilution was spread on YPD plates containing Penicillin/Streptomycin and incubated for 2 days at 30° C. Total CFUs were calculated based on the number of colonies counted on the plate, plating volume (100 ml), dilution (from 1× to 10000×), and the original volume of the homogenized tissue (5 mL). With a few exceptions, we tried to count plates with at least 100 colonies to maximize accuracy. CFU data was analyzed on Prism 5.0 software.

Intravenous Model (Survival Study and CFU Analysis)

Experimental Parameters:

$1.2\times10^6$ yeast cells in 200 ml volume were used to inoculate mice. Mice (A/J strain, Jackson Laboratories, 000646) were 8 weeks old, inbred, and housed with 3-4 animals per cage. The number of animals used per groups (WT, reconstituted, and mutant) was 8.

Preparation of Yeast Inoculum:

As described above. The concentration of the original culture was diluted in YPD to a final concentration of $6 \times 10^6$ cells/ml (equates to $1.2 \times 10^6$ cells/200 ml total volume.

Inoculation (Survival Assay).

Upon arrival to our animal facilities, 7 week old mice were given 1 week to acclimate, and given food and water ad libitum. Experiments were conducted in a separate surgical room. A/J mice, under 3% isoflurane anesthesia (1% maintenance dose as needed), were inoculated with $1.2 \times 10^6$ cells in 200 μl total volume through the lateral tail vein. Mice were held briefly in a restrainer (Kent Scientific) during anesthesia and injection. Once the tail vein became dilated by heat lamp it was disinfected with alcohol swabs (Becton-Dickinson). 30G1/2 needles (Becton-Dickinson) and 1 ml tuberculin syringes (Kendall) were used. In the event that an injection was done incorrectly, the syringe was refilled with more inoculum to replace any lost during the incomplete injection. After injection was complete, mice were given fresh oxygen until they become awake. Mice were monitored as discussed above and sacrificed with an overdose of pentobarbital (Fatal Plus, MWI Veterinary Supply) at 150 mg/kg bodyweight.

CFU Analysis.

Brains were collected for homogenization immediately after the animals were sacrificed. Brains were mashed on a mortar and pestle dry for 30 seconds and resuspended in 5 ml of 1×PBS. Original homogenized tissue was designated as 1×. Brain tissue was serially diluted with 1×PBS into 10×, 100×, and 1000× dilutions (1 mL of homogenate into 9 ml 1×PBS). 100 ml of each respective dilution was spread on YPD containing Penicillin/Streptomycin, and incubated for 2 days at 30° C. Total CFUs was calculated based on the number of colonies counted on the plate, plating volume (100 ml), dilution (from 1× to 1000×), and the original volume of the homogenized tissue (5 mL).

Intravenous Model—Brain Burden Time Course (CFU Analysis and Histology)

Experimental Parameters.

$5 \times 10^5$ yeast cells in 200 μl volume were used to inoculate mice. Mice (A/J strain, Jackson Laboratories, 000646) were 8 weeks old, inbred, and housed with 3-4 animals per cage. The number of animals used per groups (WT and mutant) was 4 per time point (12 hr, 48 hr, 72 hr). 3 animals per group used for CFU analysis, and 1 was saved for histology.

Preparation of Yeast Inoculum.

(As described above). The concentration of the original culture was diluted in 1× sterile PBS to a final concentration of $2.5 \times 10^6$ cells/ml (equates to $5 \times 10^5$ cells/200 ml total volume).

Inoculation (CFU Analysis).

Injection protocols were the same as discussed above. Mice were sacrificed at 12, 24, and 72 hours, respectively, with Pentobaritol (150 mg/kg of bodyweight). Brains, extracted immediately following euthanasia, were mashed dry for 30 seconds and suspended in 3 mL YPD (designated as 1×). The homogenate was serially diluted to 100× and 100× (200 ml of homogenate diluted in 1800 ml YPD). 200 ml of each respective dilution was spread on YPD plates containing Pen/Strep and incubated for 2 days at 30° C. Total CFUs were calculated based on the number of colonies counted on the plate, plating volume (200 ml), dilution (from 1× to 100×), and the original volume of the homogenized tissue (3 mL).

Histology.

Brains were fixed in 4% paraformaldehyde prior to sectioning. Sectioning was carried about by UC Davis veterinary laboratory (slice thickness, stain used, and how tissue was analyzed for lesions).

Intra-Parenchyma Survival Study (CFU Analysis Only)

Experimental Parameters.

$1 \times 10^4$ yeast cells in 60 ml volume were used to inoculate mice. Mice (A/J strain, Jackson Laboratories, 000646) were 10 weeks old, inbred, and housed with 3-4 animals per cage. The number of animals used per groups (WT, reconstituted, and mutant) was 6 (WT and mp102Δ).

Preparation of Yeast Inoculum.

(As described above). The concentration of the original culture was diluted in 1× sterile PBS to a final concentration of $1.67 \times 10^6$ cells/ml (equates to $1 \times 10^4$ cells/60 ml total volume).

Inoculation (CFU Analysis).

Mice were anesthetized using isoflurane anesthesia and randomized for intracranial inoculation of *C. neoformans* (wild type and mpr1Δ mutant strains). Inoculation was delivered as a 60 μl volume through a 27-gauge needle fastened to a tuberculin syringe with a cuff to prevent penetration of more than 1 mm. A midline puncture through the cranial vault approximately 6 mm posterior to the orbit was made and the inoculum was injected after which the mice allowed to recover. Euthanasia protocol was the same as described above. Mice were sacrificed at 48 hours with Pentobarbitol (150 mg/kg of bodyweight). Brains, extracted immediately following euthanasia, were mashed dry for 30 seconds and suspended in 3 mL of YPD (designated as 1×). The homogenate was serially diluted to 10× and 100× dilutions (200 ml of homogenate was diluted in 1800 ml YPD). 200 ml of each respective dilution was spread on YPD+Pen/Strep and incubated for 2 days at 30° C. Total CFUs were calculated based on the number of colonies counted on the plate, plating volume (200 ml), dilution (from 1× to 100×), and the original volume of the homogenized tissue (3 ml).

Results and Discussion

In order for *C. neoformans* to breach the brain endothelium and colonize the brain parenchyma, we proposed that proteins on the surface of cryptococcal cells were likely to have a crucial role. Since so little was known about the extracellular proteome of *C. neoformans* we performed the first proteomic analysis and discovered that many of the proteins that *C. neoformans* secretes include several different types of proteases (Eigenheer, et al., (2007) *FEMS Yeast Research* 7:499-510). Among the secreted proteases we identified were, serine proteases, aspartic proteases and metalloproteases (Eigenheer, et al., (2007) *FEMS Yeast Research*, supra). Although it had been suspected that *C. neoformans* produced extracellular enzymes, their identity and role in the pathogenesis of *C. neoformans* was unknown (Pinti, et al., (2007) *FEBS Lett* 581:3882-3886; and Aoki, et al., (1994) *Mycopathologia* 128:143-150).

Figure 1B:
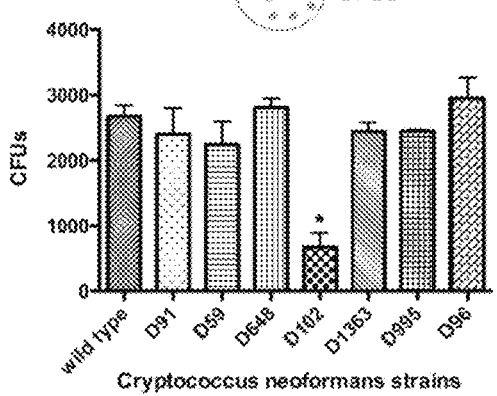
Figure 1C:
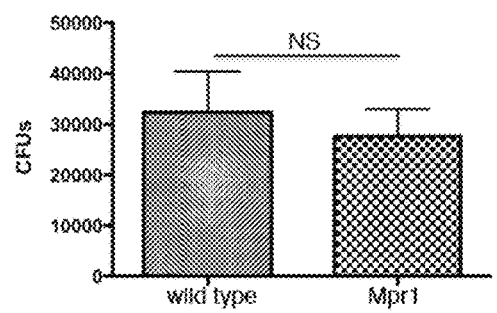

To determine whether extracellular proteases of *C. neoformans* played a role in the transmigration of cryptococci into the CNS, strains of *C. neoformans* that lacked proteases were examined in an in vitro model of the BBB (FIG. 1A) (Vu, et al., (2009) *Eukaryotic Cell* 8:1803-1807). In this model, human cerebral microvascular endothelial cells (HC-MEC/D3 cells) were grown as a monolayer on a transwell insert submerged in media specific for endothelial cells. Cryptococci (H99 serotype A strain) were added to the luminal side (blood side) of the monolayer, collected from the abluminal side (brain sides) of the monolayer 24 h later and added to YPD agar plates for CFU (colony forming units) determination (FIG. 1a). Remarkably, we found that a strain of *C. neoformans* that lacked a newly identified metalloprotease, MPR1, was significantly defective in crossing the endothelium compared to a wild type strain of *C. neoformans* (FIG. 1b). This defect was not due to media effects (such as the presence of serum or growth factors), or an inability to tolerate 5% $CO_2$ or 37° C. since both the background (wild type) strain and the mpr1Δ mutant strain behaved similarly in the growth conditions required for brain endothelial cells (FIG. 1c and FIG. 5). We verified the mpr1Δ null mutant strain by southern blot analysis (FIG. 5) and found that it retained all inherent virulence traits such as capsule and melanin formation, urease and laccase production.

Figure 1D:
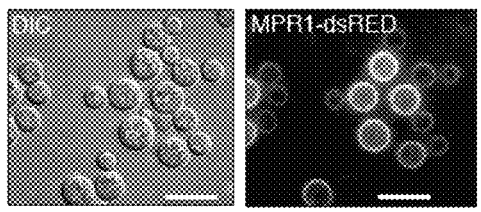
Figure 1E:
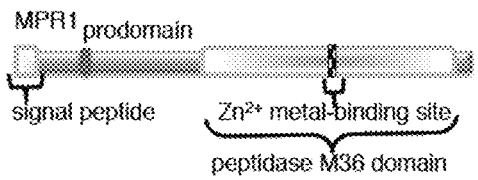

In silico analysis revealed that MPR1 is 525 aa long, it has a predicted signal peptide at the N-terminus, a predicted propeptide (FTP domain), and a peptidase M36 catalytic domain with a highly-conserved $Zn^{2+}$ binding motif near the C-terminus (FIG. 1e). We found that only one copy from this particular class of metalloproteases exists in the genome of *C. neoformans* (Eigenheer, et al., (2007) FEMS Yeast Research, supra). At the amino acid level, MPR1 is most similar (65%) to an elastolytic metalloprotease from *Aspergillus fumigatus* (Eigenheer, et al., (2007) FEMS Yeast Research, supra). Although the metalloprotease in *Aspergillus* has been shown to have some activity against elastin, this was not the case for CnMPR1.

We constructed an MPR1-dsRED fusion protein and expressed it in the mpr1Δ mutant background strain to assess its localization. Fluorescence microscopy demonstrated that MPR1 localized to the surface of *Cryptococcus* strongly suggesting that it is an extracellular protein (FIG. 1d). This result is further supported by the presence of the predicted N-terminal signal peptide in MPR1 and by our proteomic analysis where we identified MPR1 as a secreted protease Eigenheer, R. A., et al., (2007) *FEMS Yeast Res*, supra). We have also confirmed the proteolyic activity of MPR1 and our studies have shown that the recombinant metalloprotease protein does maintain proteolytic activity but collagen, laminin or elastin do not appear to be substrates. The M36 fungalysins, found only in bacteria and fungi, appear to mediate some aspects of the host-fungal interaction in *A. fumigatus* and some bacidiomycetes but the identity of their substrates remains unknown (Lilly, et al., (2008) *Mycological Res* 112:389-398).

The transmigration of *C. neoformans* (wild type strain) across the brain endothelium observed here is consistent with a transcellular mechanism whereby cryptococci cross the endothelial cells with little or no disruption of the intercellular tight junctions (i.e., paracellular mechanism). This observation is supported by previous reports that have shown both in vitro and in vivo that cryptococci breach the endothelium through an active process that involves the formation of microvilli on the surface of endothelial cells that presumably facilitate the transcellular movement (Chang, et al., (2004) *Infect Immun* 72:4985-4995; and Vu, et al., (2009) *Eukaryotic Cell* 8:1803-1807). The inability of the mp1Δ mutant strain to cross the brain endothelium suggests that MPR1 promotes transcellular migration by facilitating an aspect of this multistep process—adhesion, invasion, transmigration and/or extrusion from the brain endothelium.

To examine if MPR1 was required for adherence of cryptococcal cells to the brain endothelium we performed an adherence assay with the in vitro BBB model. Here, cryptococci ($1\times10^6$) of a wild type strain, the mpr1Δ mutant strain and the reconstituted strain were added to the top chamber of a transwell insert of the BBB model described above (FIG. 1a). Following a 2 h incubation (at 37° C. and 5% $CO_2$) excess cells that had not adhered were washed away several times with PBS. To collect cells of *C. neoformans* that did adhere to endothelial cells, Millipore water was added to the top transwell insert resulting in the rupture of the endothelial cells (HBMEC/D3). The attached cryptococcal cells were recovered and plated to determine CFUs. The CFUs revealed how much of the initial inoculum of the mpr1Δ strain adhered to the endothelium compared to the wild type strain thus we were able to determine if the mpr1Δ strain had an adherence defect. For the transcytosis assay (i.e. to determine whether cryptococci could cross the endothelium) cells were collected from the bottom chamber (FIG. 1a).

Interestingly, we found that MPR1 is required for adhering cryptococcal cells to the surface of brain endothelial cells as demonstrated by the low CFU counts for the mp102Δ mutant strain (FIG. 2a). Accordingly after 24 h significantly less mp102Δ mutant cells crossed the barrier after the initial 2 h incubation compared to cells of the wild type strain and the reconstituted strain (FIG. 2b). Increasing the incubation time of the mp102Δ mutant strain with the brain endothelium did not promote the adherence of mp102Δ cryptococci as demonstrated by CFUs counts determined following 8 h incubation (FIG. 2c). Our results are consistent with the conclusion that cryptococcal cells lose their ability to adhere to the brain endothelium in the absence of MPR1 and therefore cannot transmigrate the endothelium. We found through ultrastructure examination by scanning electron microscopy that the overall surface structure and morphology of mpr1Δ mutant cells and the brain endothelial cells appeared altered suggesting that MPR1 may be transforming the extracellular environment by possibly unmasking surface receptors, ligands and/or adhesion proteins (FIG. 2d).

A major objective of this study was to determine the contribution of MPR1 to the virulence of *C. neoformans* in terms of survival and CNS invasion after pulmonary infection in a mammalian host. To do this, mice were inoculated via the intranasal route to mimic the natural path of infection. We then examined cumulative survival and lung and brain pathologies. We found that by day 40 post-infection no mortality had occurred in mpr1Δ-infected mice whereas 100% of wild type-infected mice died (FIG. 3a, $P=0.001$) and at day 54 post-infection, 15% of mpr1Δ-infected mice remained alive. These results demonstrated that the lack of MPR1 significantly prolonged survival suggesting it is a major contributor to the pathogenesis of *C. neoformans*. Interestingly, SAGE analysis revealed that the expression of the gene encoding MPR1 was specifically induced in cryptococcal cells during brain infection in a rabbit model of cryptococcal meningitis but not in vitro at 37° C. (Steen, et al., (2003) *Eukaryot Cell* 2:1336-1349). These results further support a role for this protease in establishing fungal disease of the CNS (Steen, et al., (2003) Eukaryot Cell, supra).

Total lung CFU analysis at the time of death revealed high cryptococcal burden in mpr1Δ-infected mice that was similar to CFU in lungs of mice infected with the wild type strain (FIG. 3b). These data suggested that the improved survival of mpr1Δ-infected mice was not due to enhanced clearance of the mpr1Δ-induced infection from the lungs—the primary site of infection. We also found that the lack of MPR1 from *C. neoformans* significantly reduced fungal burden in the brain following pulmonary inoculation (FIG. 3c, $P=0.009$, CFUs taken at time of death). This suggested that MPR1 promotes the transmigration of *C. neoformans* into the CNS.

It is not surprising however, that at the time of death some cryptococcal cells could be detected in brains from mpr1Δ-infected mice (FIG. 3c) since we anticipate that other virulence factors (and other mechanisms such as "Trojan horse"—phagocyte associated invasion) are involved in promoting CNS invasion by *C. neoformans* (Charlier, et al., (2009) *Infect Immun* 77:120-127; Chretien, et al., (2002) *J Infect Dis* 186:522-530; and Olszewski, et al., (2004) *Amer J of Path* 164:1761-1771). For example, urease, has been shown to be a key player in promoting the sequestration of cryptococcal cells within the brain microvasculature (Olszewski, et al., (2004) *Amer J of Path*, supra). Increasing evidence about cryptococcal virulence factors would suggest that a combination of factors rather than a single one is most likely involved in the multistep process of cryptococcal dissemination and CNS invasion. In addition, prolonged exposure of the brain endothelium to cryptococci results in the eventual break down of the barrier and disruption of brain endothelial cells and this would allow the passive movement of cryptococci into the brain (Chretien, et al., (2002) *J Infect Dis*, supra).

When mice were inoculated by tail vein injection, as a means to bypass the lungs and allow a direct route to the brain, we found that by day 21 post-infection 100% of mpr1Δ-infected mice were alive and 100% of wild type-infected mice had died suggesting that the lack of mpr1Δ significantly prolonged survival in this murine model as well (FIG. 3d, P=0.0002). Following the tail vein inoculation, we examined the fungal burden at 12 h, 24 h, and 48 h post-infection in whole brains of mice infected with mpr1Δ and wild type strains. CFUs revealed a significant increase in cryptococci in whole brains of mice infected with a wild type strain (FIG. 3e).

In contrast, whole brain CFUs at 24 h and 48 h post-infection revealed significantly less fungal burden in the brains from mpr1Δ-infected mice (FIG. 3e, P<0.0001). Because our histological analysis (FIG. 4) revealed no pathology in brains of mice infected with the mpr1Δ mutant strain, it is very likely that the CFUs observed at 12 h post-infection are a reflection of mpr1Δ-cryptococci lingering in the vessels because, as was observed in the in vitro model of the BBB, they are unable to adhere to and cross the blood-brain barrier.

At 16-days post-infection, the brain fungal burden in mice inoculated with mpr1Δ was significantly less than the fungal burden in brains of mice infected with the wild type strain (FIG. 3f). Taken together, the in vivo data strongly suggested that the mpr1Δ mutant strain was defective in crossing the brain endothelium and invading the brain parenchyma, however we could not rule out the possibility that the significantly lower CFU counts detected in whole brains of mice infected with the mpr1Δ mutant strain might instead reflect a requirement for MPR1 in intra-parenchyma brain survival. To address this, brains of mice were directly inoculated with cryptococci by intracranial injections. The survival of both strains within the brain parenchyma was assessed by CFU counts from isolated brains. Here we found that the mpr1Δ mutant and wild type strains were equally able to proliferate within the brain parenchyma and thus we concluded that MPR1 is not required for the growth and survival of *C. neoformans* within the brain (FIG. 3g). Instead, MPR1 functions primarily to attach cryptococci to the surface of the brain endothelium.

Extensive histochemical analysis was performed in order to determine the extent of brain pathology in mice inoculated with mpr1Δ and wild type strains. Mice were inoculated by tail vein injection and brains were examined at 12 h, 24 h and 48 h post-infection by taking consecutive, longitudinal brain sections and staining with mucicarmine or hematoxylin and eosin (H&E). A significant number of cryptococcal filled-lesions (cysts) were observed in the brain parenchyma of wild type-infected mice 48 h post-infection often in close proximity to the microvessels (FIG. 4a). Here, cryptococci, in various stages of division, were easily identified within cysts that occurred throughout the brain tissue. Similarly, cryptococci were also observed within lesions in brains from mice 12 h and 24 h post-infection (FIG. 4e, 4g). Interestingly, brain sections were devoid of immune cells as demonstrated by the lack of neutrophils in brain sections stained with H&E (FIG. 7C). The lack of immune cells in the histochemical analysis of brain tissue is consistent with previous work that demonstrated that both in humans and in mice, inflammation in the brain tissue was limited presumably due to late production of low concentrations of tumor necrosis factor (TNF)-alpha and interlukin-6 in brains of infected mice (Chretien, et al., (2002) *J Infect Dis*, supra). In addition only low concentrations of these cytokines were found in the CSF of patients with AIDS who suffered from cryptococcal meningitis (Chretien, et al., (2002) *J Infect Dis*, supra).

In contrast, cryptococci-filled cysts were not detected in brains from mice inoculated with the mpr1Δ mutant strain at 12 h, 24 h, or 48 h post-infection. Remarkably, here, we observed intact brain tissue with healthy microvessels that were devoid of cryptococci (FIG. 4b, d, f, h). Our results are consistent with the conclusion that the mpr1Δ mutant strain did not invade the brain parenchyma even though strains were administered via a direct route to the CNS. The inability of the mutant strain to colonize the CNS strongly suggests that MPR1 has a direct role in promoting the transmigration of *C. neoformans* across the blood-brain barrier.

Example 2

Determination of Substrates of MPR1

Substrates define protease function so that in order to fully understand the role of MPR1 in the virulence and pathogenesis of *C. neoformans*, the substrates must be identified and their functional consequences resolved. MPR1 may be targeting proteins on the surface of the brain endothelium and/or targeting key proteins in *C. neoformans* that are involved in shaping the extracellular environment of cryptococcal cells. Based on what we know about metalloproteases in mammalian cells, it is very likely that MPR1 has multiple targets and likely functions as a key modulator within a "protease web". A system-wide approach offers one approach to resolving MPR1 proteolysis in order to understand its role in the transmigration of *C. neoformans* into the CNS. Proteomics or "degradomics" encompasses a powerful technique that can permit an unbiased high-throughput substrate discovery screen of MPR1. Liquid chromatography (LC)-mass spectrometry (MS)-based proteomic techniques allow substrate identification in complex biological systems like the *Cryptococcus*-brain endothelium interface. High-content proteomic screens have been highly successful in identifying substrates of metalloproteases. See, e.g., Dean and Overall, *Mol Cell Proteomics*. (2007) 6(4):611-23; Morrison, et al., (2009) *Curr Opin Cell Biol*. (2009) 21(5): 645-53. Native substrates of MPR1 (degradome) can be screened with a mass-spectrometry approach known as isobaric peptide tag labeling (iTRAQ LC-MS/MS)—an innovative, high-content and state-of-the-art proteomics technique that can identify and quantify proteins from different complex biological sources. See, e.g., Wu, et al., (2006) *J Proteome Res.* 5:651-658; Ow, et al., (2009) *J Proteome Res* 8:5347-5355).

iTRAQ LC-MS/MS as a High-Content Proteomic Screen to Identify the Degradome of MPR1.

Native substrates of MPR1 (degradome) are screened in the cellular context of the brain endothelium-cryptococcal interface using iTRAQ LC-MS/MS by comparing cells expressing MPR1 (H99 wild type strain) to control cells lacking the expression of MPR1 (mpr1Δ mutant strain). Tryptic peptides of cleaved proteins will be released into the culture medium, collected, tryptically digested, labeled with iTRAQ tags, and identified by LC-MS/MS (FIG. 7).

The in vitro model of the BBB is used to perform part of these studies (FIG. 7). Briefly, the two cryptococcal strains is incubated with human brain endothelial cells grown on transwells (as described above) for less than 2 h. According to our in vitro data, cryptococcal cells begin to cross the brain endothelium between 3 h to 6 h; therefore, significant changes on the surface of cryptococci and the brain endothelial cells early on. This notion is supported by the morphological changes observed on the surface of the brain endothelial cells in the presence of *Cryptococcus* within a 3 h timeframe. Serum-free conditions are used to increase specific iTRAQ labeling of proteins. Following incubation, the two sample supernatants are harvested, concentrated and tryptically digested. The two samples are differentially labeled with isobaric iTRAQ tags, that upon tandem mass spectrometry (MS/MS) fragmentation give quantifiable reporter ion peaks at m/z 114 and 115. Labeled samples are pooled and fractionated by two-dimensional liquid chromatography (2D-LC) using strong cation exchange and reverse-phase chromatography. Peptides are identified by MS/MS and quantified based on the ratio of the iTRAQ reporter groups.

The location within a protein (substrate) of the released cleaved fragment (peptide mapping) can also be determined because we can map identified peptides to the corresponding protein sequence and compare their iTRAQ abundance. Cleavage sites within the native substrate are identified.

Expected Outcome and Benchmarks:

1) anchored proteins targeted (substrates) by MPR1 that shed peptides from the cell surface microenvironment of brain endothelial cells (or cryptococcal cells) into the culture medium would show higher iTRAQ ratios for their tryptic peptides in H99 versus mpr1Δ mutant samples. In other words, the putative substrates will remain anchored to the surface if MPR1 is not around to cleave them, therefore fewer tryptic peptides would be seen in the mpr1Δ sample.

2) On the other hand, secreted proteins that are putative substrates of MPR1 will show low iTRAQ ratios in H99 compared to mpr1Δ reflecting proteolytic clearance. In this case, secreted substrates would be selectively degraded by MPR1. Therefore, tryptic peptides would be cleared in the H99 sample but would persist in the mpr1Δ mutant sample. Because of the high-proteome coverage provided by the iTRAQ approach we expect to successfully resolve a nearly complete degradome of MPR1.

The use of iTRAQ for identification and relative and absolute quantification of proteins in different samples has been a major breakthrough in quantitative proteomics. See, e.g., Wu, et al., (2006) *J Proteome Res.* 5:651-658; Ow, et al., (2009) *J Proteome Res* 8:5347-5355). High-content proteomic screens using iTRAQ have been highly successful in identifying substrates of metalloproteases expressed in mammalian cells. See, e.g., Dean and Overall, *Mol Cell Proteomics*. (2007) 6(4):611-23. Although we realize that we are dealing with a complex biological interface (*Cryptococcus*-brain endothelium), the amount of information that we will gain from using this approach will significantly contribute to our understanding of the highly neurotropic nature of *C. neoformans*. A successful outcome will not only establish this approach as an innovative and highly useful technique for the field of fungal pathogenesis, but it will also open the way for resolving the substrates and therefore function of other proteases we previously identified but whose functions remain unknown.

Example 3

Transformation with MPR1 or Conjugation to MPR1 Facilitates the Migration of Therapeutics into the Brain for the Treatment of Brain Disorders In order to examine whether the expression of Mpr1 alone could promote the movement of a non-pathogenic yeast across the blood-brain barrier, the cDNA of Mpr1 (from *Cryptococcus neoformans* var. *grubii*, H99 serotype A) was sub-cloned into a yeast expression plasmid and transformed into a wild type strain of yeast (*Saccharomyces cerevisiae*, W303). *S. cerevisiae* does not normally express the Mpr1 metalloprotease since this gene is not present in its genome. Using RT-PCR (reverse transcriptase polymerase chain reaction) we confirmed that *S. cerevisiae* does not normally express Mpr1 mRNA transcript, as expected, and that we successfully engineered *S. cerevisiae* to constitutively express CnMpr1 mRNA (FIG. 8b).

Figure 8C:
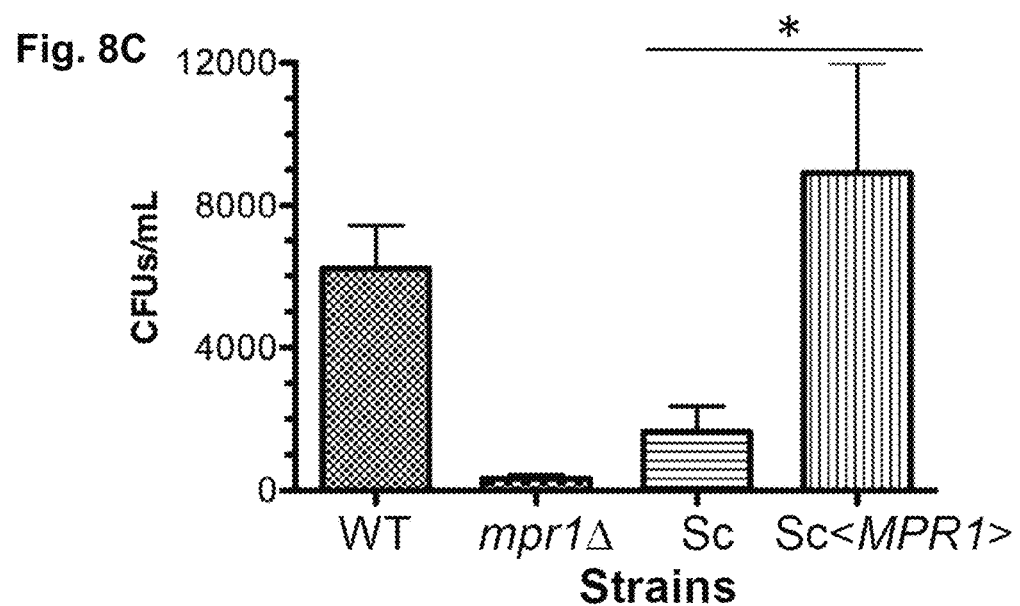

We performed transcytosis assays with our in vitro model of the blood-brain barrier (FIG. 8a) and found that wild type yeast (*S. cerevisiae*) that expressed CnMpr1 mRNA alone had remarkably gained the ability to cross the brain endothelium in significant numbers, similar to what we normally observe for *Cryptococcus neoformans* var. *grubii* (FIG. 8c, Sc<MPR1>). In contrast, wild type yeast (lacking expression of CnMpr1) did not cross the brain endothelium to any appreciable extent (FIG. 8c, Sc). These results are consistent with the conclusion that Mpr1 alone can promote the permeability of the blood-brain barrier, confirming its usefulness in delivering therapeutics to the brain.

Conjugation/attachment of Mpr1 to a therapeutic moiety (e.g., nanoparticles, liposomes, therapeutic agents, stem cells, and/or antibodies) finds use in specifically targeting the migration of the therapeutic moiety across the blood-brain barrier, providing a new therapeutic delivery system for the brain. The Mpr1-bioconjugated carriers can be engineered to carry a therapeutic payload (e.g., drug or antibodies) for the treatment of a specific brain disorder. Using MPR1 to promote delivery of a therapeutic moiety across the blood-brain barrier can facilitate and improve the treatment of brain disorders.

Mpr1-conjugated carriers can be used to specifically deliver to the brain therapeutic doses of a therapeutic agent and to maintain the therapeutic agent in the brain at levels that are effective in treating a specific brain disorder. In one embodiment, Mpr1-conjugated carriers are useful in the treatment of glioblastoma multiforme where patient survival rates are extremely low.

Example 4

Targeting Potential of Nanocarriers to the Brain by Engineering Mpr1-Conjugated Nanoparticles This example describes the generation of recombinant Mpr1 protein using a well-established eukaryotic expression system and the conjugation of Mpr1 to silicon-based nanoparticles. Silicon nanoparticles or quantum dots represent an exciting new type of nanoparticle with minimal cytotoxicity as well as being biodegradable. These nanoparticles have a large capacity for drug loading and they can be linked to an Mpr1 protein or peptide via the ~300 or so amine groups on the surface of the nanoparticle for targeted penetration. In addition, because silicon nanoparticles are intrinsically luminescent and they can be doped, e.g., with $Fe^{2+}$ or $Mn^{2+}$, and can be monitored, e.g., either by a fluorescence microscopy or MRI, respectively. Silicon nanoparticles or use are known in the art (Park, et al., *Nature Materials* (2009) 8:331-336; Tu, et al., JACS, (2010) 132:2016-2023; Zhang, et al., JACS, (2007) 129:10668; Singh M P et al., ACS Nano, (2012) In press, (DOI: 10.1021/nn301536n); Rosso-Vasic, et al., *J. Mater. Chem.* (2009) 19:5926-5933; Bhattacharjee S., et al., Nanotoxicology, (2011) DOI 10.3109/17435390.2011.633714, 1-14; Chandra, et al., Nanoscale (2011) 3:1533-1540) and find use for the generation of Mpr1-conjugated-silicon based nanoparticles. Mpr1-bioconjugated nanoparticles are examined in our in vitro model of the BBB in order to determine efficiency of binding to- and crossing the brain endothelium and to establish the biodegradability and biocompatibility of the bioconjugated nanoparticles. The Mpr1-bioconjugated nanoparticles are also evaluated in vivo in order to establish their biodistribution, in vivo degradation and cytotoxicity, e.g., employing positron emission tomography (PET), magnetic resonance imaging (MRI), optical fluorescence and other types of animal imaging approaches.

Bioconjugation of Mpr1, or a fragment thereof, increases the permeability of the BBB to a new type of silicon nanoparticle that can carry a therapeutic payload and is biodegradable. This drug delivery system improves the treatment of brain disorders. The combination of these two novel and specialized entities makes this approach highly innovative, uncomplicated and offers promising strategy for the treatment of brain disorders. This technology creates a doorway in the BBB that promotes the movement of clinically relevant drugs into the brain. Mpr1-conjugated nanoparticles allows existing therapeutic agents to be: 1) specifically delivered to the brain at optimal therapeutic doses and 2) maintained in the brain at levels that are effective in treating a specific brain disorder. This technology is particularly useful in the treatment of glioblastoma multiforme where patient survival rates are extremely low. Delivery of just a fraction of an anticancer drug into the brain improves patient survival.

Silicon nanoparticles as non-toxic, nanovectors and multimodal reporters. Semiconductor quantum dots (QDs) such as silicon (Si) nanoparticles, have recently received significant attention because they are multipotent and biocompatible (Tu, et al., *JACS*, (2010) 132:2016-2023; Rosso-Vasic, et al., *J. Mater. Chem.* (2009) 19:5926-5933; Bhattacharjee S., et al., *Nanotoxicology*, (2011) DOI 10.3109/17435390.2011.633714, 1-14) Si can be used as vehicles for drug delivery and bioimaging. The Si nanoparticles, due to their very small sizes (<5 nm) and intrinsic fluorescence, enjoy an edge over other nanoparticles (such as polymers and carbon based nanoparticles) that need to be functionalized to be fluorescent (Bhattacharjee S., et al., *Nanotoxicology*, (2011) DOI 10.3109/17435390.2011.633714, 1-14; Chandra, et al., *Nanoscale* (2011) 3:1533-1540). In addition, unlike the popular but intrinsically toxic Cd-based bioimaging agents such as CdSe/ZnS QDs, Si nanoparticles are mostly non-toxic. It has recently been shown that with appropriate surface coating there is no toxicity in a rat lung and human colon cell lines (Bhattacharj ee S et al., (2012) "Cytotoxicity of surface-functionalized silicon and germanium nanoparticles: The dominant role of surface charges." *ACS Nano*, In press).

Mpr1, and fragments thereof, increase the permeability of the BBB. Eliminating Mpr1 from *C. neoformans* prevents brain infection and expressing Mpr1 in non-pathogenic yeast enables yeast to penetrate the BBB. Accordingly, conjugation of Mpr1 to silicon-based nanoparticles finds use in specifically targeting the migration of Mpr1-conjugated nanocarriers to the BBB resulting in a drug delivery system for the brain. The Mpr1-bioconjugated nanoparticles can be engineered to carry a therapeutic payload (e.g., a drug) for the treatment of a specific brain disorder.

Recombinant Mpr1 protein is produced using a eukaryote protein expression system and Mpr1 is conjugated to silicon-based nanoparticles. These nanoparticles are fast becoming the particles of choice due to their small size, biocompatibility and biodegradation. Once engineered, the Mpr1-conjugated nanoparticles are examined in our already established in vitro model of the human BBB. The biodistribution of Mpr1-conjugated-particles is investigated in mice through the use of PET or MRI at specific time points. For this kind of monitoring, the Mpr1-conjugating-particles are attached to a bifunctional DO3A derivative for chelation of $^{64}Cu$ for PET or doped with $Fe^{2+}$ or $Mn^{2+}$ for MRI. The biodegradability and biocompatibility of Mpr1-conjugated silicon nanoparticles in vivo are also monitored. We do this by: i) using confocal microscopy to observe the internalization and crossing of Mpr1-conjugated nanoparticles; ii) using Mpr1-conjugated nanoparticles radiolabeled with $^{64}Cu$-DO3A to quantify the number of particles internalized and crossing the BBB; iii) using TEM (Transmission Electron Microscopy) and SEM (Scanning Electron Microscopy) to observe the behavior of the Mpr1-nanoparticles within human brain endothelial cells and to look for any possible cell or organelle structural damage and iv) assessing the biodegradability and biocompatibility of Mpr1-conjugated nanoparticles.

Examination of Mpr1-Conjugated Nanoparticles In Vivo to Investigate the Biodistribution of Mpr1-Conjugated Nanoparticles.

A/Jr mice that are between 4-6 weeks old are inoculated via tail vein with silicon-nanoparticles alone or with Mpr1-conjugated-particles. A previous in vivo biodistribution study of mice inoculated with silicon-nanoparticles alone, found that the silicon-based particles accumulated largely in the liver, kidney and intestine with very little accumulation in the brain (Park et al., *Nature Materials* (2009) 8:331-336; Tu, et al., *Med. Chem. Letts.* (2011) 2:285-288, Bhattacharjee S et al., (2012). "Cytotoxicity of surface-functionalized silicon and germanium nanoparticles: The dominant role of surface charges." *ACS Nano*, In press). They also found that these particles were biodegradable and had negligible in vivo toxicity (Park et al., *Nature Materials* (2009) 8:331-336; Tu, et al., *Med. Chem. Letts.* (2011) 2:285-288, Bhattacharjee S et al., (2012). "Cytotoxicity of surface-functionalized silicon and germanium nanoparticles: The dominant role of surface charges." *ACS Nano*, In press). In our study, mice will be monitored either by PET or MRI at specific time points (1 h, 4 h, 24 h, 48 h) following the tail vein inoculations. For this kind of monitoring, the Mpr1-conjugating-particles will be attached to a bifunctional DO3A (1,4,7,10-tetraazacyclododecane-1,4,7-triacetic acid) derivative for chelation of $^{64}Cu$ for PET or doped with $Fe^{2+}$ or $Mn^{2+}$ for MRI (Tu, et al., *Med. Chem. Letts.* (2011) 2:285-288). To prevent rapid degradation after injection and increase their blood half-life, Mpr1-conjugated nanoparticles can be coated with the biopolymer dextran (Park et al., *Nature Materials* (2009) 8:331-336; Tu, et al., *Med. Chem. Letts.* (2011) 2:285-288). The concentrations of Mpr1-conjugated nanoparticles radiolabeled with $^{64}$Cu-DO3A are established semiquantitatively from PET images and used to analyze the biodistribution of Mpr1-nanoparticles in living mice over time. The biodistribution and deposition for Mpr1-conjugated particles is quantified in mice by gamma counting of ex vivo tissues. Mice used for PET are sacrificed following a PET scan at 48 h, and organs are harvested and analyzed quantitatively by a gamma-counter detector (and corrected for the natural decay of $^{64}$Cu).

Investigating the In Vivo Degradation and Toxicity of Mpr1-Conjugated Silicon Nanoparticles.

In order to examine the in vivo degradation of the Mpr1-particles, mice are sacrificed 1 day, 1 week and 4 weeks following tail vein injection. The brain, heart, kidney, liver, lung, and spleen are collected. The tissues are weighed, digested and then analyzed for silicon content using ICP-OES (inductively coupled plasma optical emission spectrometry, used for the detection of trace metals). To assess any potential in vivo toxicity with Mpr1-conjugated nanoparticles we perform toxicity studies. Here mice are weighed and monitored for any change in overall appearance, or behavior for 4 weeks following injection with Mpr1-particles and compared to control mice (tail vein injected with PBS). Tissue sections from brain, kidney, liver and spleen will be collected from mice 1 day and 4 weeks after injection with Mpr1-particles. Sections are stained with haematoxyline and eosin (H&E) and then examined by a pathologist.

An immune attack on the nanoparticles themselves can be avoided by coating the particles with biocompatible polymers like polyethylene glycol (PEG). It has been shown that nanoparticles coated with PEG are only minimally taken up by macrophages (Zahr, et al., Langmuir (Am Chem Soc) (2006) 22:8178-8185.). However, we may find that Mpr1 is immunogenic, which would imply that the Mpr1-conjugated-nanoparticles might be targeted for destruction by the immune system. We can address the potential immunogenicity of Mpr1 by: 1) immunosuppressing the animals by chemical induction before inoculation with the conjugate and 2) delivery vehicles can be further conjugated with specific peptides that will modulate the immune system and minimize an attack on the conjugate (Fang, et al., *Expt. Op. Bio. Ther.* (2012) 12:385-389, Zolnik et al., *Endocrinology* (2010) 151:458-465).

Example 5

Using Mpr1 to Target Stem Cells

Mpr1, or fragments thereof, can be expressed in stem cells. In varying embodiments, the FTP or pro-domain can be removed since this may act as an inhibitory domain. Normally Mpr1 is able to cleave this site and produce the active form of the protein, however, cells that normally do not produce Mpr1 may not be able to produce enzymatically active Mpr1 without removal of the FTP domain.

Standard molecular biology methods would be used to subclone Mpr1 into a commercially available mammalian expression vector under the control of a promoter (e.g., constitutive or inducible) in order to express Mpr1 in stem cells. Stem cells (e.g., neuronal, mesenchymal, induced pluripotent stem cells) are transfected (e.g., using commercially available methods) with the Mpr1-expression vector. Mpr1 expressed by the stem cells specifically targets the stem cells to the brain by facilitating their migration across the blood-brain barrier. The Mpr1-expressing stem cells are used as direct therapy in the case of neurodegeneration and/or are engineered to carry an antibody or peptide that acts to block tumor formation.

It is understood that the examples and embodiments described herein are for illustrative purposes only and that various modifications or changes in light thereof will be suggested to persons skilled in the art and are to be included within the spirit and purview of this application and scope of the appended claims. All publications, sequences identified by GenBank accession numbers, patents, and patent applications cited herein are hereby incorporated by reference in their entirety for all purposes.

```
INFORMAL SEQUENCE LISTING
Sequence ID No: 1 - amino acid sequence of MPR1 from Strain: Cryptococcus neoformans var. neoformans B-3501A Serotype D CNBJ1810 (locus tag)

Chromosome 10

Protein: 831 aa

Signal peptide: residues 1-20 (MRSSALIALLPLLATLVTAR)

FTP domain: residues 95-141
(DSYTDARTGVTHIFARQLLNGLEVSDGDINLNIDRDGRIISWGNSFH)

Peptidase M36 domain: residues 446-722
(TVGNNAYAHENWEGRNNFLLNSRPINDSHIFVYDYGEPEGLAPKEYVDMVVTQLFYTANM

YHDLLYRLGFDEISGNFQAYNFRLGGKGGDPVVCNAQDGSGYNNANFLTPPDGQAPRMRMY

IWDTATPYRDGDLEAGIVIHEYSHGLSTRLTGGPANSGCLGYGEAGGMGEGWGDAIATLVR

QVEEHKNFENGTDVFSMGAWAANTDRGIRNYKYSTNFTINPSTYKTLDKPGYWGVHAIGEV

WAEFLFVLSQRLVEKYGFGTTLFPPTDTSKPND)
```

-continued

Zinc Binding Domain: residues 586-590 (HEYSH)

```
   1 MRSSALIALL PLLATLVTAR PHHHEHKHSA SRTRKSLSFG PAHSHASFEV LDDAVHAIEP
  61 RGLIGEPIDV NRVAQTFLGS QLGAQEGEGF YIREDSYTDA RTGVTHIFAR QLLNGLEVSD
 121 GDINLNIDRD GRIISWGNSF HPGSAPSLSD IHSSSSGETE KVCATLHQQL DEHKAHLAEL
 181 KGETGVWGLV KSAAQVVLGS SLPQGEVDHH EIKKVHKSMR HIENHLHAVC RQSAASTQSM
 241 LSPVEALVSL LPRLSPIDDL EDISPLDLTC TPHHTLKPKP AFAEPPTEVI SGAALSKAGV
 301 VSDVSARLMY TQVSEGAPRL VWKYEVEMKD SWYEAYVDVL SGELIRVVDW ASDFDIDELR
 361 EKIEMMKGGK QKPLPSPPKT IKPYSYQVFP WGINDPVSGN LSVVTEPWDT VASPLGWHTF
 421 PTSANPWDVT IPGQTTNHNY TVFNTTVGNN AYAHENWEGR NNFLLNSRPI NDSHIFVYDY
 481 GEPEGLAPKE YVDMVVTQLF YTANMYHDLL YRLGFDEISG NFQAYNFRLG GKGGDPVVCN
 541 AQDGSGYNNA NFLTPPDGQA PRMRMYIWDT ATPYRDGDLE AGIVIHEYSH GLSTRLTGGP
 601 ANSGCLGYGE AGGMGEGWGD AIATLVRQVE EHKNFENGTD VFSMGAWAAN TDRGIRNYKY
 661 STNFTINPST YKTLDKPGYW GVHAIGEVWA EFLFVLSQRL VEKYGFGTTL FPPTDTSKPN
 721 DYYTRTSEES IDAGGRSLPL VPKHGNTLAI QLIVDAMKLQ PCRPSFFDAR NAIIQADQIL
 781 TGGENACLIW EAFAERGLGE DAAVVGQTPW GGGVRSDGFR VPKKVCGSKK A
```

Sequence ID No: 2 - nucleic acid sequence of MPR1 from

Strain: *Cryptococcus neoformans* var. *neoformans* B-3501A

Serotype D

CNBJ1810 (locus tag)

Chromosome 10

Gene: 2496 nt

```
   1 atgcgctcct ccgcgctcat cgcgcttctt cctctccttg ccactctggt tactgctcgt
  61 ccccatcatc atgagcacaa gcacagtgca tctagaactc gcaagtcatt atcctttgga
 121 cctgctcatt ctcatgcctc cttcgaggtt cttgatgatg ctgttcatgc catcgagcca
 181 cgtggcctca taggcgagcc tatcgatgtc aaccgagtgg ctcaaacctt cctcggatct
 241 cagctgggtg cccaggaggg cgaaggattc tacatccgag aagacagcta taccgatgcc
 301 cgaaccggcg tgacccatat cttcgctcgt caactcctca atggtcttga agtgtctgat
 361 ggcgatatca acctcaacat tgaccgtgat ggtcgaatca tatcttgggg taattcttc
 421 cacccaggat cagcccctag cctttccgac atccattctt cctcttcagg agaaactgaa
 481 aaggtctgcg cgacccttca ccaacagctt gacgagcaca aggcccattt ggctgagctg
 541 aagggtgaga ccggcgtctg ggacttgtt aagtcagccg cacaagttgt ccttggttct
 601 tccttgcctc agggtgaggt tgaccaccac gagatcaaga aggttcacaa gtccatgaga
 661 cacattgaaa accacttgca tgccgtgtgt cgccagtccg ctgccagcac ccagtctatg
 721 ctctcaccgg tggaagccct tgtttctctt cttccccgtc tctctcccat tgatgatctc
 781 gaggacattt cacctttaga cctaacctgt acaccccacc acactctcaa gcccaagccc
 841 gcctttgctg aacctcctac agaggtcatt tctggcgccg ctctttccaa ggctggcgtt
 901 gtatctgatg tctctgctcg tctcatgtac acacaggtct ctgagggtgc tcctcgcctt
 961 gtctggaaat atgaggttga gatgaaggac agttggtacg aggcttatgt ggatgtcctc
1021 tctggcgagc tcattcgagt ggtagactgg gcgagtgact ttgacattga tgaactcagg
1081 gagaaaattg agatgatgaa gggcggcaag cagaagcctt tgccctctcc tccgaagacg
1141 attaagccct attcttacca agtcttccct tggggtatca atgaccctgt ttccggcaac
1201 ttgtctgtgg tgacagagcc ttgggacaca gttgcctctc ctcttgggtg gcacacgttc
```

```
1261 cctacctccg ctaaccctg ggacgtcact attcctggtc agactacgaa tcacaactac 1321 accgttttca atactaccgt tggtaacaac gcttatgctc acgaaaactg ggaaggccgc 1381 aataacttct tgctcaactc ccgacctatc aatgactctc acattttgt gtacgactat 1441 ggggagccgg aaggcctcgc tccgaaggag tatgtcgaca tggttgtcac tcagctcttc 1501 tacacagcga atatgtacca cgatcttctc taccgtctcg gtttcgatga gatctccggt 1561 aacttccagg cttacaactt caggctcggt ggcaagggtg gcgaccctgt cgtctgtaat 1621 gctcaggacg gaagcggtta caacaatgcc aactttttga ctcctccgga tggtcaggct 1681 cctaggatga ggatgtacat ttgggacact gctactcctt atcgagatgg tgacctcgag 1741 gctggtattg tcattcacga gtacagccac ggtctctcaa ctcgtttgac tggtggccca 1801 gccaactctg gatgtctcgg ctacggtgaa gccggcggaa tgggcgaggg atggggtgat 1861 gctattgcta cccttgtcag acaggttgag gagcataaga acttcgagaa cggcaccgac 1921 gttttctcta tgggcgcctg ggctgccaac actgaccgag gtattagaaa ctacaagtac 1981 tctaccaatt ttacgattaa tccctctacg tacaagacct tagacaagcc tggttactgg 2041 ggtgttcacg ccattggtga ggtatgggcc gagttcctct tcgtcttgtc tcagcgtctc 2101 gttgaaaagt acggttttgg caccactctt ttccctccta ccgatacttc gaagcccaac 2161 gactactaca ccaggacttc cgaagagtcg attgatgcgg gtggtcgatc ccttcctctt 2221 gtcccgaaac acggtaatac ccttgccatt cagctcatcg ttgacgccat gaagcttcag 2281 ccctgtaggc catcgttctt cgatgcccgt aatgcaatca tacaggccga ccaaatcttg 2341 actggcggtg agaatgcctg tttgatctgg gaggcctttg ccgaacgtgg tttgggtgag 2401 gatgcggctg ttgttggcca gactccctgg ggtggtggtg ttaggagcga cggtttcagg 2461 gtccccaaga aggtctgcgg gtccaaaaag gcttga
```

SEQ ID NO: 3 - amino acid sequence for MPR1 from

Strain: *Cryptococcus neoformans* var. *neoformans* JEC21

Serotype D

CNJ01650 (locus tag)

Chromosome 10

Protein: 831 aa

Signal peptide: residues 1-20 (MRSSALIALLPLLATLVTAR)

FTP domain: residues 95-141
(DSYTDARTGVTHIFARQLLNGLEVSDGDINLNIDRDGRIISWGNSFH)

Peptidase M36 domain: residues 446-722
(TVGNNAYAHENWEGRNNFLLNSRPINDSHIFVYDYGEPEGLAPKEYVDMVVTQLFYTANM

YHDLLYRLGFDEISGNFQAYNFRLGGKGGDPVVCNAQDGSGYNNANFLTPPDGQAPRMRMY

IWDTATPYRDGDLEAGIVIHEYSHGLSTRLIGGPANSGCLGYGEAGGMGEGWGDAIATLVR

QVEEHKNFENGTDVFSMGAWAANTDRGIRNYKYSTNFTINPSTYKTLDKPGYWGVHAIGEV

WAEFLFVLSQRLVEKYGFGTTLFPPTDTSKPND)

Zinc Binding Domain: residues 586-590 (HEYSH)

```
  1 MRSSALIALL PLLATLVTAR PHHHEHKHSA SRTRKSLSFG PAHSHASFEV LDDAVHAIEP

61 RGLIGEPIDV NRVAQTFLGS QLGAQEGEGF YIREDSYTDA RTGVTHIFAR QLLNGLEVSD

121 GDINLNIDRD GRIISWGNSF HPGSAPSLSD IHSSSGETE KVCATLHQQL DEHKAHLAEL

181 KGETGVWGLV KSAAQVVLGS SLPQGEVDHH EIKKVHKSMR HIENHLHAVC RQSAASTQSM

241 LSPVEALVSL LPRLSPIDDL EDISPLDLTC TPHHTLKPKP AFAEPPTEVI SGAALSKAGV
```

-continued

```
301 VSDVSARLMY TQVSEGAPRL VWKYEVEMKD SWYEAYVDVL SGELIRVVDW ASDFDIDELR

361 EKIEMMKGGK QKPLPSPPKT IKPYSYQVFP WGINDPVSGN LSVVTEPWDT VASPLGWHTF

421 PTSANPWDVT IPGQTTNHNY TVFNTTVGNN AYAHENWEGR NNFLLNSRPI NDSHIFVYDY

481 GEPEGLAPKE YVDMVVTQLF YTANMYHDLL YRLGFDEISG NFQAYNFRLG GKGGDPVVCN

541 AQDGSGYNNA NFLTPPDGQA PRMRMYIWDT ATPYRDGDLE AGIVIHEYSH GLSTRLTGGP

601 ANSGCLGYGE AGGMGEGWGD AIATLVRQVE EHKNFENGTD VFSMGAWAAN TDRGIRNYKY

661 STNFTINPST YKTLDKPGYW GVHAIGEVWA EFLFVLSQRL VEKYGFGTTL FPPTDTSKPN

721 DYYTRTSEES IDAGGRSLPL VPKHGNTLAI QLIVDAMKLQ PCRPSFFDAR NAIIQADQIL

781 TGGENACLIW EAFAERGLGE DAAVVGQTPW GGGVRSDGFR VPKKVCGSKK A
```

SEQ ID NO: 4 - nucleic acid sequence for MPR1 from

Strain: *Cryptococcus neoformans* var. *neoformans* JEC21

Serotype D

CNJ01650 (locus tag)

Chromosome 10

Gene: 2496 nt

```
   1 atgcgctcct ccgcgctcat cgcgcttctt cctctccttg ccactctggt tactgctcgt
  61 ccccatcatc atgagcacaa gcacagtgca tctagaactc gcaagtcatt atcctttgga
 121 cctgctcatt ctcatgcctc cttcgaggtt cttgatgatg ctgttcatgc catcgagcca
 181 cgtggcctca taggcgagcc tatcgatgtc aaccgagtgg ctcaaacctt cctcggatct
 241 cagctgggtg cccaggaggg cgaaggattc tacatccgag aagacagcta taccgatgcc
 301 cgaaccggcg tgacccatat cttcgctcgt caactcctca atggtcttga agtgtctgat
 361 ggcgatatca acctcaacat tgaccgtgat ggtcgaatca tatcttgggg taattctttc
 421 cacccaggat cagcccctag cctttccgac atccattctt cctcttcagg agaaactgaa
 481 aaggtctgcg cgacccttca ccaacagctt gacgagcaca aggcccattt ggctgagctg
 541 aagggtgaga ccgcgtctg gggacttgtt aagtcagccg cacaagttgt ccttggttct
 601 tccttgcctc agggtgaggt tgaccaccac gagatcaaga aggttcacaa gtccatgaga
 661 cacattgaaa accacttgca tgccgtgtgt cgccagtccg ctgccagcac ccagtctatg
 721 ctctcaccgg tggaagccct tgtttctctt cttccccgtc tctctcccat tgatgatctc
 781 gaggacattt caccttttaga cctaacctgt acaccccacc acactctcaa gcccaagccc
 841 gcctttgctg aacctcctac agaggtcatt tctggcgccg ctctttccaa ggctggcgtt
 901 gtatctgatg tctctgctcg tctcatgtac acacaggtct ctgagggtgc tcctcgcctt
 961 gtctggaaat atgaggttga gatgaaggac agttggtacg aggcttatgt ggatgtcctc
1021 tctggcgagc tcattcgagt ggtagactgg gcgagtgact tgacattga tgaactcagg
1081 gagaaaattg agatgatgaa gggcggcaag cagaagcctt gccctctcc tccgaagacg
1141 attaagccct attcttacca agtcttccct tggggtatca atgaccctgt tccggcaac
1201 ttgtctgtgg tgacagagcc ttgggacaca gttgcctctc ctcttgggtg cacacgttc
1261 cctacctccg ctaaccctg ggacgtcact attcctggtc agactacgaa tcacaactac
1321 accgttttca atactaccgt tggtaacaac gcttatgctc acgaaaactg ggaaggccgc
1381 aataacttct tgctcaactc ccgacctatc aatgactctc acattttgt gtacgactat
1441 ggggagccga aggcctcgc tccgaaggag tatgtcgaca tggttgtcac tcagctcttc
1501 tacacagcga atatgtacca cgatcttctc taccgtctcg gtttcgatga gatctccggt
```

```
1561 aacttccagg cttacaactt caggctcggt ggcaagggtg gcgaccctgt cgtctgtaat 1621 gctcaggacg gaagcggtta caacaatgcc aactttttga ctcctccgga tggtcaggct 1681 cctaggatga ggatgtacat ttgggacact gctactcctt atcgagatgg tgacctcgag 1741 gctggtattg tcattcacga gtacagccac ggtctctcaa ctcgtttgac tggtggccca 1801 gccaactctg gatgtctcgg ctacggtgaa gccggcggaa tgggcgaggg atggggtgat 1861 gctattgcta cccttgtcag acaggttgag gagcataaga acttcgagaa cggcaccgac 1921 gttttctcta tgggcgcctg ggctgccaac actgaccgag gtattagaaa ctacaagtac 1981 tctaccaatt ttacgattaa tccctctacg tacaagacct tagacaagcc tggttactgg 2041 ggtgttcacg ccattggtga ggtatgggcc gagttcctct tcgtcttgtc tcagcgtctc 2101 gttgaaaagt acggttttgg caccactctt ttccctccta ccgatacttc gaagcccaac 2161 gactactaca ccaggacttc cgaagagtcg attgatgcgg gtggtcgatc ccttcctctt 2221 gtcccgaaac acggtaatac ccttgccatt cagctcatcg ttgacgccat gaagcttcag 2281 ccctgtaggc catcgttctt cgatgcccgt aatgcaatca tacaggccga ccaaatcttg 2341 actggcggtg agaatgcctg tttgatctgg gaggcctttg ccgaacgtgg tttgggtgag 2401 gatgcggctg ttgttggcca gactccctgg ggtggtggtg ttaggagcga cggtttcagg 2461 gtccccaaga aggtctgcgg gtccaaaaag gcttga
```

SEQ ID NO: 5 - amino acid sequence of MPR1 from

Strain: *Cryptococcus gattii* WM276

Serotype B

CGB_I230C (locus tag)

Chromosome I

Protein: 831 aa

Signal peptide: residues 1-20 (MRSSALIALLPLLATLTAAR)

FTP domain: residues 95-141
(DGYTDSRTGVTHIFARQLLNGLEVSDGDINLNIDRDGRIMSFGNSFH)

Peptidase M36 domain: residues 446-722
(TAGNNAIAQENWEGRNNFLLNYRPMNDSHMFMHEYGEPEGLAPKEYVDMIITQLFYTANM

YHDLLYRLGFNEVSGNFQAYNFGLGGKGGDPVVCNAQDGSGYNNANFLTPPDGQAPRMRMY

IWDTATPYRDGDLEAGIVIHEYSHGLSTRLIGGPANSGCLGYGEAGGMGEGWGDAIATLVR

QVEEHRNFENGTDVFPMGSWAANTPKGIRNYLYTTDPTVNPSTYKTLDKPGYWGVHAIGEV

WAEFLFVLSERFVETYGFGPTLFPPTNTSEPND)

Zinc Binding Domain: residues 586-590 (HEYSH)

```
  1 MRSSALIALL PLLATLTAAR PHHHEHKHSA SRTRKSLSFG PVHSHASFEV LTEAAPVIES

61 RQLKDEPMDV IRVAQTFLRS QLGTQEGEGF YIRDDGYTDS RTGVTHIFAR QLLNGLEVSD

121 GDINLNIDRD GRIMSFGNSF HPGSAPDLSA VHSSSSGETE RVCATLRQQL DEYKAHLAEL

181 KGETGVWGLV KSAAEVVLGS SMPQGEVDHH EIKKTIKSMS LIENHLQAVC HRPTASTQSM

241 LSPVDAVVSL LPRLSPNDDL EDISPLELTS TPHHTLKPKP AFAEPPTEVI SGAALSKAGV

301 VSDVPARLMY TQVSEGAPRL VWKCEVEMKD SWYEAYVDVF SGELIRVVDW ASDYDIDELI

361 KKIEMTNGGK QKPLPGPPEN AKPYSYLVFP WGVNDPLCGN LSVETEPWDT VASPLGWHMF

421 PNSANPWDVT IPGQHTNHTH TVFNTTAGNN AIAQENWEGR NNFLLNYRPM NDSHMFMHEY

481 GEPEGLAPKE YVDMIITQLF YTANMYHDLL YRLGFNEVSG NFQAYNFGLG GKGGDPVVCN

541 AQDGSGYNNA NFLTPPDGQA PRMRMYIWDT ATPYRDGDLE AGIVIHEYSH GLSTRLTGGP
```

```
601 ANSGCLGYGE AGGMGEGWGD AIATLVRQVE EHRNFENGTD VFPMGSWAAN TPKGIRNYLY
661 TTDPTVNPST YKTLDKPGYW GVHAIGEVWA EFLFVLSERF VETYGFGPTL FPPTNTSEPN
721 DYYTSTFEES VDAAGRPRPL VPKHGNTLAL QLIVDGMKLQ PCRPSFFDAR DAIIQADQIL
781 TGGENACLIW EAFAERGLGQ DATVVGQTPW GGGVRTDGHK VPKNICGSKK A
```

SEQ ID NO: 6 - nucleic acid sequence of MPR1 from

Strain: *Cryptococcus gattii* WM276

Serotype B

CGB_I230C (locus tag)

Chromosome I

Gene: 2469 nt 1 atgcgctcct ccgcgctcat tgccctcctt cctctcctcg ccactctgac tgctgctcgt 61 ccccatcatc atgagcacaa gcacagtgca tccaggactc gcaagtcatt gtcttttgga 121 cctgttcatt ctcatgcctc ctttgaggtt cttactgaag ctgctcctgt catcgagtca 181 cgtcaactca aagacgaacc tatggatgtc atacgagtcg ctcagacctt cctccgatct 241 cagctgggta cccaggaggg cgaaggattt tacattcgag acgacggcta taccgactct 301 cgaaccggcg tgacccacat ctttgctcgt caactcctca atggtcttga agtgtccgat 361 ggtgacatca acctcaacat tgaccgcgat ggtcggatca tgtcctttgg taattctttc 421 caccccggat cagcccctga cctttccgcc gtccattctt cttcttcggg cgaaaccgaa 481 agggtctgcg cgacccttcg tcaacagctt gacgagtaca aggcccactt ggctgaacta 541 aagggtgaga ccggtgtctg ggggcttgtc aagtctgccg cagaagttgt ccttggttct 601 tccatgccgc agggtgaggt tgaccaccac gagatcaaga agactattaa gtccatgagc 661 cttattgaaa accatttgca agccgtgtgc catcgaccca ctgccagtac ccaatctatg 721 ctctcgccag tagatgccgt tgtttctctt cttccccgtc tctctcccaa tgatgatctc 781 gaggacattt cacctcttga attaacctct actccccacc acactctcaa gcccaagccc 841 gcctttgccg aacctcctac tgaggtcatt tccggcgctg ctctttccaa ggctggcgtt 901 gtatctgatg ttcctgctcg gctcatgtat acccaggtct ccgagggtgc tcctcgcctt 961 gtctggaaat gtgaggttga gatgaaggac agttggtacg aggcttatgt tgatgtcttc 1021 tccggcgagc tcatacgagt ggttgactgg gcgagtgact atgacattga cgaactcata 1081 aagaaaattg agatgacgaa cggtggcaag cagaaacctt tgcccggtcc accggagaac 1141 gctaagccct actcttacct ggtcttcccc tggggtgtca atgaccctct ttgcggcaac 1201 ttgtctgtgg agacagaacc ctgggacaca gttgcctctc ctcttgggtg gcacatgttc 1261 cccaactcgg ctaacccctg ggatgtcacg attcctggcc agcatacgaa tcacacccac 1321 acagtcttca atactaccgc tggtaacaac gctattgctc aagaaaactg ggaaggccgc 1381 aataacttct tgctcaatta ccgacctatg aatgattctc acatgtttat gcacgagtat 1441 ggagagccgg aaggcctcgc tccgaaggag tacgtcgata tgattatcac tcagctcttt 1501 tacacagcga atatgtacca cgatcttctc taccgcctcg gttttaatga ggtctctggt 1561 aacttccagg cttacaattt tgggctcggt ggcaagggtg gagaccctgt cgtctgtaac 1621 gctcaggacg gaagcggtta caacaatgcc aacttcttga ctccccctga tggtcaagcc 1681 cctaggatga ggatgtacat ttgggacact gctactcctt accgcgatgg tgacctcgag 1741 gctggtattg tcattcacga gtacagccac ggtctctcaa ctcgccttac tggtggccca 1801 gccaattctg ggtgtctcgg atacggtgag gctggtggta tgggagaagg atggggtgat -continued

```
1861 gctattgcaa cccttgttag gcaggttgag gagcacagga atttcgagaa cggcaccgac 1921 gtcttcccta tgggttcttg ggctgccaac accccaaaag gtattcggaa ctacctgtac 1981 accaccgacc ctaccgtaaa tccctccact acaagacct tggataagcc tggttactgg 2041 ggtgtccacg ccattggtga ggtctgggcc gagttcctct tcgtcttgtc tgagcgtttt 2101 gttgaaacgt acggatttgg ccctactctt ttccctccta ccaatacttc gagcccaac 2161 gactactaca ccagtacttt cgaagagtca gtcgatgcgg ctggtcgacc ccgtcctctt 2221 gtcccgaagc acggtaatac tctagcccct cagttgatcg ttgacggcat gaagcttcag 2281 ccctgcaggc catcgttctt cgatgcccgt gatgcgatca ttcaggccga ccagatcttg 2341 actggcggtg agaatgcttg tttgatctgg gaggcctttg ccgaacgcgg tttgggtcag 2401 gacgcgactg ttgttggcca aactccttgg ggtggcggtg ttaggaccga cggccacaag 2461 gtcccgaaga atatctgcgg gtccaagaag gcttag
```

SEQ ID NO: 7 - amino acid sequence of MPR1 from

Strain: *Cryptococcus neoformans* var. *grubii* H99

CNAG_0735.2 (locus)

Chromosome 10 (location)

Protein: 722 aa

Signal peptide: residues 1-20 (MRSSALIALLPFLATLTAAR)

FTP domain: residues 95-141
(DSYTDARTGVTHIFARQLLNGLEVSDGDINLNIDRDGRIMSWGNSFH)

Peptidase M36 domain: residues 446-706
(TAGNNVYAHENWEGRNNFLLNYRPTNDSHIFVYEYGEPEGLAPKEYVDMVVTQLFYTANM

YHDLLYRLGFDELSGNFQAYNFRLGGKGGDPVVCNAQDGSGYNNANFLTPPDGQAPRMRMY

IWDTATPYRDGDLEAGIVIHEYSHGLSTRLIGGPANSGCLGYGEAGGMGEGWGDAIATLIR

QVEEHKNFENGTDVFSMGAWAANSNRGIRNYKYSTNFTINPSTYKTLDKPGYWGVHAIGEV

WAEFLFVLSQRLVENPAG)

Zinc Binding Domain: residues 586-590 (HEYSH)
<u>MRSSALIALLPFLATLTAAR</u>PHHREDKHSASRTRKSLSFGPAHSHASFEVLDDAVHVFEPRGLIDEPIDVKRVA

QTFLGSQLGAQEGEGFYIREDSYTDARTGVTHIFARQLLNGLEVSDGDINLNIDRDGRIMSWGNSFHPGSVPSL

SDIHSSSGETEKVCTTLHQHLDEHKAHLAELKGETGIWGLVKSAAQVVLGSSLPLGEVDHHEIKETHKSMRHI

ENHLRAMCDQPAVSTQSMLSPVEALVSLLPRLSPIDDLEDISPFDLTSTPHHTLKPKPAFAEPPTEVISGAALS

KAGVVSDVSARLMYTQVSEGAPRLVWKYEVEMKDSWYEAYVDVLSGELIRVVDWASDFDIDELRDKIEMMKGGK

QKPLPIPPKKIQPYSYQVFPWGINDPVSGNLSVVTEPWDTVASPLGWHSFPTSANPWDVTIPGETTNHNYTVFN

<u>TTAGNNVYAHENWEGRNNFLLNYRPTNDSHIFVYEYGEPEGLAPKEYVDMVVTQLFYTANMYHDLLYRLGFDEL</u>

<u>SGNFQAYNFRLGGKGGDPVVCNAQDGSGYNNANFLTPPDGQAPRMRMYIWDTATPYRDGDLEAGIVIHEYSHGL</u>

<u>STRLTGGPANSGCLGYGEAGGMGEGWGDAIATLIRQVEEHKNFENGTDVFSMGAWAANSNRGIRNYKYSTNFTI</u>

<u>NPSTYKTLDKPGYWGVHAIGEVWAEFLEVLSQRLVENPAG</u>HHSSMPVMRSFRPTKS*

SEQ ID NO: 8 - nucleic acid sequence of MPR1 from

Strain: *Cryptococcus neoformans* var. *grubii* H99

CNAG_0735.2 (locus)

Chromosome 10 (location)

Gene: 3074 nt (the following sequence includes introns)
tctgttccataaactactcatagctcggcttccttctatacactactgtagcattaccgtagtatcgccaccat gcgctcctccgcgctcatcgctcttcttcctttccttgccaccctgactgctgctcgtcccatcatcgtgagg ataagcatagtgcatctaggactcgcaagtcattatcctttggacctgctcattctcatgcctccttcgaggtt cttgatgatgctgttcacgtcttcgagccacgtggactcatagacgagcctatcgatgtcaaacgagtggctca gactttcctcggatctcagttgggtgcccaggagggcgagggattctacattcgagaagacgtaagtgttctgc tgtggttctctatttttgactgggactagcgtggtatcctttcgtaggatggcatggcggacgacgtaacgcta acgattcgcagagctataccgatgcccgaaccggcgtgacccatattttcgctcgtcaactcctcaatggcctt gaagtatccgatggcgacatcaacctcaacattgaccgtgatggtcgaatcatgtcatgggtaattctttcca ccccggatcagtccctagccttccgacatccattcttcctcttcgggcgaaactgaaaaggtttgcacgaccc ttcaccaacatcttgacgagcacaaggcccacttggctgagctgaaaggtgagaccggtatctgggacttgtc aagtctgcagcacaagttgttctcggttcttccttgcctctgggtgaggttgaccaccacgagatcaaggagac tcacaagtccatgaggcatattgaaaaccacctgcgtgccatgtgcgaccagccggctgtcagcacccaatcta tgctctcgccggtggaggcccttgtttctcttcttcccgtctctctcccattgatgatctcgaggacatttca ccgtttgacttaacctctacaccccaccacactctcaagcccaagcccgcctttgctgaacctcctactgaggt catttctggcgctgcactttccaaggctggcgttgtatctgatgtctctgcgcgactcatgtacacacaggtct ctgagggtgctcctcgccttgtctggaaatatgaggttgagatgaaggacagttggtacgaggcttacgtggat gtcctctcaggcgagctcattcggtggtagactgggcgagtgactttgacattgatgaactcagggataaaat tgagatgatgaagggcggcaagcagaaacctttgcccattccccgaagaagattcagccctactcttaccaag tcttcccttggggtgagttgctttatctcgcattaccccctattgtgctaatgtattgtgcgccaggtatcaatg accctgtttccggcaacttgtctgtggtgacagagccttgggacacagttgcctctcctcttgggtggcactcg ttccctacttccgctaacccctgggatgtcaccattcctggtgagactacgaatcacaactacaccgttttcaa tactactgctggtaataacgtttatgcgcacgaaaactgggaaggccgcaataacttcttgctcaactaccgac ctaccaatgattctcacatctttgtgtacgaatatggagagccggaaggcctcgctccgaaggagtatgtcgac atggttgtcactcagctcttctacacggcgaatatgtaccacgatcttctctaccgtctcggcttcgatgagtt atccggtaacttccaggcttacaatttcaggcttggtggcaagggtggcgaccctgtcgtttgtaatgctcagg atggaagtggttacaataatgccaactttttgactcctccggatggccaggctcctaggatgaggatgtacatt tgggacacagctactccttatcgggatggtgacctcgaggctggtattgtcattcacgagtacaggtatgtctg cttgacacttttttacttcactgtattaacgcgccacaagccacggtctctcaactcgtctgactggtggtcca gccaactctgggtgtctcggataccggtgaagccggcggtatgggtgagggatggggcgatgctattgccaccct tatcaggcaggttgaggagcataagaacttcgagtaggttagataatcacgcatgttcctgcagaaaaactaat ttgtgaacatgtagaaacggcaccgacgttttctctatgggcgcctgggctgccaacagtaaccgaggtattag gaattacaagtactctaccaatttcacgattaatccctctacttacaagacccttagacaagcctggtaagtacg attttgaaccatgtcatcaagcagacagcttagacagcttatatccattaaaggttactgggggtccacgcca ttggtgaggtatgggccgagttcctcttcgtcttgtctcagcgcctcgttgaaaagtacggttttgggcccact cttttcccctcctaccgatacttcgaagcacaacgactactacaccaggacttccgaagagtcggttgatgccgc tggtcgacccttcctcttgtcccgaaatacggtaatgctcttgccattcagctcatcgttgacgccatgaagc

```
ttcagccctgcaggccatcattcttcgatgcccgtaatgcgatcattcaggccgaccaaatcttgactggcggt gagaatgcttgtttgatctggcaggcctttgccgaacgtggtttgggtgaggatgcggccgttgttggccagac gccctggggtggtggtgttaggagcgacggtttcaaggtccccaagaaggtctgcgagtccaaaaaggcttgaa agatgaaagcgctgtattctgatctagaatcttaccccgttccaagctagagttctgtactttgaattttgtac gatagcatgtgtatggtcttttatgttctgccattgatcatcttgaagattgatgttgtagtcgaatagatct ttgttgaagtgaatccttaactatatgcaacgatcgcaaa
```

What is claimed is:

1. An expression cassette comprising a nucleic acid encoding a M36 fungalysin metalloprotease or fragment thereof having at least 95% sequence identity to residues 446-722 of SEQ ID NO:1, operably linked to a heterologous promoter that promotes expression in a mammalian cell.

2. The expression cassette of claim 1, wherein the M36 fungalysin metalloprotease fragment does not comprise a fungalysin/thermolysin propeptide (FTP) domain.

3. The expression cassette of claim 1, wherein the M36 fungalysin metalloprotease fragment does not comprise a N-terminal signal peptide and a propeptide FTP domain.

4. The expression cassette of claim 1, wherein the M36 fungalysin metalloprotease fragment does not comprise N-terminal amino acid residues 1-300 of SEQ ID NO:1.

5. The expression cassette of claim 1, wherein the M36 fungalysin metalloprotease fragment does not comprise N-terminal amino acid residues 1-375 of SEQ ID NO:1.

6. The expression cassette of claim 1, wherein the promoter is a mammalian promoter.

7. The expression cassette of claim 1, wherein the promoter is a constitutive promoter.

8. The expression cassette of claim 1, wherein the promoter is an inducible promoter.

9. The expression cassette of claim 1, wherein the nucleic acid encoding the M36 fungalysin metalloprotease or fragment thereof is operably linked to a nucleic acid encoding a signal peptide the promotes the secretion and/or cell surface expression of the M36 fungalysin metalloprotease or fragment thereof.

10. The expression cassette of claim 1, wherein the nucleic acid has at least 85%, 86%, 87%, 88%, 89%, 90%, 91%, 92%, 93%, 94%, 95%, 96%, 97%, 98%, 99% or 100% sequence identity to SEQ ID NO: 2.

11. A host cell comprising the expression cassette of claim 1.

12. The host cell of claim 11, wherein the host cell is not a *Cryptococcus* cell.

13. The host cell of claim 11, wherein the host cell is a mammalian cell.

14. The host cell of claim 11, wherein the host cell is a stem cell.

15. The host cell of claim 14, wherein the stem cell is a neuronal stem cell, a mesenchymal stem cell or an induced pluripotent stem cell.

16. The host cell of claim 11, wherein the host cell can cross the blood-brain barrier of a mammalian subject.

17. The host cell of claim 11, wherein the host cell secretes the M36 fungalysin metalloprotease or fragment thereof.

18. The host cell of claim 11, wherein the M36 fungalysin metalloprotease or fragment thereof is retained on the surface of the cell.

19. The host cell of claim 11, wherein the M36 fungalysin metalloprotease or fragment thereof is embedded in the membrane of the cell.

* * * * *

SEQUENCE LISTING

<160> NUMBER OF SEQ ID NOS: 10

<210> SEQ ID NO 1
<211> LENGTH: 831
<212> TYPE: PRT
<213> ORGANISM: Cryptococcus neoformans

<400> SEQUENCE: 1

```
Met Arg Ser Ser Ala Leu Ile Ala Leu Leu Pro Leu Leu Ala Thr Leu
1               5                   10                  15

Val Thr Ala Arg Pro His His Glu His Lys His Ser Ala Ser Arg
            20                  25                  30

Thr Arg Lys Ser Leu Ser Phe Gly Pro Ala His Ser His Ala Ser Phe
        35                  40                  45

Glu Val Leu Asp Asp Ala Val His Ala Ile Glu Pro Arg Gly Leu Ile
    50                  55                  60

Gly Glu Pro Ile Asp Val Asn Arg Val Ala Gln Thr Phe Leu Gly Ser
65                  70                  75                  80

Gln Leu Gly Ala Gln Glu Gly Glu Gly Phe Tyr Ile Arg Glu Asp Ser
                85                  90                  95

Tyr Thr Asp Ala Arg Thr Gly Val Thr His Ile Phe Ala Arg Gln Leu
            100                 105                 110

Leu Asn Gly Leu Glu Val Ser Asp Gly Asp Ile Asn Leu Asn Ile Asp
        115                 120                 125

Arg Asp Gly Arg Ile Ile Ser Trp Gly Asn Ser Phe His Pro Gly Ser
    130                 135                 140

Ala Pro Ser Leu Ser Asp Ile His Ser Ser Ser Gly Glu Thr Glu
145                 150                 155                 160

Lys Val Cys Ala Thr Leu His Gln Gln Leu Asp Glu His Lys Ala His
                165                 170                 175

Leu Ala Glu Leu Lys Gly Glu Thr Gly Val Trp Gly Leu Val Lys Ser
            180                 185                 190

Ala Ala Gln Val Val Leu Gly Ser Ser Leu Pro Gln Gly Glu Val Asp
        195                 200                 205

His His Glu Ile Lys Lys Val His Lys Ser Met Arg His Ile Glu Asn
    210                 215                 220

His Leu His Ala Val Cys Arg Gln Ser Ala Ala Ser Thr Gln Ser Met
225                 230                 235                 240

Leu Ser Pro Val Glu Ala Leu Val Ser Leu Pro Arg Leu Ser Pro
                245                 250                 255

Ile Asp Asp Leu Glu Asp Ile Ser Pro Leu Asp Leu Thr Cys Thr Pro
            260                 265                 270

His His Thr Leu Lys Pro Lys Pro Ala Phe Ala Glu Pro Pro Thr Glu
        275                 280                 285
```

-continued

```
Val Ile Ser Gly Ala Ala Leu Ser Lys Ala Gly Val Val Ser Asp Val
    290                 295                 300

Ser Ala Arg Leu Met Tyr Thr Gln Val Ser Glu Gly Ala Pro Arg Leu
305                 310                 315                 320

Val Trp Lys Tyr Glu Val Glu Met Lys Asp Ser Trp Tyr Glu Ala Tyr
                325                 330                 335

Val Asp Val Leu Ser Gly Glu Leu Ile Arg Val Val Asp Trp Ala Ser
                340                 345                 350

Asp Phe Asp Ile Asp Glu Leu Arg Glu Lys Ile Glu Met Met Lys Gly
            355                 360                 365

Gly Lys Gln Lys Pro Leu Pro Ser Pro Lys Thr Ile Lys Pro Tyr
    370                 375                 380

Ser Tyr Gln Val Phe Pro Trp Gly Ile Asn Asp Pro Val Ser Gly Asn
385                 390                 395                 400

Leu Ser Val Val Thr Glu Pro Trp Asp Thr Val Ala Ser Pro Leu Gly
                405                 410                 415

Trp His Thr Phe Pro Thr Ser Ala Asn Pro Trp Asp Val Thr Ile Pro
                420                 425                 430

Gly Gln Thr Thr Asn His Asn Tyr Thr Val Phe Asn Thr Thr Val Gly
            435                 440                 445

Asn Asn Ala Tyr Ala His Glu Asn Trp Glu Gly Arg Asn Asn Phe Leu
450                 455                 460

Leu Asn Ser Arg Pro Ile Asn Asp Ser His Ile Phe Val Tyr Asp Tyr
465                 470                 475                 480

Gly Glu Pro Glu Gly Leu Ala Pro Lys Glu Tyr Val Asp Met Val Val
                485                 490                 495

Thr Gln Leu Phe Tyr Thr Ala Asn Met Tyr His Asp Leu Leu Tyr Arg
                500                 505                 510

Leu Gly Phe Asp Glu Ile Ser Gly Asn Phe Gln Ala Tyr Asn Phe Arg
            515                 520                 525

Leu Gly Gly Lys Gly Asp Pro Val Val Cys Asn Ala Gln Asp Gly
    530                 535                 540

Ser Gly Tyr Asn Asn Ala Asn Phe Leu Thr Pro Pro Asp Gly Gln Ala
545                 550                 555                 560

Pro Arg Met Arg Met Tyr Ile Trp Asp Thr Ala Thr Pro Tyr Arg Asp
                565                 570                 575

Gly Asp Leu Glu Ala Gly Ile Val Ile His Glu Tyr Ser His Gly Leu
            580                 585                 590

Ser Thr Arg Leu Thr Gly Gly Pro Ala Asn Ser Gly Cys Leu Gly Tyr
    595                 600                 605

Gly Glu Ala Gly Gly Met Gly Glu Gly Trp Gly Asp Ala Ile Ala Thr
610                 615                 620

Leu Val Arg Gln Val Glu Glu His Lys Asn Phe Glu Asn Gly Thr Asp
625                 630                 635                 640

Val Phe Ser Met Gly Ala Trp Ala Ala Asn Thr Asp Arg Gly Ile Arg
                645                 650                 655

Asn Tyr Lys Tyr Ser Thr Asn Phe Thr Ile Asn Pro Ser Thr Tyr Lys
                660                 665                 670

Thr Leu Asp Lys Pro Gly Tyr Trp Gly Val His Ala Ile Gly Glu Val
            675                 680                 685

Trp Ala Glu Phe Leu Phe Val Leu Ser Gln Arg Leu Val Glu Lys Tyr
    690                 695                 700
```

```
Gly Phe Gly Thr Thr Leu Phe Pro Pro Thr Asp Thr Ser Lys Pro Asn
705                 710                 715                 720

Asp Tyr Tyr Thr Arg Thr Ser Glu Glu Ser Ile Asp Ala Gly Gly Arg
                725                 730                 735

Ser Leu Pro Leu Val Pro Lys His Gly Asn Thr Leu Ala Ile Gln Leu
            740                 745                 750

Ile Val Asp Ala Met Lys Leu Gln Pro Cys Arg Pro Ser Phe Phe Asp
        755                 760                 765

Ala Arg Asn Ala Ile Ile Gln Ala Asp Gln Ile Leu Thr Gly Gly Glu
    770                 775                 780

Asn Ala Cys Leu Ile Trp Glu Ala Phe Ala Glu Arg Gly Leu Gly Glu
785                 790                 795                 800

Asp Ala Ala Val Val Gly Gln Thr Pro Trp Gly Gly Val Arg Ser
                805                 810                 815

Asp Gly Phe Arg Val Pro Lys Lys Val Cys Gly Ser Lys Lys Ala
            820                 825                 830

<210> SEQ ID NO 2
<211> LENGTH: 2496
<212> TYPE: DNA
<213> ORGANISM: Cryptococcus neoformans

<400> SEQUENCE: 2
```

| | | | | | |
|---|---|---|---|---|---|
| atgcgctcct | ccgcgctcat | cgcgcttctt | cctctccttg | ccactctggt | tactgctcgt | 60 |
| ccccatcatc | atgagcacaa | gcacagtgca | tctagaactc | gcaagtcatt | atcctttgga | 120 |
| cctgctcatt | ctcatgcctc | cttcgaggtt | cttgatgatg | ctgttcatgc | catcgagcca | 180 |
| cgtggcctca | taggcgagcc | tatcgatgtc | aaccgagtgg | ctcaaacctt | cctcggatct | 240 |
| cagctgggtg | cccaggaggg | cgaaggattc | tacatccgag | aagacagcta | taccgatgcc | 300 |
| cgaaccggcg | tgacccatat | cttcgctcgt | caactcctca | atggtcttga | agtgtctgat | 360 |
| ggcgatatca | acctcaacat | tgaccgtgat | ggtcgaatca | tatcttgggg | taattctttc | 420 |
| cacccaggat | cagcccctag | ccttccgac | atccattctt | cctcttcagg | agaaactgaa | 480 |
| aaggtctgcg | cgacccttca | ccaacagctt | gacgagcaca | aggcccattt | ggctgagctg | 540 |
| aagggtgaga | ccggcgtctg | gggacttgtt | aagtcagccg | cacaagttgt | ccttggttct | 600 |
| tccttgcctc | agggtgaggt | tgaccaccac | gagatcaaga | aggttcacaa | gtccatgaga | 660 |
| cacattgaaa | accacttgca | tgccgtgtgt | cgccagtccg | ctgccagcac | ccagtctatg | 720 |
| ctctcaccgg | tggaagccct | tgtttctctt | cttccccgtc | tctctcccat | tgatgatctc | 780 |
| gaggacattt | cacctttaga | cctaacctgt | acaccccacc | acactctcaa | gcccaagccc | 840 |
| gcctttgctg | aacctcctac | agaggtcatt | tctggcgccg | ctcttccaa | ggctggcgtt | 900 |
| gtatctgatg | tctctgctcg | tctcatgtac | acacaggtct | ctgagggtgc | tcctcgcctt | 960 |
| gtctggaaat | atgaggttga | gatgaaggac | agttggtacg | aggcttatgt | ggatgtcctc | 1020 |
| tctggcgagc | tcattcgagt | ggtagactgg | gcgagtgact | ttgacattga | tgaactcagg | 1080 |
| gagaaaattg | agatgatgaa | gggcggcaag | cagaagcctt | gccctctcc | tccgaagacg | 1140 |
| attaagccct | attcttacca | agtcttccct | tggggtatca | atgaccctgt | ttccggcaac | 1200 |
| ttgtctgtgg | tgacagagcc | ttgggacaca | gttgcctctc | ctcttgggtg | gcacacgttc | 1260 |
| cctacctccg | ctaaccctg | ggacgtcact | attcctggtc | agactacgaa | tcacaactac | 1320 |
| accgttttca | atactaccgt | tggtaacaac | gcttatgctc | acgaaaactg | ggaaggccgc | 1380 |
| aataacttct | tgctcaactc | ccgacctatc | aatgactctc | acatttttgt | gtacgactat | 1440 |

```
ggggagccgg aaggcctcgc tccgaaggag tatgtcgaca tggttgtcac tcagctcttc    1500
tacacagcga atatgtacca cgatcttctc taccgtctcg gtttcgatga gatctccggt    1560
aacttccagg cttacaactt caggctcggt ggcaagggtg gcgaccctgt cgtctgtaat    1620
gctcaggacg gaagcggtta caacaatgcc aacttttga ctcctccgga tggtcaggct    1680
cctaggatga ggatgtacat ttgggacact gctactcctt atcgagatgg tgacctcgag    1740
gctggtattg tcattcacga gtacagccac ggtctctcaa ctcgtttgac tggtggccca    1800
gccaactctg gatgtctcgg ctacggtgaa gccggcggaa tgggcgaggg atggggtgat    1860
gctattgcta cccttgtcag acaggttgag gagcataaga acttcgagaa cggcaccgac    1920
gttttctcta tgggcgcctg ggctgccaac actgaccgag gtattagaaa ctacaagtac    1980
tctaccaatt ttacgattaa tccctctacg tacaagacct tagacaagcc tggttactgg    2040
ggtgttcacg ccattggtga ggtatgggcc gagttcctct tcgtcttgtc tcagcgtctc    2100
gttgaaaagt acggttttgg caccactctt ttccctccta ccgatacttc gaagcccaac    2160
gactactaca ccaggacttc cgaagagtcg attgatgcgg gtggtcgatc ccttcctctt    2220
gtcccgaaac acgtaatac ccttgccatt cagctcatcg ttgacgccat gaagcttcag    2280
ccctgtaggc catcgttctt cgatgcccgt aatgcaatca tacaggccga ccaaatcttg    2340
actggcggtg agaatgcctg tttgatctgg gaggcctttg ccgaacgtgg tttgggtgag    2400
gatgcggctg ttgttggcca gactccctgg ggtggtggtg ttaggagcga cggtttcagg    2460
gtccccaaga aggtctgcgg gtccaaaaag gcttga                              2496

<210> SEQ ID NO 3
<211> LENGTH: 831
<212> TYPE: PRT
<213> ORGANISM: Cryptococcus neoformans

<400> SEQUENCE: 3

Met Arg Ser Ser Ala Leu Ile Ala Leu Leu Pro Leu Leu Ala Thr Leu
1               5                   10                  15

Val Thr Ala Arg Pro His His His Glu His Lys His Ser Ala Ser Arg
            20                  25                  30

Thr Arg Lys Ser Leu Ser Phe Gly Pro Ala His Ser His Ala Ser Phe
        35                  40                  45

Glu Val Leu Asp Asp Ala Val His Ala Ile Glu Pro Arg Gly Leu Ile
    50                  55                  60

Gly Glu Pro Ile Asp Val Asn Arg Val Ala Gln Thr Phe Leu Gly Ser
65                  70                  75                  80

Gln Leu Gly Ala Gln Glu Gly Glu Gly Phe Tyr Ile Arg Glu Asp Ser
                85                  90                  95

Tyr Thr Asp Ala Arg Thr Gly Val Thr His Ile Phe Ala Arg Gln Leu
            100                 105                 110

Leu Asn Gly Leu Glu Val Ser Asp Gly Asp Ile Asn Leu Asn Ile Asp
        115                 120                 125

Arg Asp Gly Arg Ile Ile Ser Trp Gly Asn Ser Phe His Pro Gly Ser
    130                 135                 140

Ala Pro Ser Leu Ser Asp Ile His Ser Ser Ser Gly Glu Thr Glu
145                 150                 155                 160

Lys Val Cys Ala Thr Leu His Gln Gln Leu Asp Glu His Lys Ala His
                165                 170                 175

Leu Ala Glu Leu Lys Gly Glu Thr Gly Val Trp Gly Leu Val Lys Ser
```

```
                180                 185                 190
    Ala Ala Gln Val Val Leu Gly Ser Ser Leu Pro Gln Gly Glu Val Asp
                    195                 200                 205
    His His Glu Ile Lys Lys Val His Lys Ser Met Arg His Ile Glu Asn
                    210                 215                 220
    His Leu His Ala Val Cys Arg Gln Ser Ala Ala Ser Thr Gln Ser Met
    225                 230                 235                 240
    Leu Ser Pro Val Glu Ala Leu Val Ser Leu Pro Arg Leu Ser Pro
                    245                 250                 255
    Ile Asp Asp Leu Glu Asp Ile Ser Pro Leu Asp Leu Thr Cys Thr Pro
                    260                 265                 270
    His His Thr Leu Lys Pro Lys Pro Ala Phe Ala Glu Pro Thr Glu
                    275                 280                 285
    Val Ile Ser Gly Ala Ala Leu Ser Lys Ala Gly Val Val Ser Asp Val
                    290                 295                 300
    Ser Ala Arg Leu Met Tyr Thr Gln Val Ser Glu Gly Ala Pro Arg Leu
    305                 310                 315                 320
    Val Trp Lys Tyr Glu Val Glu Met Lys Asp Ser Trp Tyr Glu Ala Tyr
                    325                 330                 335
    Val Asp Val Leu Ser Gly Glu Leu Ile Arg Val Val Asp Trp Ala Ser
                    340                 345                 350
    Asp Phe Asp Ile Asp Glu Leu Arg Glu Lys Ile Glu Met Met Lys Gly
                    355                 360                 365
    Gly Lys Gln Lys Pro Leu Pro Ser Pro Pro Lys Thr Ile Lys Pro Tyr
                    370                 375                 380
    Ser Tyr Gln Val Phe Pro Trp Gly Ile Asn Asp Pro Val Ser Gly Asn
    385                 390                 395                 400
    Leu Ser Val Val Thr Glu Pro Trp Asp Thr Val Ala Ser Pro Leu Gly
                    405                 410                 415
    Trp His Thr Phe Pro Thr Ser Ala Asn Pro Trp Asp Val Thr Ile Pro
                    420                 425                 430
    Gly Gln Thr Thr Asn His Asn Tyr Thr Val Phe Asn Thr Thr Val Gly
                    435                 440                 445
    Asn Asn Ala Tyr Ala His Glu Asn Trp Glu Gly Arg Asn Asn Phe Leu
                    450                 455                 460
    Leu Asn Ser Arg Pro Ile Asn Asp Ser His Ile Phe Val Tyr Asp Tyr
    465                 470                 475                 480
    Gly Glu Pro Glu Gly Leu Ala Pro Lys Glu Tyr Val Asp Met Val Val
                    485                 490                 495
    Thr Gln Leu Phe Tyr Thr Ala Asn Met Tyr His Asp Leu Leu Tyr Arg
                    500                 505                 510
    Leu Gly Phe Asp Glu Ile Ser Gly Asn Phe Gln Ala Tyr Asn Phe Arg
                    515                 520                 525
    Leu Gly Gly Lys Gly Gly Asp Pro Val Val Cys Asn Ala Gln Asp Gly
                    530                 535                 540
    Ser Gly Tyr Asn Asn Ala Asn Phe Leu Thr Pro Pro Asp Gly Gln Ala
    545                 550                 555                 560
    Pro Arg Met Arg Met Tyr Ile Trp Asp Thr Ala Thr Pro Tyr Arg Asp
                    565                 570                 575
    Gly Asp Leu Glu Ala Gly Ile Val Ile His Glu Tyr Ser His Gly Leu
                    580                 585                 590
    Ser Thr Arg Leu Thr Gly Gly Pro Ala Asn Ser Gly Cys Leu Gly Tyr
                    595                 600                 605
```

```
Gly Glu Ala Gly Gly Met Gly Glu Gly Trp Gly Asp Ala Ile Ala Thr
    610                 615                 620
Leu Val Arg Gln Val Glu His Lys Asn Phe Glu Asn Gly Thr Asp
625                 630                 635                 640
Val Phe Ser Met Gly Ala Trp Ala Ala Asn Thr Asp Arg Gly Ile Arg
                    645                 650                 655
Asn Tyr Lys Tyr Ser Thr Asn Phe Thr Ile Asn Pro Ser Thr Tyr Lys
                660                 665                 670
Thr Leu Asp Lys Pro Gly Tyr Trp Gly Val His Ala Ile Gly Glu Val
            675                 680                 685
Trp Ala Glu Phe Leu Phe Val Leu Ser Gln Arg Leu Val Glu Lys Tyr
    690                 695                 700
Gly Phe Gly Thr Thr Leu Phe Pro Pro Thr Asp Thr Ser Lys Pro Asn
705                 710                 715                 720
Asp Tyr Tyr Thr Arg Thr Ser Glu Glu Ser Ile Asp Ala Gly Gly Arg
                    725                 730                 735
Ser Leu Pro Leu Val Pro Lys His Gly Asn Thr Leu Ala Ile Gln Leu
                740                 745                 750
Ile Val Asp Ala Met Lys Leu Gln Pro Cys Arg Pro Ser Phe Phe Asp
            755                 760                 765
Ala Arg Asn Ala Ile Ile Gln Ala Asp Gln Ile Leu Thr Gly Gly Glu
    770                 775                 780
Asn Ala Cys Leu Ile Trp Glu Ala Phe Ala Glu Arg Gly Leu Gly Glu
785                 790                 795                 800
Asp Ala Ala Val Val Gly Gln Thr Pro Trp Gly Gly Val Arg Ser
                    805                 810                 815
Asp Gly Phe Arg Val Pro Lys Lys Val Cys Gly Ser Lys Lys Ala
                820                 825                 830

<210> SEQ ID NO 4
<211> LENGTH: 2496
<212> TYPE: DNA
<213> ORGANISM: Cryptococcus neoformans

<400> SEQUENCE: 4
atgcgctcct ccgcgctcat cgcgcttctt cctctccttg ccactctggt tactgctcgt    60
ccccatcatc atgagcacaa gcacagtgca tctagaactc gcaagtcatt atcctttgga   120
cctgctcatt tcatgcctc cttcgaggtt cttgatgatg ctgttcatgc catcgagcca   180
cgtggcctca taggcgagcc tatcgatgtc aaccgagtgg ctcaaacctt cctcggatct   240
cagctgggtg cccaggaggg cgaaggattc tacatccgag aagacagcta taccgatgcc   300
cgaaccggcg tgacccatat cttcgctcgt caactcctca atggtcttga agtgtctgat   360
ggcgatatca acctcaacat tgaccgtgat ggtcgaatca tatcttgggg taattctttc   420
cacccaggat cagcccctag cctttccgac atccattctt cctcttcagg agaaactgaa   480
aaggtctgcg cgacccttca ccaacagctt gacgagcaca aggcccattt ggctgagctg   540
aagggtgaga ccggcgtctg gggacttgtt aagtcagccg cacaagttgt ccttggttct   600
tccttgcctc agggtgaggt tgaccaccac gagatcaaga aggttcacaa gtccatgaga   660
cacattgaaa accacttgca tgccgtgtgt cgccagtccg ctgccagcac ccagtctatg   720
ctctcaccgg tggaagccct tgtttctctt cttccccgtc tctctcccat tgatgatctc   780
gaggacattt caccttaga cctaacctgt acacccccacc acactctcaa gcccaagccc   840
```

-continued

```
gcctttgctg aacctcctac agaggtcatt tctggcgccg ctctttccaa ggctggcgtt      900
gtatctgatg tctctgctcg tctcatgtac acacaggtct ctgagggtgc tcctcgcctt      960
gtctggaaat atgaggttga gatgaaggac agttggtacg aggcttatgt ggatgtcctc     1020
tctggcgagc tcattcgagt ggtagactgg gcgagtgact ttgacattga tgaactcagg     1080
gagaaaattg agatgatgaa gggcggcaag cagaagcctt gccctctcc tccgaagacg      1140
attaagccct attcttacca agtcttccct tggggtatca atgaccctgt tccggcaac     1200
ttgtctgtgg tgacagagcc ttgggacaca gttgcctctc ctcttgggtg cacacgttc     1260
cctacctccg ctaaccctg gacgtcact attcctggtc agactacgaa tcacaactac      1320
accgttttca atactaccgt tggtaacaac gcttatgctc acgaaaactg ggaaggccgc     1380
aataacttct tgctcaactc ccgacctatc aatgactctc acattttgt gtacgactat      1440
ggggagccgg aaggcctcgc tccgaaggag tatgtcgaca tggttgtcac tcagctcttc     1500
tacacagcga atatgtacca cgatcttctc taccgtctcg gtttcgatga gatctccggt     1560
aacttccagg cttacaactt caggctcggt ggcaaggggtg cgaccctgt cgtctgtaat    1620
gctcaggacg aagcggtta caacaatgcc aactttttga ctcctccgga tggtcaggct     1680
cctaggatga ggatgtacat ttgggacact gctactcctt atcgagatgg tgacctcgag     1740
gctggtattg tcattcacga gtacagccac ggtctctcaa ctcgtttgac tggtggccca     1800
gccaactctg gatgtctcgg ctacggtgaa gccggcggaa tgggcgaggg atggggtgat     1860
gctattgcta cccttgtcag acaggttgag gagcataaga acttcgagaa cggcaccgac     1920
gttttctcta tgggcgcctg ggctgccaac actgaccgag gtattagaaa ctacaagtac     1980
tctaccaatt ttacgattaa tccctctacg tacaagacct agacaagcc tggttactgg     2040
ggtgttcacg ccattggtga ggtatgggcc gagttcctct tcgtcttgtc tcagcgtctc     2100
gttgaaaagt acggttttgg caccactctt ttccctccta ccgatacttc gaagcccaac     2160
gactactaca ccaggacttc cgaagagtcg attgatgcgg gtggtcgatc ccttcctctt     2220
gtcccgaaac acggtaatac ccttgccatt cagctcatcg ttgacgccat gaagcttcag     2280
ccctgtaggc catcgttctt cgatgcccgt aatgcaatca tacaggccga ccaaatcttg     2340
actggcggtg agaatgcctg tttgatctgg gaggcctttg ccgaacgtgg tttgggtgag     2400
gatgcggctg ttgttggcca gactccctgg ggtggtggtg ttaggagcga cggtttcagg     2460
gtccccaaga aggtctgcgg gtccaaaaag gcttga                              2496
```

<210> SEQ ID NO 5
<211> LENGTH: 831
<212> TYPE: PRT
<213> ORGANISM: Cryptococcus gattii

<400> SEQUENCE: 5

```
Met Arg Ser Ser Ala Leu Ile Ala Leu Leu Pro Leu Leu Ala Thr Leu
1               5                   10                  15

Thr Ala Ala Arg Pro His His Glu His Lys His Ser Ala Ser Arg
            20                  25                  30

Thr Arg Lys Ser Leu Ser Phe Gly Pro Val His Ser His Ala Ser Phe
        35                  40                  45

Glu Val Leu Thr Glu Ala Ala Pro Val Ile Glu Ser Arg Gln Leu Lys
    50                  55                  60

Asp Glu Pro Met Asp Val Ile Arg Val Ala Gln Thr Phe Leu Arg Ser
65                  70                  75                  80
```

```
Gln Leu Gly Thr Gln Glu Gly Glu Gly Phe Tyr Ile Arg Asp Asp Gly
             85                  90                  95
Tyr Thr Asp Ser Arg Thr Gly Val Thr His Ile Phe Ala Arg Gln Leu
            100                 105                 110
Leu Asn Gly Leu Glu Val Ser Asp Gly Asp Ile Asn Leu Asn Ile Asp
        115                 120                 125
Arg Asp Gly Arg Ile Met Ser Phe Gly Asn Ser Phe His Pro Gly Ser
    130                 135                 140
Ala Pro Asp Leu Ser Ala Val His Ser Ser Ser Gly Glu Thr Glu
145                 150                 155                 160
Arg Val Cys Ala Thr Leu Arg Gln Gln Leu Asp Glu Tyr Lys Ala His
                165                 170                 175
Leu Ala Glu Leu Lys Gly Glu Thr Gly Val Trp Gly Leu Val Lys Ser
            180                 185                 190
Ala Ala Glu Val Val Leu Gly Ser Ser Met Pro Gln Gly Glu Val Asp
        195                 200                 205
His His Glu Ile Lys Lys Thr Ile Lys Ser Met Ser Leu Ile Glu Asn
    210                 215                 220
His Leu Gln Ala Val Cys His Arg Pro Thr Ala Ser Thr Gln Ser Met
225                 230                 235                 240
Leu Ser Pro Val Asp Ala Val Val Ser Leu Leu Pro Arg Leu Ser Pro
                245                 250                 255
Asn Asp Asp Leu Glu Asp Ile Ser Pro Leu Glu Leu Thr Ser Thr Pro
            260                 265                 270
His His Thr Leu Lys Pro Lys Pro Ala Phe Ala Glu Pro Pro Thr Glu
        275                 280                 285
Val Ile Ser Gly Ala Ala Leu Ser Lys Ala Gly Val Val Ser Asp Val
    290                 295                 300
Pro Ala Arg Leu Met Tyr Thr Gln Val Ser Glu Gly Ala Pro Arg Leu
305                 310                 315                 320
Val Trp Lys Cys Glu Val Glu Met Lys Asp Ser Trp Tyr Glu Ala Tyr
                325                 330                 335
Val Asp Val Phe Ser Gly Glu Leu Ile Arg Val Val Asp Trp Ala Ser
            340                 345                 350
Asp Tyr Asp Ile Asp Glu Leu Ile Lys Lys Ile Glu Met Thr Asn Gly
        355                 360                 365
Gly Lys Gln Lys Pro Leu Pro Gly Pro Pro Glu Asn Ala Lys Pro Tyr
    370                 375                 380
Ser Tyr Leu Val Phe Pro Trp Gly Val Asn Asp Pro Leu Cys Gly Asn
385                 390                 395                 400
Leu Ser Val Glu Thr Glu Pro Trp Asp Thr Val Ala Ser Pro Leu Gly
                405                 410                 415
Trp His Met Phe Pro Asn Ser Ala Asn Pro Trp Asp Val Thr Ile Pro
            420                 425                 430
Gly Gln His Thr Asn His Thr His Thr Val Phe Asn Thr Thr Ala Gly
        435                 440                 445
Asn Asn Ala Ile Ala Gln Glu Asn Trp Glu Gly Arg Asn Asn Phe Leu
    450                 455                 460
Leu Asn Tyr Arg Pro Met Asn Asp Ser His Met Phe Met His Glu Tyr
465                 470                 475                 480
Gly Glu Pro Glu Gly Leu Ala Pro Lys Glu Tyr Val Asp Met Ile Ile
                485                 490                 495
Thr Gln Leu Phe Tyr Thr Ala Asn Met Tyr His Asp Leu Leu Tyr Arg
```

```
                500             505             510
Leu Gly Phe Asn Glu Val Ser Gly Asn Phe Gln Ala Tyr Asn Phe Gly
            515                 520                 525

Leu Gly Gly Lys Gly Gly Asp Pro Val Val Cys Asn Ala Gln Asp Gly
            530                 535                 540

Ser Gly Tyr Asn Asn Ala Asn Phe Leu Thr Pro Pro Asp Gly Gln Ala
545                 550                 555                 560

Pro Arg Met Arg Met Tyr Ile Trp Asp Thr Ala Thr Pro Tyr Arg Asp
                565                 570                 575

Gly Asp Leu Glu Ala Gly Ile Val Ile His Glu Tyr Ser His Gly Leu
            580                 585                 590

Ser Thr Arg Leu Thr Gly Gly Pro Ala Asn Ser Gly Cys Leu Gly Tyr
            595                 600                 605

Gly Glu Ala Gly Gly Met Gly Glu Gly Trp Gly Asp Ala Ile Ala Thr
            610                 615                 620

Leu Val Arg Gln Val Glu Glu His Arg Asn Phe Glu Asn Gly Thr Asp
625                 630                 635                 640

Val Phe Pro Met Gly Ser Trp Ala Ala Asn Thr Pro Lys Gly Ile Arg
                645                 650                 655

Asn Tyr Leu Tyr Thr Thr Asp Pro Thr Val Asn Pro Ser Thr Tyr Lys
                660                 665                 670

Thr Leu Asp Lys Pro Gly Tyr Trp Gly Val His Ala Ile Gly Glu Val
            675                 680                 685

Trp Ala Glu Phe Leu Phe Val Leu Ser Glu Arg Phe Val Glu Thr Tyr
            690                 695                 700

Gly Phe Gly Pro Thr Leu Phe Pro Pro Thr Asn Thr Ser Glu Pro Asn
705                 710                 715                 720

Asp Tyr Tyr Thr Ser Thr Phe Glu Glu Ser Val Asp Ala Ala Gly Arg
                725                 730                 735

Pro Arg Pro Leu Val Pro Lys His Gly Asn Thr Leu Ala Leu Gln Leu
            740                 745                 750

Ile Val Asp Gly Met Lys Leu Gln Pro Cys Arg Pro Ser Phe Phe Asp
            755                 760                 765

Ala Arg Asp Ala Ile Ile Gln Ala Asp Gln Ile Leu Thr Gly Gly Glu
            770                 775                 780

Asn Ala Cys Leu Ile Trp Glu Ala Phe Ala Glu Arg Gly Leu Gly Gln
785                 790                 795                 800

Asp Ala Thr Val Val Gly Gln Thr Pro Trp Gly Gly Val Arg Thr
                805                 810                 815

Asp Gly His Lys Val Pro Lys Asn Ile Cys Gly Ser Lys Lys Ala
            820                 825                 830

<210> SEQ ID NO 6
<211> LENGTH: 2496
<212> TYPE: DNA
<213> ORGANISM: Cryptococcus gattii

<400> SEQUENCE: 6
atgcgctcct ccgcgctcat tgccctcctt cctctcctcg ccactctgac tgctgctcgt      60
ccccatcatc atgagcacaa gcacagtgca tccaggactc gcaagtcatt gtcttttgga    120
cctgttcatt tcatgcctc ctttgaggtt cttactgaag ctgctcctgt catcgagtca     180
cgtcaactca aagacgaacc tatggatgtc atacgagtcg ctcagacctt cctccgatct    240
cagctgggta cccaggaggg cgaaggattt tacattcgag acgacggcta taccgactct    300
```

```
cgaaccggcg tgacccacat ctttgctcgt caactcctca atggtcttga agtgtccgat    360
ggtgacatca acctcaacat tgaccgcgat ggtcggatca tgtcctttgg taattctttc    420
cacccggat  cagcccctga cctttccgcc gtccattctt cttcttcggg cgaaaccgaa    480
agggtctgcg cgacccttcg tcaacagctt gacgagtaca aggcccactt ggctgaacta    540
aagggtgaga ccggtgtctg ggggcttgtc aagtctgccg cagaagttgt ccttggttct    600
tccatgccgc agggtgaggt tgaccaccac gagatcaaga agactattaa gtccatgagc    660
cttattgaaa accatttgca agccgtgtgc catcgaccca ctgccagtac ccaatctatg    720
ctctcgccag tagatgccgt tgtttctctt cttccccgtc tctctcccaa tgatgatctc    780
gaggacattt cacctcttga attaacctct actccccacc acactctcaa gcccaagccc    840
gcctttgccg aacctcctac tgaggtcatt tccggcgctg ctctttccaa ggctggcgtt    900
gtatctgatg ttcctgctcg gctcatgtat acccaggtct ccgagggtgc tcctcgcctt    960
gtctggaaat gtgaggttga gatgaaggac agttggtacg aggcttatgt tgatgtcttc   1020
tccggcgagc tcatacgagt ggttgactgg gcgagtgact atgacattga cgaactcata   1080
aagaaaattg agatgacgaa cggtggcaag cagaaacctt tgcccggtcc accggagaac   1140
gctaagccct actcttacct ggtcttcccc tggggtgtca atgaccctct ttgcggcaac   1200
ttgtctgtgg agacagaacc ctgggacaca gttgcctctc ctcttgggtg gcacatgttc   1260
cccaactcgg ctaaccctg  gatgtcacg  attcctggcc agcatacgaa tcacacccac   1320
acagtcttca atactaccgc tggtaacaac gctattgctc aagaaaactg ggaaggccgc   1380
aataacttct tgctcaatta ccgacctatg aatgattctc acatgtttat gcacgagtat   1440
ggagagccgg aaggcctcgc tccgaaggag tacgtcgata tgattatcac tcagctcttt   1500
tacacagcga atatgtacca cgatcttctc taccgcctcg gttttaatga ggtctctggt   1560
aacttccagg cttacaattt tgggctcggt ggcaagggtg agaccctgt  cgtctgtaac   1620
gctcaggacg gaagcggtta caacaatgcc aacttcttga ctccccctga tggtcaagcc   1680
cctaggatga ggatgtacat ttgggacact gctactcctt accgcgatgg tgacctcgag   1740
gctggtattg tcattcacga gtacagccac ggtctctcaa ctcgccttac tggtggccca   1800
gccaattctg ggtgtctcgg atacggtgag gctggtggta tgggagaagg atggggtgat   1860
gctattgcaa cccttgttag gcaggttgag gagcacagga atttcgagaa cggcaccgac   1920
gtcttcccta tgggttcttg ggctgccaac accccaaaag gtattcggaa ctacctgtac   1980
accaccgacc ctaccgtaaa tccctccact tacaagacct tggataagcc tggttactgg   2040
ggtgtccacg ccattggtga ggtctgggcc gagttcctct tcgtcttgtc tgagcgtttt   2100
gttgaaacgt acggatttgg ccctactctt ttccctccta ccaatacttc cgagcccaac   2160
gactactaca ccagtacttt cgaagagtca gtcgatgcgg ctggtcgacc ccgtcctctt   2220
gtcccgaagc acggtaatac tctagccctt cagttgatcg ttgacggcat gaagcttcag   2280
ccctgcaggc catcgttctt cgatgcccgt gatgcgatca ttcaggccga ccagatcttg   2340
actggcggtg agaatgcttg tttgatctgg gaggcctttg ccgaacgcgg tttgggtcag   2400
gacgcgactg ttgttggcca aactccttgg ggtggcggtg ttaggaccga cggccacaag   2460
gtcccgaaga atatctgcgg gtccaagaag gcttag                             2496
```

<210> SEQ ID NO 7
<211> LENGTH: 722
<212> TYPE: PRT

-continued

<213> ORGANISM: Cryptococcus neoformans

<400> SEQUENCE: 7

```
Met Arg Ser Ser Ala Leu Ile Ala Leu Leu Pro Phe Leu Ala Thr Leu
1               5                   10                  15

Thr Ala Ala Arg Pro His His Arg Glu Asp Lys His Ser Ala Ser Arg
            20                  25                  30

Thr Arg Lys Ser Leu Ser Phe Gly Pro Ala His Ser His Ala Ser Phe
        35                  40                  45

Glu Val Leu Asp Asp Ala Val His Val Phe Glu Pro Arg Gly Leu Ile
    50                  55                  60

Asp Glu Pro Ile Asp Val Lys Arg Val Ala Gln Thr Phe Leu Gly Ser
65                  70                  75                  80

Gln Leu Gly Ala Gln Glu Gly Glu Gly Phe Tyr Ile Arg Glu Asp Ser
                85                  90                  95

Tyr Thr Asp Ala Arg Thr Gly Val Thr His Ile Phe Ala Arg Gln Leu
            100                 105                 110

Leu Asn Gly Leu Glu Val Ser Asp Gly Asp Ile Asn Leu Asn Ile Asp
        115                 120                 125

Arg Asp Gly Arg Ile Met Ser Trp Gly Asn Ser Phe His Pro Gly Ser
130                 135                 140

Val Pro Ser Leu Ser Asp Ile His Ser Ser Ser Gly Glu Thr Glu
145                 150                 155                 160

Lys Val Cys Thr Thr Leu His Gln His Leu Asp Glu His Lys Ala His
                165                 170                 175

Leu Ala Glu Leu Lys Gly Glu Thr Gly Ile Trp Gly Leu Val Lys Ser
            180                 185                 190

Ala Ala Gln Val Val Leu Gly Ser Ser Leu Pro Leu Gly Glu Val Asp
        195                 200                 205

His His Glu Ile Lys Glu Thr His Lys Ser Met Arg His Ile Glu Asn
    210                 215                 220

His Leu Arg Ala Met Cys Asp Gln Pro Ala Val Ser Thr Gln Ser Met
225                 230                 235                 240

Leu Ser Pro Val Glu Ala Leu Val Ser Leu Pro Arg Leu Ser Pro
                245                 250                 255

Ile Asp Asp Leu Glu Asp Ile Ser Pro Phe Asp Leu Thr Ser Thr Pro
            260                 265                 270

His His Thr Leu Lys Pro Lys Pro Ala Phe Ala Glu Pro Pro Thr Glu
        275                 280                 285

Val Ile Ser Gly Ala Ala Leu Ser Lys Ala Gly Val Val Ser Asp Val
290                 295                 300

Ser Ala Arg Leu Met Tyr Thr Gln Val Ser Glu Gly Ala Pro Arg Leu
305                 310                 315                 320

Val Trp Lys Tyr Glu Val Glu Met Lys Asp Ser Trp Tyr Glu Ala Tyr
                325                 330                 335

Val Asp Val Leu Ser Gly Glu Leu Ile Arg Val Val Asp Trp Ala Ser
            340                 345                 350

Asp Phe Asp Ile Asp Glu Leu Arg Asp Lys Ile Glu Met Met Lys Gly
        355                 360                 365

Gly Lys Gln Lys Pro Leu Pro Ile Pro Pro Lys Lys Ile Gln Pro Tyr
    370                 375                 380

Ser Tyr Gln Val Phe Pro Trp Gly Ile Asn Asp Pro Val Ser Gly Asn
385                 390                 395                 400
```

Leu Ser Val Val Thr Glu Pro Trp Asp Thr Val Ala Ser Pro Leu Gly
            405                 410                 415

Trp His Ser Phe Pro Thr Ser Ala Asn Pro Trp Asp Val Thr Ile Pro
        420                 425                 430

Gly Glu Thr Thr Asn His Asn Tyr Thr Val Phe Asn Thr Thr Ala Gly
            435                 440                 445

Asn Asn Val Tyr Ala His Glu Asn Trp Glu Gly Arg Asn Asn Phe Leu
450                 455                 460

Leu Asn Tyr Arg Pro Thr Asn Asp Ser His Ile Phe Val Tyr Glu Tyr
465                 470                 475                 480

Gly Glu Pro Glu Gly Leu Ala Pro Lys Glu Tyr Val Asp Met Val Val
                485                 490                 495

Thr Gln Leu Phe Tyr Thr Ala Asn Met Tyr His Asp Leu Leu Tyr Arg
            500                 505                 510

Leu Gly Phe Asp Glu Leu Ser Gly Asn Phe Gln Ala Tyr Asn Phe Arg
        515                 520                 525

Leu Gly Gly Lys Gly Gly Asp Pro Val Val Cys Asn Ala Gln Asp Gly
    530                 535                 540

Ser Gly Tyr Asn Asn Ala Asn Phe Leu Thr Pro Pro Asp Gly Gln Ala
545                 550                 555                 560

Pro Arg Met Arg Met Tyr Ile Trp Asp Thr Ala Thr Pro Tyr Arg Asp
                565                 570                 575

Gly Asp Leu Glu Ala Gly Ile Val Ile His Glu Tyr Ser His Gly Leu
            580                 585                 590

Ser Thr Arg Leu Thr Gly Pro Ala Asn Ser Gly Cys Leu Gly Tyr
        595                 600                 605

Gly Glu Ala Gly Gly Met Gly Glu Gly Trp Gly Asp Ala Ile Ala Thr
    610                 615                 620

Leu Ile Arg Gln Val Glu Glu His Lys Asn Phe Glu Asn Gly Thr Asp
625                 630                 635                 640

Val Phe Ser Met Gly Ala Trp Ala Ala Asn Ser Asn Arg Gly Ile Arg
                645                 650                 655

Asn Tyr Lys Tyr Ser Thr Asn Phe Thr Ile Asn Pro Ser Thr Tyr Lys
            660                 665                 670

Thr Leu Asp Lys Pro Gly Tyr Trp Gly Val His Ala Ile Gly Glu Val
        675                 680                 685

Trp Ala Glu Phe Leu Phe Val Leu Ser Gln Arg Leu Val Glu Asn Pro
    690                 695                 700

Ala Gly His His Ser Ser Met Pro Val Met Arg Ser Phe Arg Pro Thr
705                 710                 715                 720

Lys Ser

<210> SEQ ID NO 8
<211> LENGTH: 3074
<212> TYPE: DNA
<213> ORGANISM: Cryptococcus neoformans

<400> SEQUENCE: 8
tctgttccat aaactactca tagctcggct tccttctata cactactgta gcattaccgt     60
agtatcgcca ccatgcgctc ctccgcgctc atcgctcttc ttcctttcct tgccaccctg    120
actgctgctc gtccccatca tcgtgaggat aagcatagtg catctaggac tcgcaagtca    180
ttatcctttg gacctgctca ttctcatgcc tccttcgagg ttcttgatga tgctgttcac    240
gtcttcgagc cacgtggact catagacgag cctatcgatg tcaaacgagt ggctcagact    300

```
ttcctcggat ctcagttggg tgcccaggag ggcgagggat tctacattcg agaagacgta      360
agtgttctgc tgtggttctc tattttgac tgggactagc gtggtatcct ttcgtaggat       420
ggcatggcgg acgacgtaac gctaacgatt cgcagagcta taccgatgcc cgaaccggcg      480
tgacccatat tttcgctcgt caactcctca atggccttga agtatccgat ggcgacatca      540
acctcaacat tgaccgtgat ggtcgaatca tgtcatgggg taattctttc cacccggat      600 cagtccctag cctttccgac atccattctt cctcttcggg cgaaactgaa aaggtttgca      660 cgaccttca ccaacatctt gacgagcaca aggcccactt ggctgagctg aaaggtgaga      720
ccggtatctg gggacttgtc aagtctgcag cacaagttgt tctcggttct tccttgcctc     780
tgggtgaggt tgaccaccac gagatcaagg agactcacaa gtccatgagg catattgaaa     840
accacctgcg tgccatgtgc gaccagccgg ctgtcagcac ccaatctatg ctctcgccgg     900
tggaggccct tgtttctctt cttccccgtc tctctcccat tgatgatctc gaggacattt     960
caccgtttga cttaacctct acacccacc acactctcaa gcccaagccc gcctttgctg      1020
aacctcctac tgaggtcatt tctggcgctg cactttccaa ggctggcgtt gtatctgatg     1080
tctctgcgcg actcatgtac acacaggtct ctgaggtgc cctcgcctt gtctggaaat      1140 atgaggttga gatgaaggac agttggtacg aggcttacgt ggatgtcctc tcaggcgagc     1200
tcattcgggt ggtagactgg gcgagtgact ttgacattga tgaactcagg gataaaattg     1260
agatgatgaa gggcggcaag cagaaacctt gcccattcc cccgaagaag attcagccct      1320
actcttacca agtcttccct tggggtgagt tgctttatct cgcattaccc ctattgtgct     1380
aatgtattgt gcgccaggta tcaatgaccc tgtttccggc aacttgtctg tggtgacaga     1440
gccttgggac acagttgcct ctcctcttgg gtggcactcg ttccctactt ccgctaaccc     1500
ctgggatgtc accattcctg gtgagactac gaatcacaac tacaccgttt tcaatactac     1560
tgctggtaat aacgttatg cgcacgaaaa ctgggaaggc cgcaataact tcttgctcaa      1620
ctaccgacct accaatgatt ctcacatctt tgtgtacgaa tatggagagc cggaaggcct     1680
cgctccgaag gagtatgtcg acatggttgt cactcagctc ttctacacgg cgaatatgta     1740
ccacgatctt ctctaccgtc tcggcttcga tgagttatcc ggtaacttcc aggcttacaa     1800
tttcaggctt ggtggcaagg gtggcgaccc tgtcgtttgt aatgctcagg atggaagtgg     1860
ttacaataat gccaactttt tgactcctcc ggatggccag gctcctagga tgaggatgta     1920
catttgggac acagctactc cttatcggga tggtgacctc gaggctggta ttgtcattca     1980
cgagtacagg tatgtctgct tgacactttt ttacttcact gtattaacgc gccacaagcc     2040
acggtctctc aactcgtctg actggtggtc cagccaactc tgggtgtctc ggatacggtg     2100
aagccggcgg tatgggtgag ggatggggcg atgctattgc caccttatc aggcaggttg      2160 aggagcataa gaacttcgag taggttagat aatcacgcat gttcctgcag aaaaactaat     2220
ttgtgaacat gtagaaacgg caccgacgtt ttctctatgg gcgcctgggc tgccaacagt     2280
aaccgaggta ttaggaatta caagtactct accaatttca cgattaatcc ctctacttac     2340
aagaccttag acaagcctgg taagtacgat tttgaaccat gtcatcaagc agacagctta     2400
gacagcttat atccattaaa ggttactggg gggtccacgc cattggtgag gtatgggccg     2460
agttcctctt cgtcttgtct cagcgcctcg ttgaaaagta cggttttggg cccactcttt     2520
tccctcctac cgatacttcg aagcacaacg actactacac caggacttcc gaagagtcgg     2580
ttgatgccgc tggtcgaccc cttcctcttg tcccgaaata cggtaatgct cttgccattc     2640
```

-continued

```
agctcatcgt tgacgccatg aagcttcagc cctgcaggcc atcattcttc gatgcccgta    2700
atgcgatcat tcaggccgac caaatcttga ctggcggtga gaatgcttgt ttgatctggc    2760
aggcctttgc cgaacgtggt ttgggtgagg atgcggccgt tgttggccag acgccctggg    2820
gtggtggtgt taggagcgac ggtttcaagg tccccaagaa ggtctgcgag tccaaaaagg    2880
cttgaaagat gaaagcgctg tattctgatc tagaatctta ccccgttcca agctagagtt    2940
ctgtactttg aattttgtac gatagcatgt gtatggtctt tttatgttct gccattgatc    3000
atcttgaaga ttgatgttgt agtcgaatag atctttgttg aagtgaatcc ttaactatat    3060
gcaacgatcg caaa                                                      3074

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acttccaggc ttacaatttc ag                                             22

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agatttggtc ggcctgaatg atcg                                           24
```